US010640496B2

(12) United States Patent
Yoon et al.

(10) Patent No.: US 10,640,496 B2
(45) Date of Patent: May 5, 2020

(54) METHOD FOR PRODUCING DIPHENYLMETHANE DERIVATIVE

(71) Applicants: DAEWOONG PHARMACEUTICAL CO., LTD., Hwaseong-si, Gyeonggi-do (KR); GREEN CROSS CORPORATION, Yongin, Gyeonggi-do (KR)

(72) Inventors: Hee-kyoon Yoon, Cheongju-si (KR); Se-Hwan Park, Yongin-si (KR); Ji-sung Yoon, Yongi-si (KR); Soongyu Choi, Yongin-si (KR); Hee Jeong Seo, Yongin-si (KR); Eun-Jung Park, Yongin-si (KR); Younggyu Kong, Yongin-si (KR); Kwang-Seop Song, Yongin-si (KR); Min Ju Kim, Yongin-si (KR); So Ok Park, Yongin-si (KR)

(73) Assignees: DAEWOONG PHARMACEUTICAL CO., LTD., Hwaseong-si (KR); GREEN CROSS CORPORATION, Yongin (KR)

( * ) Notice: Subject to any disclaimer, the term of this patent is extended or adjusted under 35 U.S.C. 154(b) by 0 days.

(21) Appl. No.: 16/310,005

(22) PCT Filed: Jun. 15, 2017

(86) PCT No.: PCT/KR2017/006271
§ 371 (c)(1),
(2) Date: Dec. 14, 2018

(87) PCT Pub. No.: WO2017/217792
PCT Pub. Date: Dec. 21, 2017

(65) Prior Publication Data
US 2019/0169174 A1  Jun. 6, 2019

(30) Foreign Application Priority Data
Jun. 17, 2016 (KR) .................. 10-2016-0075910

(51) Int. Cl.
| | | |
|---|---|---|
| *C07D 409/04* | (2006.01) | |
| *C07D 407/04* | (2006.01) | |
| *C07D 307/78* | (2006.01) | |
| *B01D 9/00* | (2006.01) | |
| *C07B 51/00* | (2006.01) | |

(52) U.S. Cl.
CPC .......... *C07D 409/04* (2013.01); *B01D 9/005* (2013.01); *C07D 307/78* (2013.01); *C07D 407/04* (2013.01); *C07B 51/00* (2013.01); *C07B 2200/13* (2013.01); *Y02P 20/55* (2015.11)

(58) Field of Classification Search
CPC ............. C07D 409/04; C07D 407/04

USPC ................................. 549/414, 356
See application file for complete search history.

(56) References Cited

U.S. PATENT DOCUMENTS

| | | | | |
|---|---|---|---|---|
| 9,034,921 | B2 * | 5/2015 | Choi ..................... | C07D 309/10 |
| | | | | 514/460 |
| 9,340,521 | B2 * | 5/2016 | Choi ..................... | C07D 309/10 |
| 2014/0274918 | A1 | 9/2014 | Choi et al. | |
| 2015/0152075 | A1 | 6/2015 | Choi et al. | |

FOREIGN PATENT DOCUMENTS

| | | |
|---|---|---|
| KR | 10-2014-022086 A | 2/2014 |
| KR | 2014-0114304 A | 9/2014 |
| WO | 2009/014970 A1 | 1/2009 |
| WO | 2011048112 A1 | 4/2011 |
| WO | 2012-041898 A1 | 4/2012 |
| WO | 2015-124877 A1 | 8/2015 |

OTHER PUBLICATIONS

Bastin, et al. "Salt Selection and Optimisation Procedures for Pharmaceutical New Chemical Entities", Organic Process & Development, 2000, vol. 4, pp. 427-435 (9 pages total).
Balbach, et al., "Pharmaceutical evaluation of early development candidates the 100 mg-approach", International Journal of Pharmaceutics, 2004, vol. 275, pp. 1-12 (12 pages total).
Singhal, et al., "Drug polymorphism and dosage form design: a practical perspective", Advanced Drug Delivery Reviews, 2004, vol. 56, pp. 335-347 (13 pages total).
Caira, "Crystalline Polymorphism of Organic Compounds", Design of Organic solids, Topics in Current Chemistry, Springer, 1998, vol. 198, pp. 163-208 (46 pages total).
Suk Youn Kang et al., "Glucosides with Cyclic Diarylpolynoid as Novel C-aryl glucoside SGLT2 Inhibitors", Bioorganic & Medicinal Chemistry Letters, Dec. 21, 2011, pp. 3759-3763.
International Search Report of PCT/KR2017/006271 dated Sep. 19, 2017.
Baihua Xu, et al., "C-Aryl glucosides substituted at the 4'-position as potent and selective renal sodium-dependent glucose cotransporter 2 (SGLT2) inhibitors for the treatment of type 2 diabetes", Bioorganic & Medicinal Chemistry Letters, Jun. 2, 2011, vol. 21, No. 15, pp. 4465-4470 (6 pages total).

* cited by examiner

*Primary Examiner* — Niloofar Rahmani
(74) *Attorney, Agent, or Firm* — Sughrue Mion, PLLC

(57) ABSTRACT

The present invention relates to an improved method for producing a diphenylmethane derivative which is effective as a sodium-dependent glucose cotransporter (SGLT) inhibitor, the method being carried out by means of a convergent synthesis method in which each major group is separately synthesized and then coupled. As such, in comparison to a linear synthesis method disclosed in existing documents, the synthesis pathway is compact and yield can be increased, and risk factors inherent in the linear synthesis pathway can be reduced. Furthermore, the crystal form of the compound produced according to the method has superb physicochemical characteristics, and thus can be effectively utilized in fields such as pharmaceutical manufacturing.

4 Claims, 8 Drawing Sheets

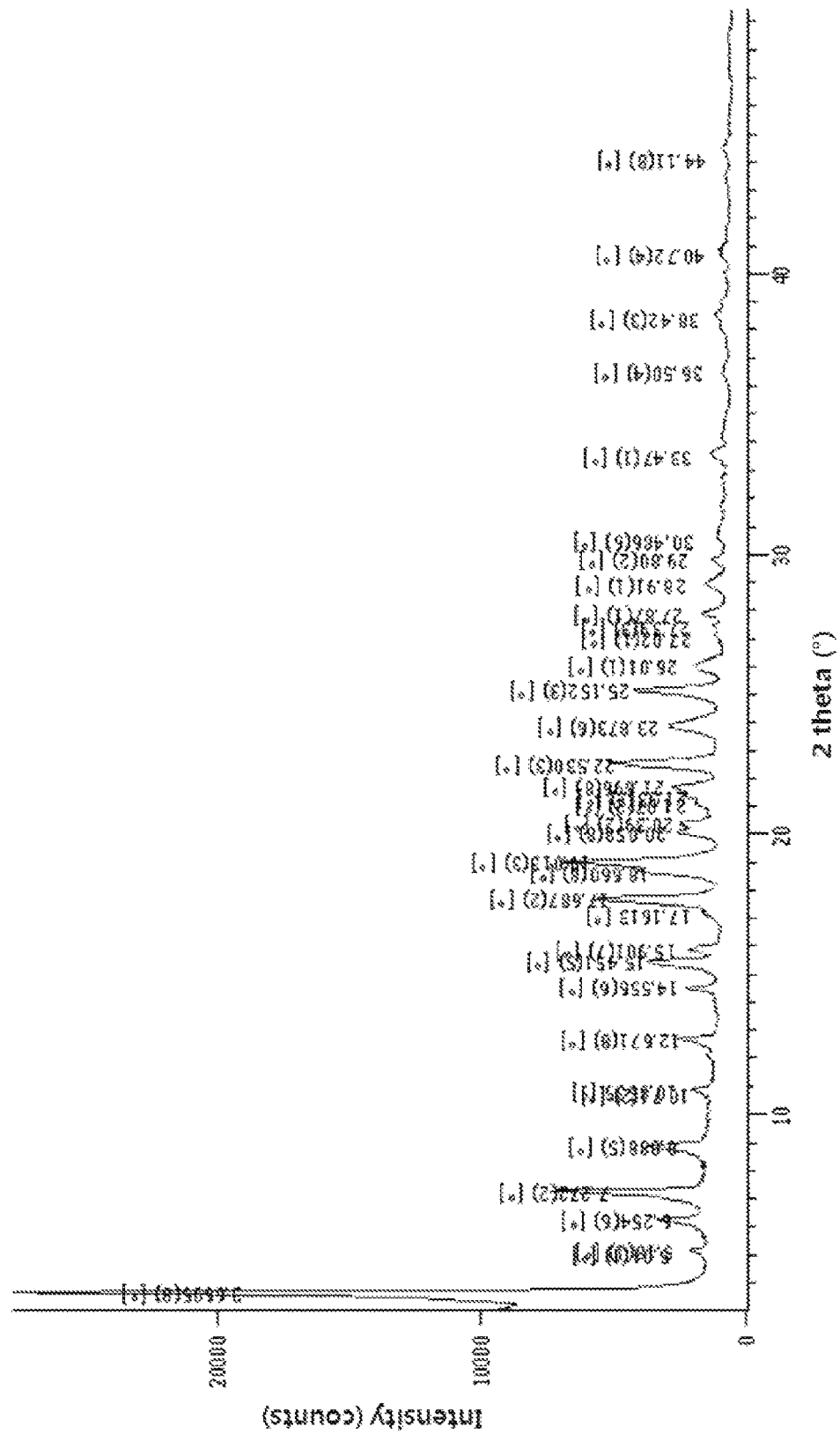
[Fig. 1]

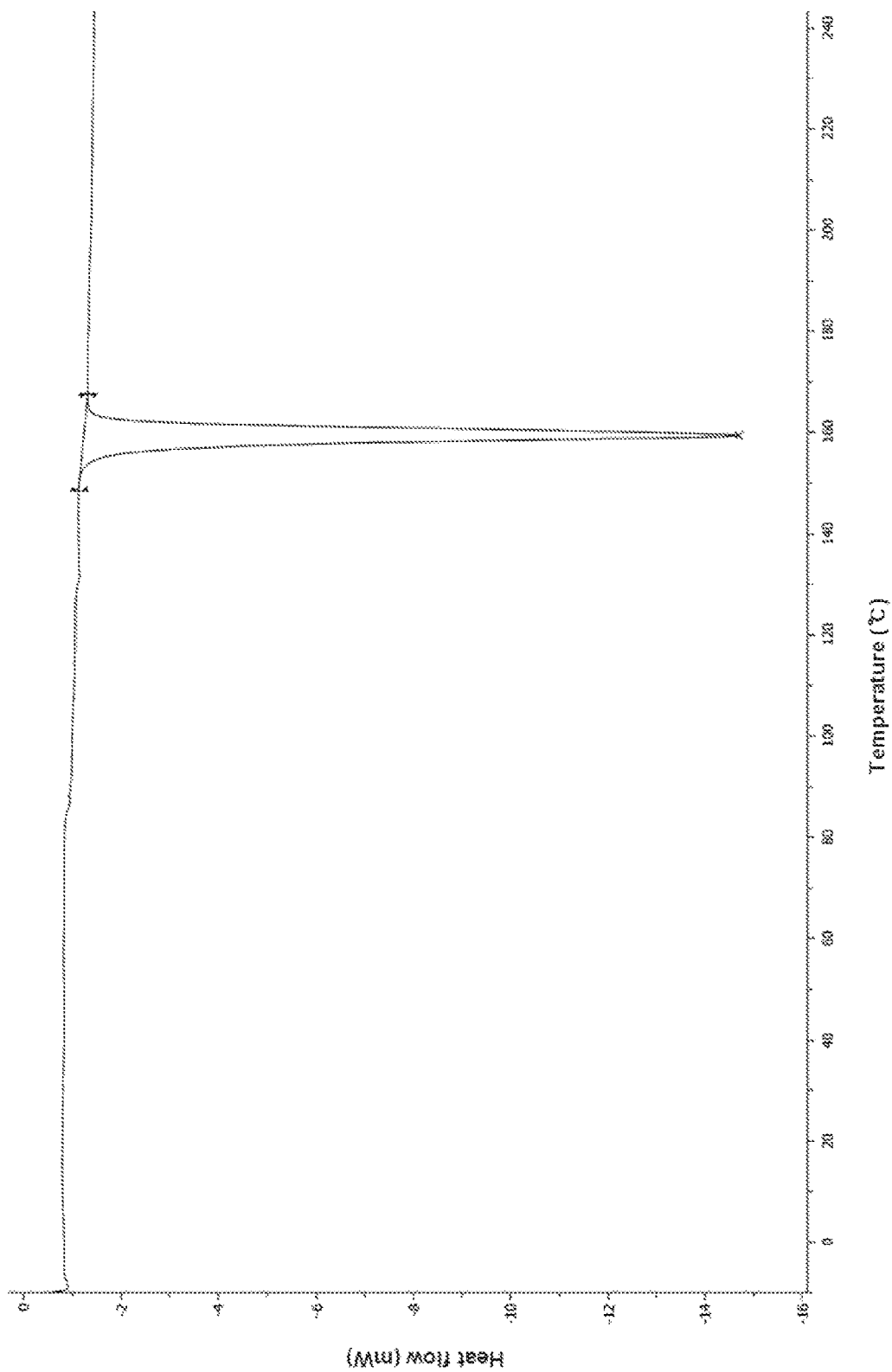
[Fig. 2]

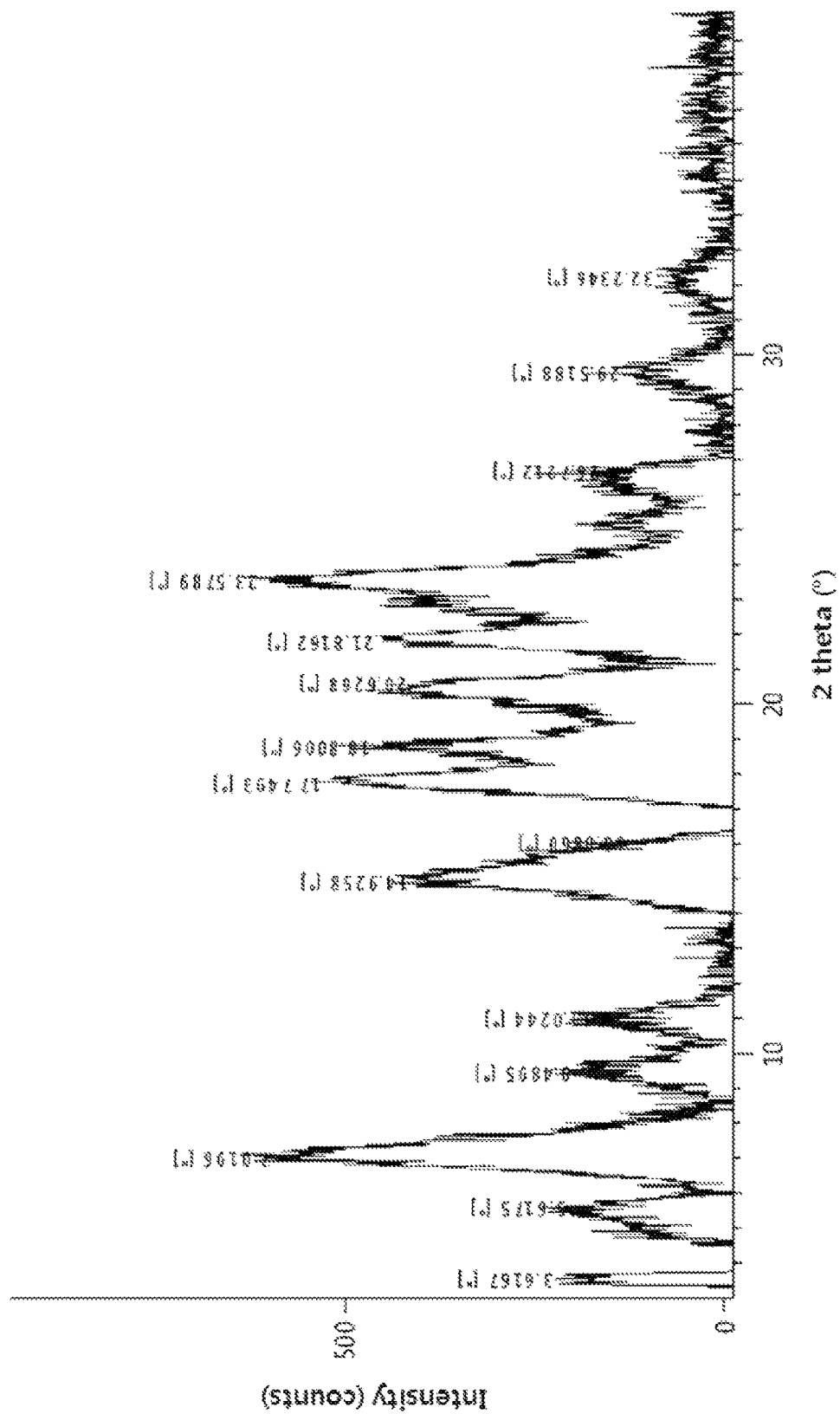
[Fig. 3]

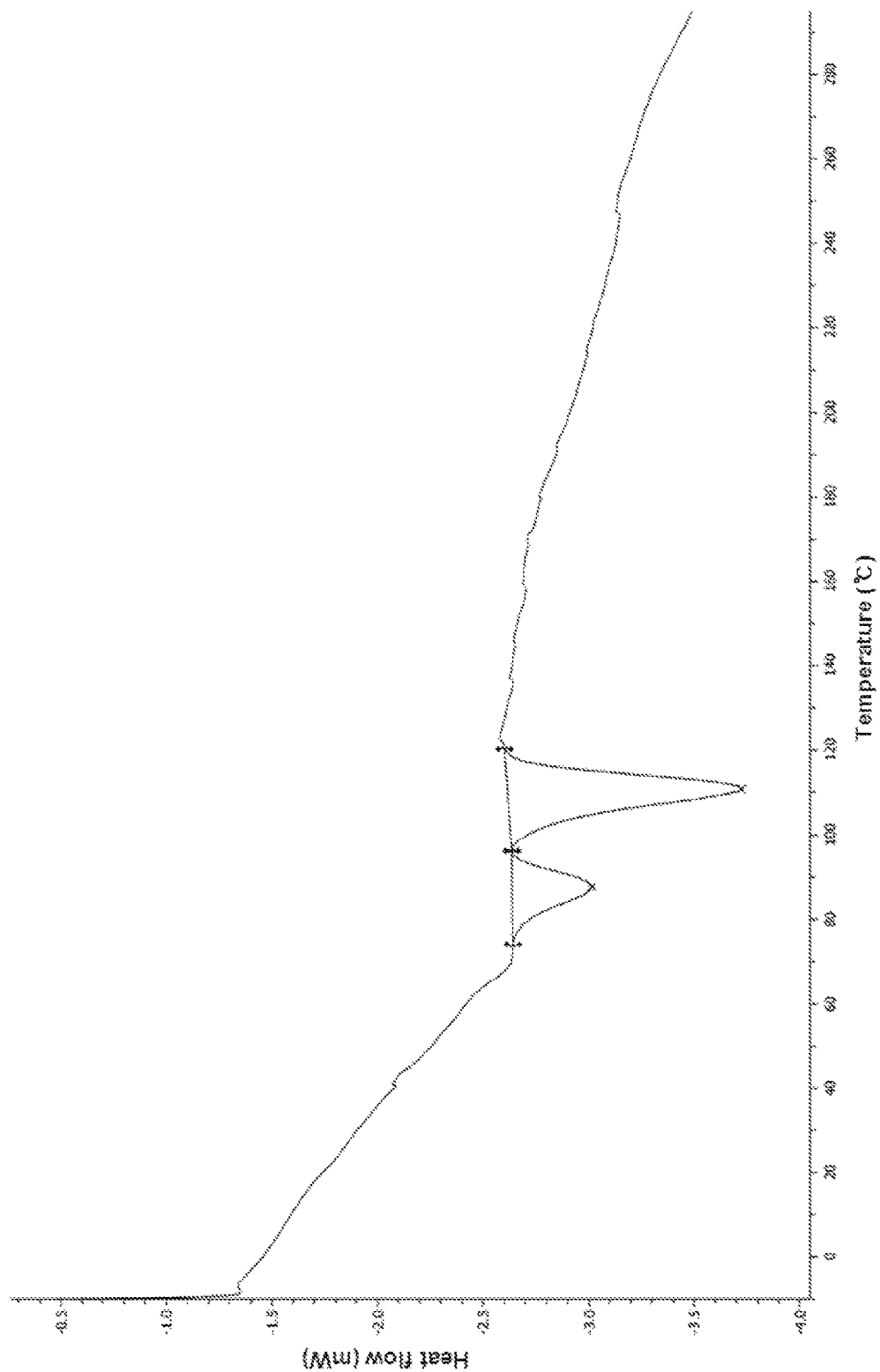
[Fig. 4]

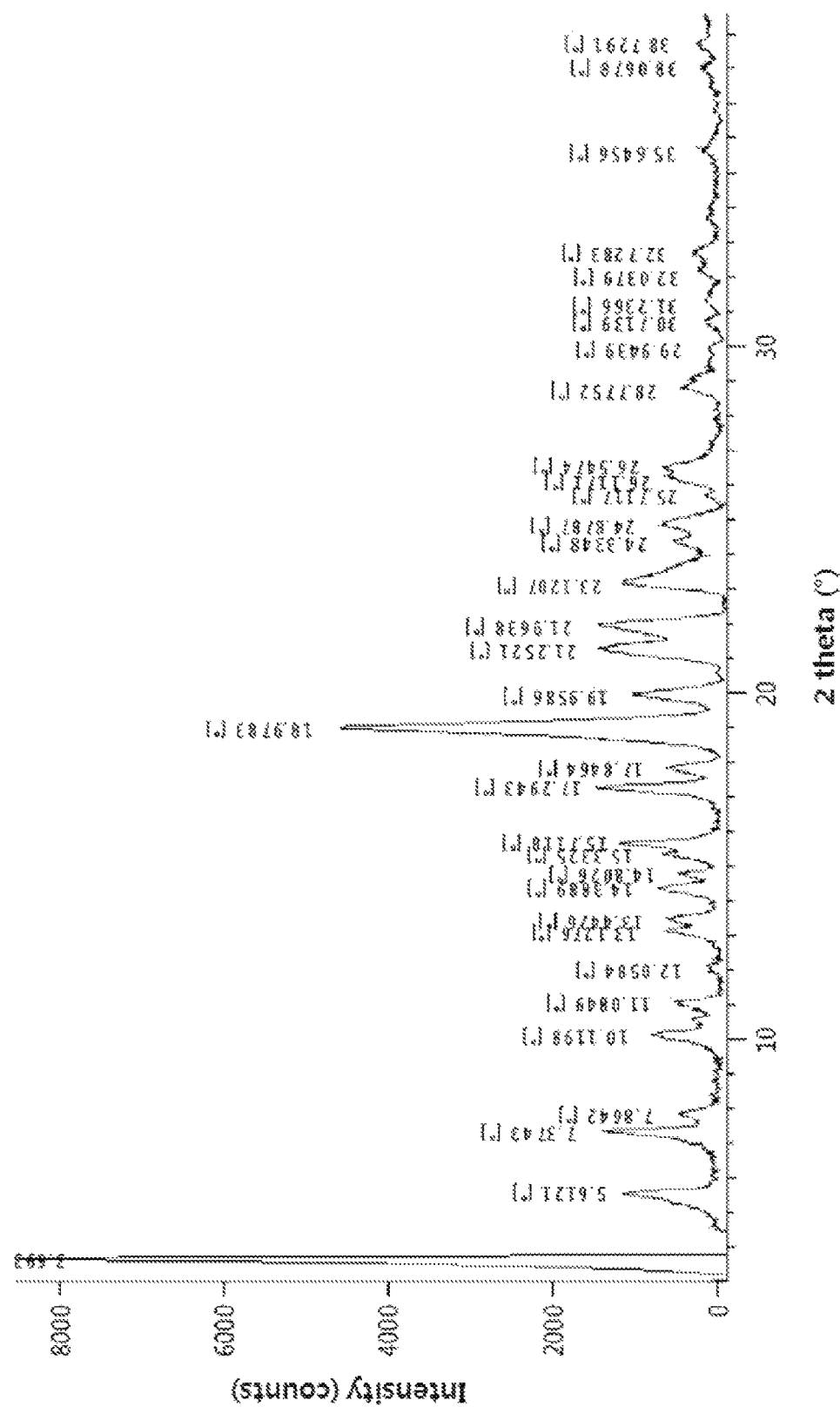

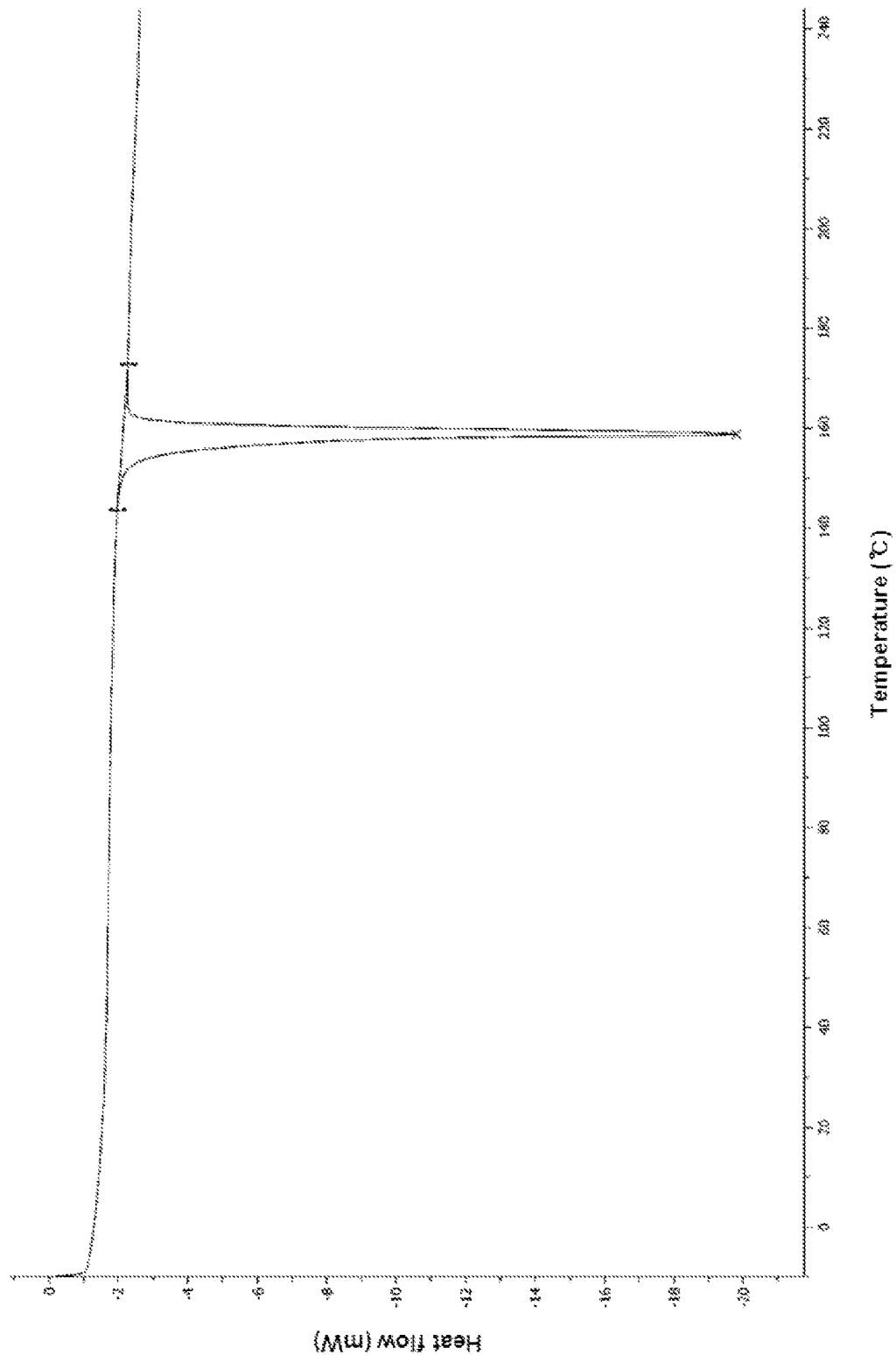
[Fig. 6]

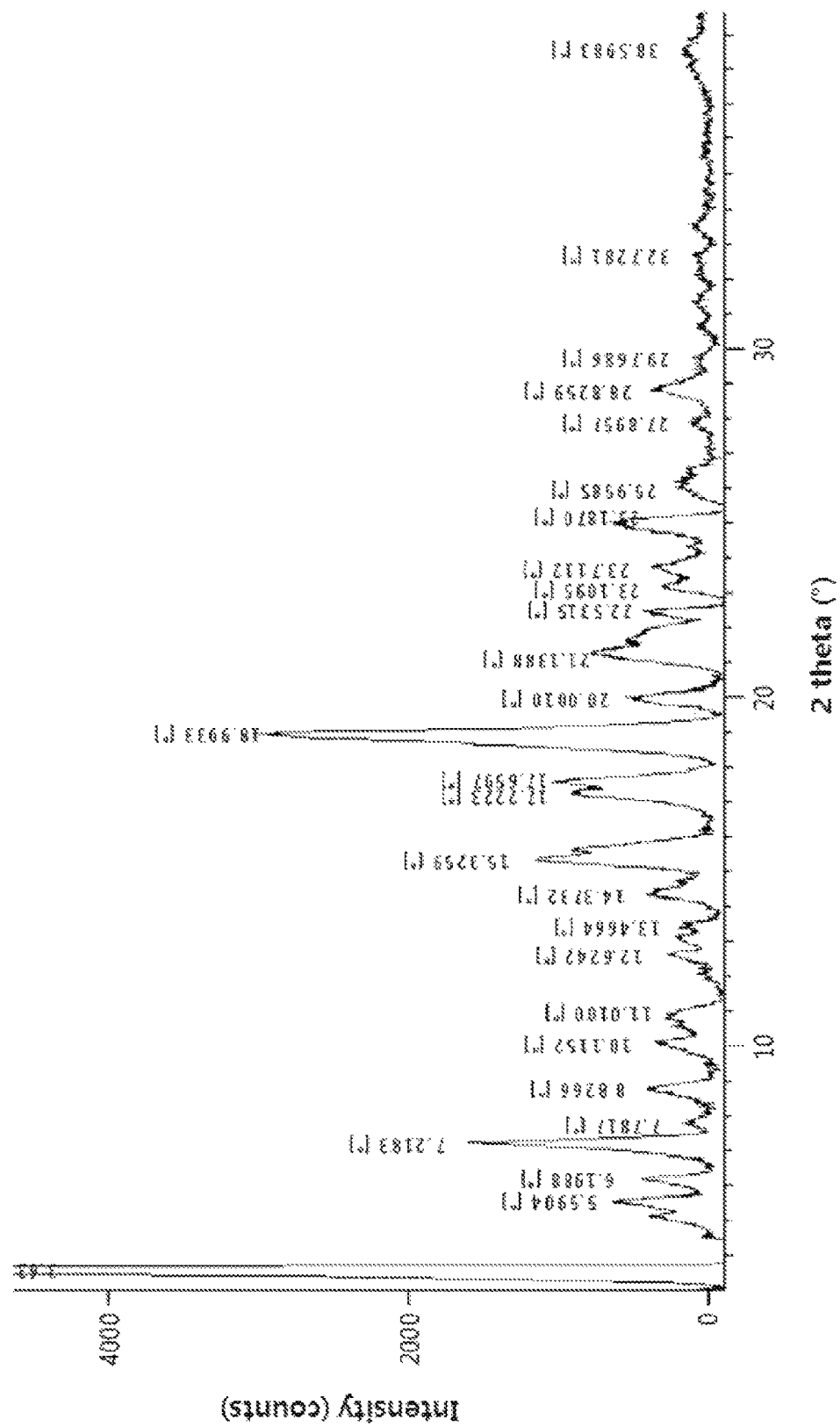
[Fig. 7]

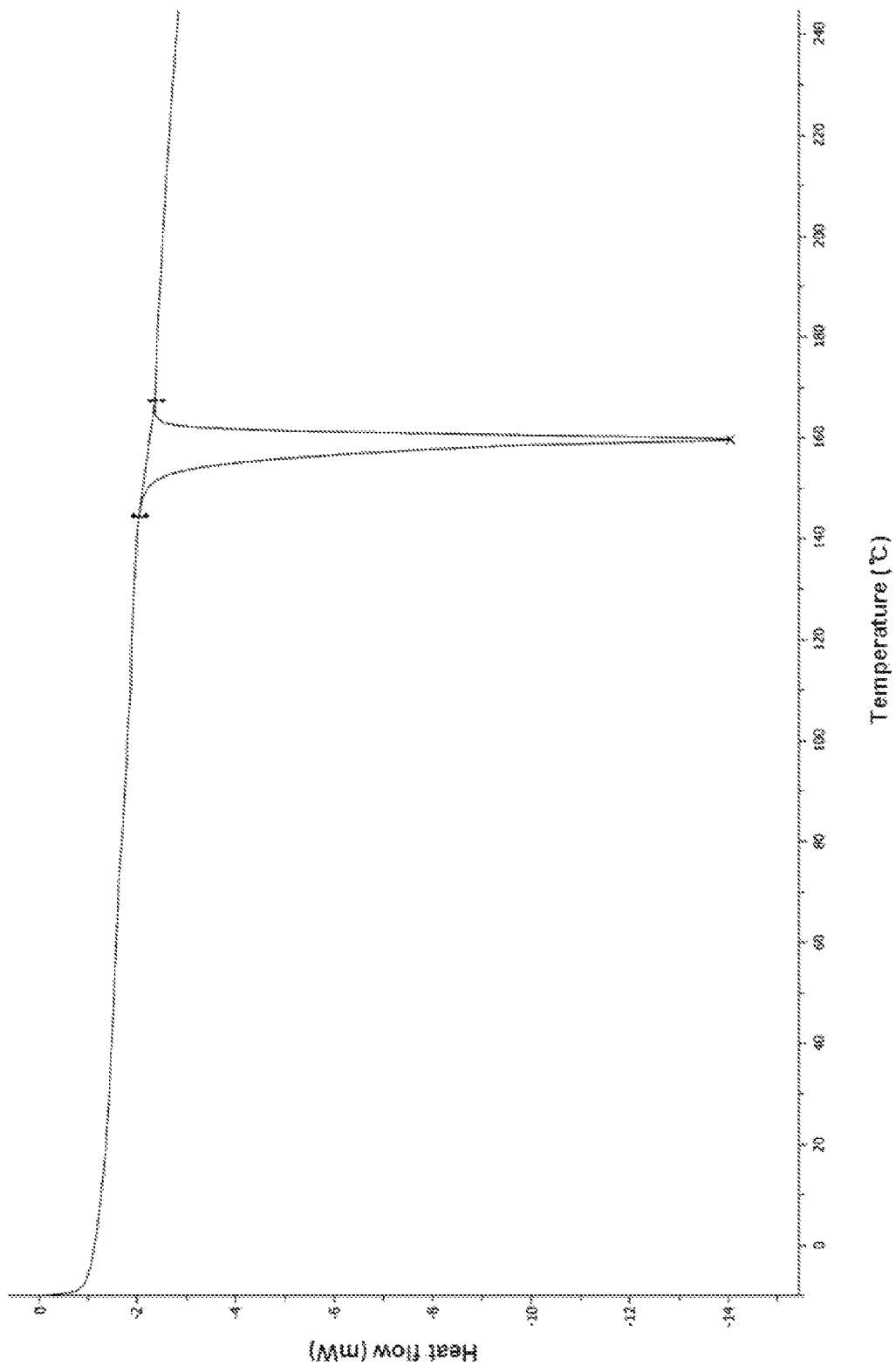

METHOD FOR PRODUCING DIPHENYLMETHANE DERIVATIVE

CROSS REFERENCE TO RELATED APPLICATIONS

This application is a National Stage of International Application No. PCT/KR2017/006271 filed Jun. 15, 2017, claiming priority based on Korean Patent Application No. 10-2016-0075910, filed Jun. 17, 2016.

TECHNICAL FIELD

The present invention relates to a method for producing a diphenylmethane derivative, and more particularly to an improved method for producing a diphenylmethane derivative which is useful as an inhibitor of a sodium-dependent glucose cotransporter (SGLT).

BACKGROUND ART

The sodium-dependent glucose cotransporter (SGLT) allows transport of $Na^+$ which goes according to concentration gradient to occur, and at the same time, allows transport of glucose which goes against concentration gradient to occur. Currently, two important SGLT isoforms have been cloned and are known as SGLT1 and SGLT2. SGLT1 is located in the intestines, kidney, and heart, and regulates cardiac glucose transport through expression thereof. Due to being a high-affinity, low-capacity transporter, SGLT1 is responsible for only a portion of renal glucose reabsorption. On the contrary, SGLT2 is a low-affinity, high-capacity transporter which is predominantly located in apical domains of epithelial cells in the early proximal convoluted tubule. In healthy individuals, over 99% of plasma glucose which is filtered in the renal glomeruli is reabsorbed, and less than 1% of total filtered glucose is excreted in the urine. It is estimated that 90% of renal glucose reabsorption is promoted by SGLT2 and the remaining 10% is mediated by SGLT1 in the late proximal straight tubule. Genetic mutation of SGLT2 does not have any particular adverse effects on carbohydrate metabolism. However, increased renal glucose secretion of about 140 g/day is caused depending on mutation. According to human mutation studies, SGLT2 has been a subject of therapeutic studies because it is estimated that SGLT2 is responsible for most renal glucose reabsorption.

US Laid-open Patent Publication No. 2015/0152075 discloses a compound having a diphenylmethane moiety which has an inhibitory activity on SGLT2, and a method for producing the same. The document discloses that the diphenylmethane derivative compound is effective for the treatment of diabetes in view of the fact that the diphenylmethane derivative compound exhibits an excellent inhibitory effect on human SGLT2 activity and significantly reduces urinary sugar excretion in animals as compared with Dapagliflozin which is well known as an SGLT2 inhibitor. In addition, US Laid-open Patent Publication No. 2014/0274918 discloses a diphenylmethane derivative which is effective as a dual inhibitor for sodium-dependent glucose cotransporter 1 (SGLT1) and sodium-dependent glucose cotransporter 2 (SGLT2).

In Example 172 of US Laid-open Patent Publication No. 2015/0152075 or the like, a method for producing a diphenylmethane compound c28 in the same manner as in the following Reaction Scheme 1 is disclosed.

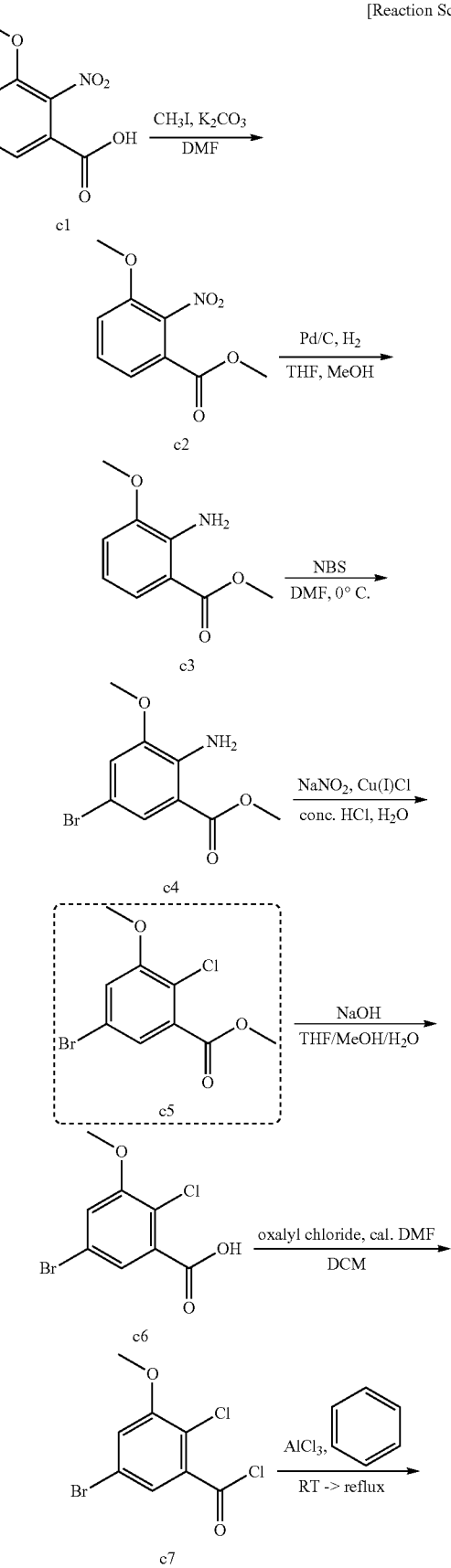

[Reaction Scheme 1]

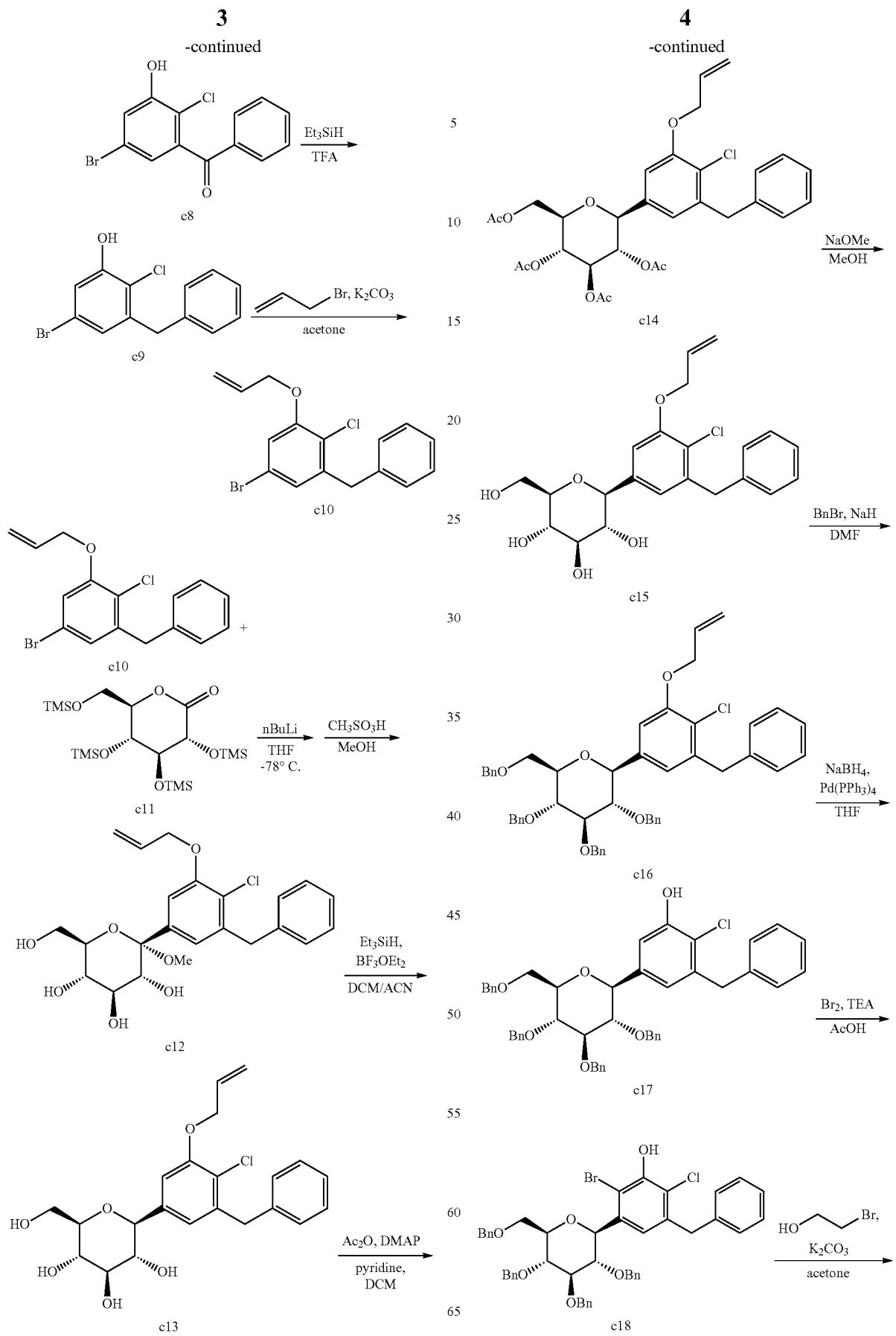

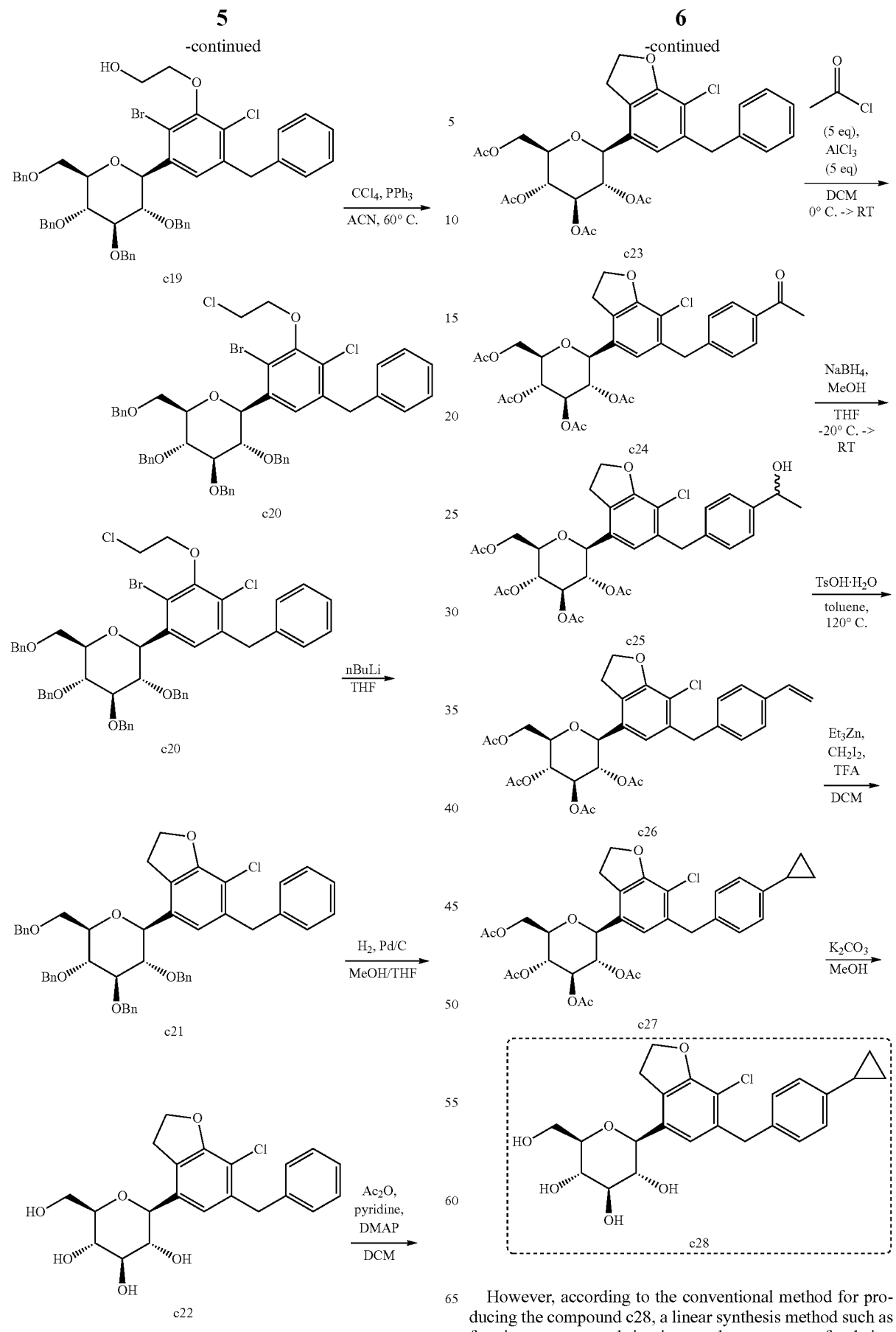
However, according to the conventional method for producing the compound c28, a linear synthesis method such as forming a pentagonal ring in an aglycone group after being coupled with a glucose group is employed. In a case of such a linear synthesis, due to a complicated pathway, a low final yield is obtained. Besides, in a case where synthesis of a substituent of the glucose group or a cyclopropylbenzyl group which is bonded to dihydrobenzofuran goes wrong in the middle, or the substituent or cyclopropylbenzyl group is intended to be changed to another, there is inconvenience of having to go through the synthesis thereof again from the beginning. In addition, even for a process of synthesizing a cyclopropyl group of the compound c28, the process is carried out by cyclizing olefin through a Simon-Smith reaction at the end of the synthesis pathway, so that a yield varies greatly depending on a state (purity, anhydrous, or the like) of a reagent (diethyl zinc, solvent) and the like, and a reaction concentration.

In view of the above, the present inventors have discovered that a diphenylmethane derivative can be produced efficiently by a convergent synthesis method in which the respective main groups are separately synthesized and then coupled to each other, rather than the conventional linear synthesis method, and therefore, have completed the present invention.

DETAILED DESCRIPTION OF INVENTION

Technical Problem

Accordingly, an object of the present invention is to provide an improved method for producing a diphenylmethane derivative which is useful as an inhibitor of SGLT.

Solution to Problem

According to an aspect of the present invention, there is provided a method for producing a compound of the following Formula 1a, the method comprising the steps of:

(1) reacting a compound of the following Formula 2 with a compound of the following Formula 3 and subjecting the resultant to a cyclization reaction, to obtain a compound of the following Formula 4;

(2) subjecting the compound of Formula 4 to aldehydation or amidation, followed by reacting the resultant with a compound of the following Formula 5 and performing reduction, to obtain a compound of the following Formula 6; and (3) reacting the compound of Formula 6 with a compound of the following Formula 7, and performing deprotection and reduction,

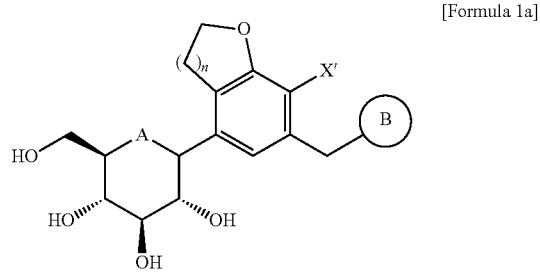
[Formula 1a]

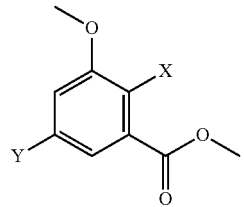
[Formula 2]

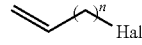
[Formula 3]

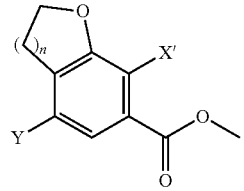
[Formula 4]

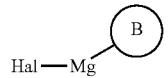
[Formula 5]

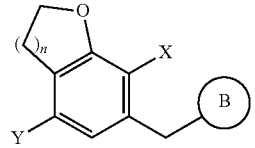
[Formula 6]

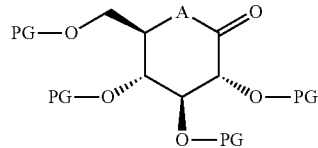
[Formula 7]

in the formulae,
A is oxygen (O) or sulfur (S);
n is 1 or 2;
PG is a protecting group;
X' is halogen or $C_{1-7}$ alkyl;
X, Y, and Hal are each independently halogen;
B is

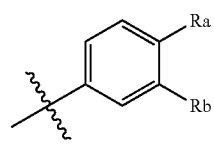
(B-1)

or

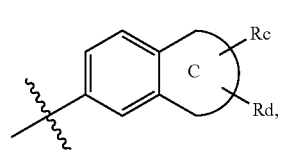
(B-2)

in which Ra, Rb, Rc, and Rd are each independently hydrogen, halogen, hydroxy, mercapto, cyano, nitro, amino, carboxy, oxo, $C_{1-7}$ alkyl, $C_{1-7}$ alkylthio, $C_{2-7}$ alkenyl, $C_{2-7}$ alkynyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{3-7}$ cycloalkylthio, $C_{5-10}$ cycloalkenyl, $C_{3-10}$ cycloalkyloxy, $C_{3-10}$ cycloalkyloxy-$C_{1-7}$ alkoxy, phenyl-$C_{1-7}$ alkyl, $C_{1-7}$ alkylthio-phenyl, phenyl-$C_{1-7}$ alkoxy, mono- or di-$C_{1-7}$ alkylamino, mono- or di-$C_{1-7}$ alkylamino-$C_{1-7}$ alkyl, $C_{1-7}$ alkanoyl, $C_{1-7}$ alkanoylamino, $C_{1-7}$ alkylcarbonyl, $C_{1-7}$ alkoxycarbonyl, carbarmoyl, mono- or di-$C_{1-7}$ alkylcarbamoyl, $C_{1-7}$ alkylsulfonylamino, phenylsulfonylamino, $C_{1-7}$ alkylsulfinyl, $C_{6-14}$ arylsulfanyl, $C_{6-14}$ arylsulfonyl, $C_{6-14}$ aryl, 5- to 13-membered heteroaryl, 5- to 10-membered heterocycloalkyl, 5- to 10-membered heterocycloalkyl-$C_{1-7}$ alkyl, or 5- to 10-membered heterocycloalkyl-$C_{1-7}$ alkoxy;

a ring C is $C_{3-10}$ cycloalkyl, $C_{5-10}$ cycloalkenyl, $C_{6-14}$ aryl, 5- to 13-membered heteroaryl, or 5- to 10-membered heterocycloalkyl;

the alkyl, alkenyl, alkynyl, and alkoxy are each independently unsubstituted, or have one or more substituents selected from the group consisting of halogen, hydroxy, cyano, nitro, amino, mercapto, $C_{1-7}$ alkyl, and $C_{2-7}$ alkynyl;

the cycloalkyl, cycloalkenyl, aryl, heteroaryl, and heterocycloalkyl are each independently unsubstituted, or have one or more substituents selected from the group consisting of halogen, hydroxy, cyano, nitro, amino, mercapto, $C_{1-4}$ alkyl, and $C_{1-4}$ alkoxy; and the heteroaryl and heterocycloalkyl each independently contain one or more heteroatoms selected from the group consisting of N, S, and O.

According to another aspect of the present invention, there is provided a method for producing a compound of the following Formula 1b, the method comprising the steps of:

(1) reacting a compound of the following Formula 2 with a compound of the following Formula 3 and subjecting the resultant to a cyclization reaction, to obtain a compound of the following Formula 4;

(2) subjecting the compound of Formula 4 to aldehydation or amidation, followed by reacting the resultant with the compound of Formula 5 and performing reduction, to obtain a compound of the following Formula 6;

(3) reacting the compound of Formula 6 with a compound of the following Formula 8 and then performing reduction, to obtain a compound of the following Formula 9;

(4) forming a furanose ring of the compound of Formula 9 into a pyranose ring under an acidic condition and then introducing a protecting group thereinto, to obtain a compound of the following Formula 10; and (5) treating the compound of Formula 10 with thiourea, reacting the resultant with $C_{1-7}$ alkyl halide, and then performing reduction,

[Formula 1b]

[Formula 2]

[Formula 3]

[Formula 4]

[Formula 5]

[Formula 6]

[Formula 8]

[Formula 9]

[Formula 10]

in the formulae,

R is $C_{1-7}$ alkylthio;

B, n, PG, X', X, Y and Hal are as defined above in Formula 1.

According to still another aspect of the present invention, there is provided a crystalline form of the compound produced by the above method, specifically a crystalline form of a compound of the following Formula c28.

[Formula c28]

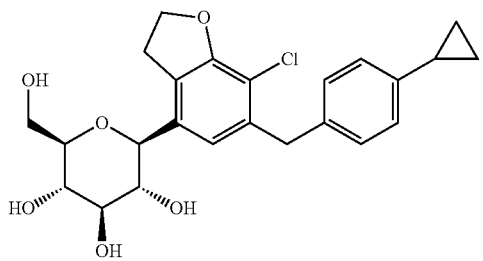

Advantageous Effects of Invention

The method for producing a diphenylmethane derivative of the present invention is carried out by a convergent synthesis method in which main groups are separately synthesized and then coupled to each other. Thus, as compared with the linear synthesis method disclosed in the prior art document, a simple synthesis pathway and a high yield can be achieved, and reproducibility is improved due to the fact that risk factors (such as returning to a first place in the pathway and repeating the synthesis at the time of failure in the middle of the synthesis) which are inherent in the linear synthesis pathway can be reduced.

In particular, according to the method disclosed in the prior art document, residues of the aglycone group have to be synthesized even after coupling the glucose group with the aglycone group. On the other hand, according to the present invention, all residues of the aglycone group can be formed before being coupled with the glucose group. In addition, an aryl group bonded to a terminal group of the aglycone can be easily synthesized, so that various designs of the terminal group are possible.

In addition, a crystalline form of the compound produced by the above method is excellent in physicochemical properties, and thus can be usefully utilized in fields such as production of pharmaceuticals.

BRIEF DESCRIPTION OF DRAWINGS

FIGS. 1 and 2 illustrate XRD and DSC spectra of a crystalline form A obtained in Experimental Example 4, respectively.

FIGS. 3 and 4 illustrate XRD and DSC spectra of a crystalline form B obtained in Experimental Example 4, respectively.

FIGS. 5 and 6 illustrate XRD and DSC spectra of a crystalline form C obtained in Experimental Example 4, respectively.

FIGS. 7 and 8 illustrate XRD and DSC spectra of a crystalline form D obtained in Experimental Example 4, respectively.

BEST MODE FOR CARRYING OUT INVENTION

The present invention relates to a process for producing a compound of Formula 1:

[Formula 1]

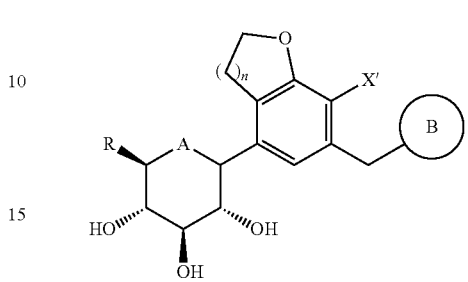

In the formula,
A is oxygen (O) or sulfur (S);
R is hydroxymethyl or $C_{1-7}$ alkylthio;
n is 1 or 2;
X' is halogen (for example, F, Cl, Br, or I) or $C_{1-7}$ alkyl;
B is

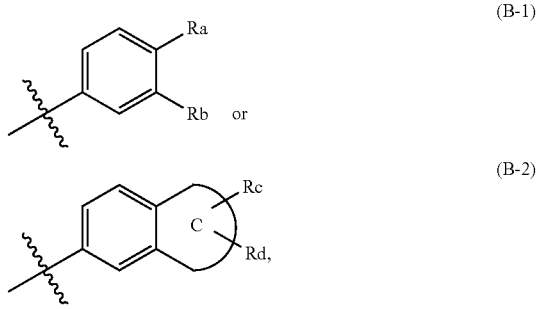

in which Ra, Rb, Rc, and Rd are each independently hydrogen, halogen, hydroxy, mercapto, cyano, nitro, amino, carboxy, oxo, $C_{1-7}$ alkyl, $C_{1-7}$ alkylthio, $C_{2-7}$ alkenyl, $C_{2-7}$ alkynyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{3-7}$ cycloalkylthio, $C_{5-10}$ cycloalkenyl, $C_{3-10}$ cycloalkyloxy, $C_{3-10}$ cycloalkyloxy-$C_{1-7}$ alkoxy, phenyl-$C_{1-7}$ alkyl, $C_{1-7}$ alkylthio-phenyl, phenyl-$C_{1-7}$ alkoxy, mono- or di-$C_{1-7}$ alkylamino, mono- or di-$C_{1-7}$ alkylamino-$C_{1-7}$ alkyl, $C_{1-7}$ alkanoyl, $C_{1-7}$ alkanoylamino, $C_{1-7}$ alkylcarbonyl, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfinyl, $C_{6-14}$ arylsulfanyl, $C_{6-14}$ arylsulfonyl, $C_{6-14}$ aryl, 5- to 13-membered heteroaryl, 5- to 10-membered heterocycloalkyl, 5- to 10-membered heterocycloalkyl-$C_{1-7}$ alkyl, or 5- to 10-membered heterocycloalkyl-$C_{1-7}$ alkoxy;
a ring C is $C_{3-10}$ cycloalkyl, $C_{5-10}$ cycloalkenyl, $C_{6-14}$ aryl, 5- to 13-membered heteroaryl, or 5- to 10-membered heterocycloalkyl;
the alkyl, alkenyl, alkynyl, and alkoxy are each independently unsubstituted, or have one or more substituents selected from the group consisting of halogen, hydroxy, cyano, nitro, amino, mercapto, $C_{1-7}$ alkyl, and $C_{2-7}$ alkynyl;
the cycloalkyl, cycloalkenyl, aryl, heteroaryl, and heterocycloalkyl are each independently unsubstituted, or have one or more substituents selected from the group consisting of halogen, hydroxy, cyano, nitro, amino, mercapto, $C_{1-4}$ alkyl, and $C_{1-4}$ alkoxy; and the heteroaryl and heterocycloalkyl each independently contain one or more heteroatoms selected from the group consisting of N, S, and O.

As a specific example, the ring B-1 may be selected from the group consisting of:

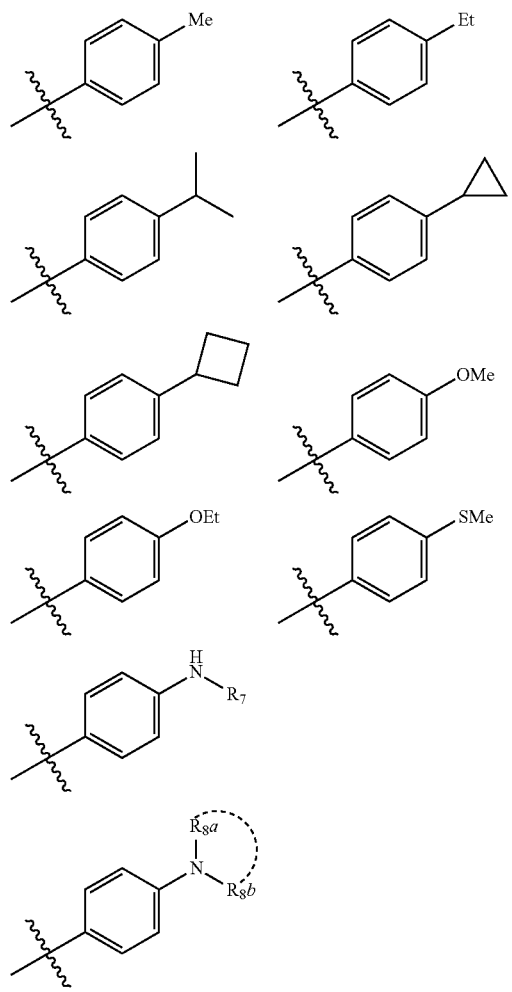

In the formulae, $R_7$ is hydrogen or $C_{1-7}$ alkyl; $R_{8a}$ and $R_{8b}$ are each independently $C_{1-7}$ alkyl or are connected to each other to form 5- to 10-membered heterocycloalkyl (which contains at least one heteroatom selected from the group consisting of N, S, and O).

As another specific example, the ring B-2 may be selected from the group consisting of:

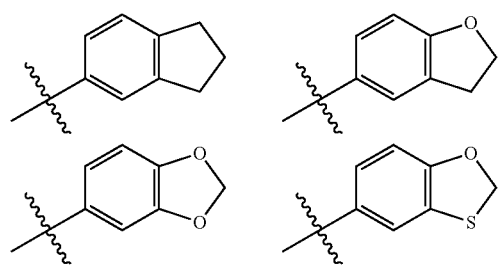
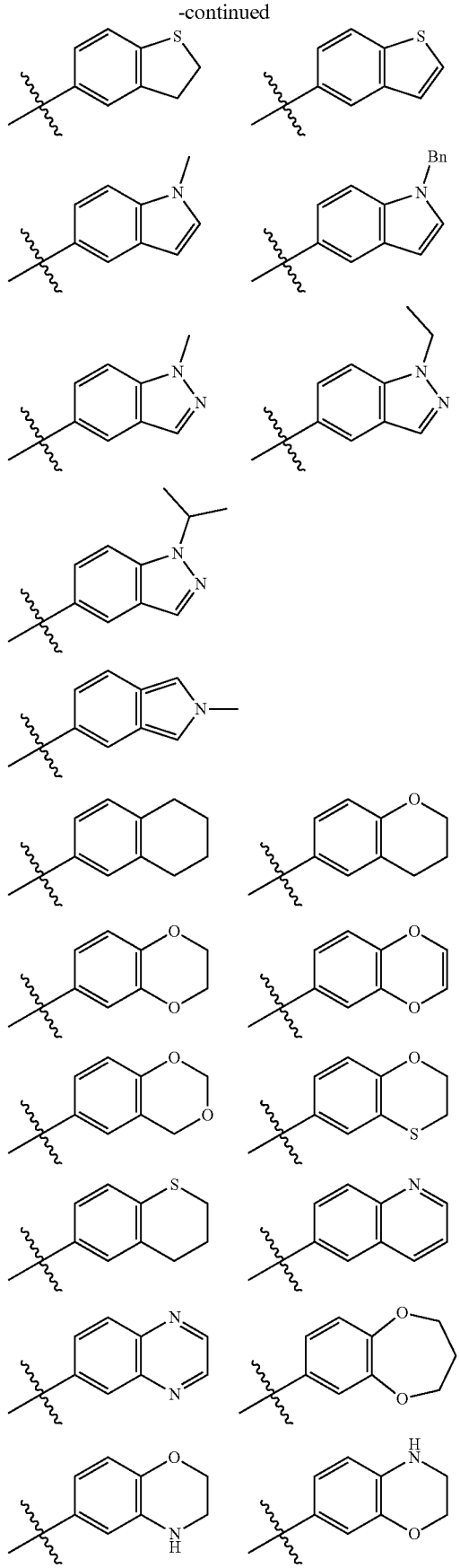

-continued

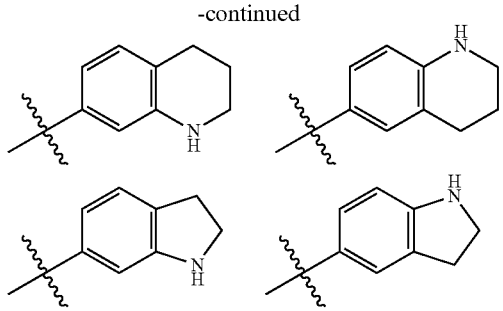

Preferably, the compound of Formula 1 may be a compound represented by the following Formula 1a or a compound represented by the following Formula 1b:

[Formula 1a]

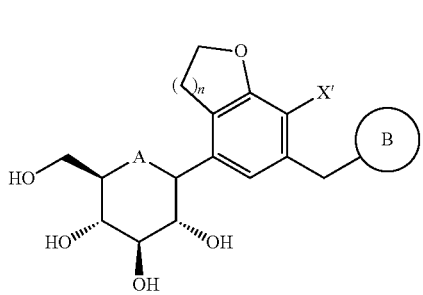

[Formula 1b]

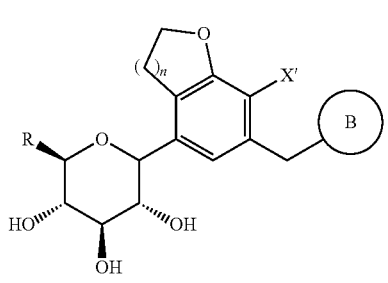

In the formulae, A, B, R, X', and n are as defined above in Formula 1.

According to a preferred example of the compound of Formula 1a, A may be oxygen; n may be 1; X' may be halogen; and B may be phenyl which is unsubstituted or substituted with one or two substituents selected from the group consisting of halogen, hydroxy, cyano, nitro, amino, mercapto, $C_{1-7}$ alkyl, $C_{3-10}$ cycloalkyl, and $C_{1-7}$ alkoxy.

In addition, the compounds of Formulae 1a and 1b may be compounds in which the glucose is in an α-form, a β-form, or a racemic form thereof.

Preferably, the compounds of Formulae 1a and 1b may be compounds in which the glucose is in a β-form.

Method for Producing Compound of Formula 1a (Formula 1 in which R=Hydroxymethyl)

According to an aspect of the present invention, there is provided a method for producing the compound of Formula 1a (Formula 1 in which R=hydroxymethyl), the method comprising the following steps of:

(1) reacting a compound of the following Formula 2 with a compound of the following Formula 3 and subjecting the resultant to a cyclization reaction, to obtain a compound of the following Formula 4;

(2) subjecting the compound of Formula 4 to aldehydation or amidation, followed by reacting the resultant with the compound of Formula 5 and performing reduction, to obtain a compound of the following Formula 6; and (3) reacting the compound of Formula 6 with a compound of the following Formula 7, and performing deprotection and reduction.

[Formula 1a]

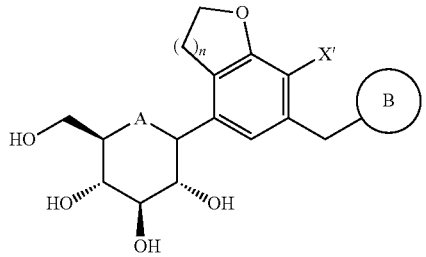

[Formula 2]

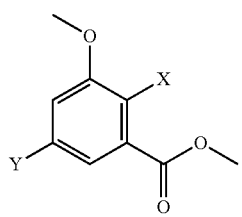

[Formula 3]

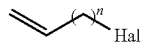

[Formula 4]

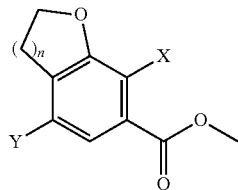

[Formula 5]

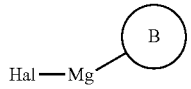

[Formula 6]

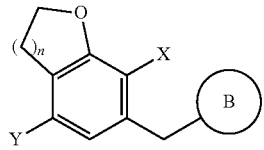

[Formula 7]

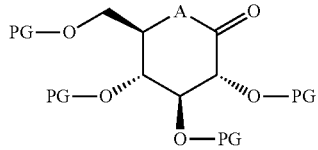

In the formulae,
A is oxygen (O) or sulfur (S);
n is 1 or 2;
PG is a protecting group;
X' is halogen or $C_{1-7}$ alkyl;
X, Y, and Hal are each independently halogen; and
B is as defined above in Formula 1.

The compound of Formula 2 used as a starting material in the above production method can be produced by the synthetic pathway published in the prior art document (US Laid-open Patent Publication No. 2015/0152075 A1). For example, the compound of Formula 2 can be produced by comprising the following steps of:

(i) subjecting the following carboxylic acid compound of Formula 2a to an esterification reaction, to obtain the following methyl ester compound of Formula 2b;

(ii) subjecting the compound of Formula 2b to a hydrogenation reaction so that the nitro group is reduced, to obtain the following amine compound of Formula 2c;

(iii) reacting the compound of Formula 2c with a halogenating reagent to obtain the following halogenated compound of Formula 2d; and (iv) subjecting the compound of Formula 2d to a Sandmeyer reaction.

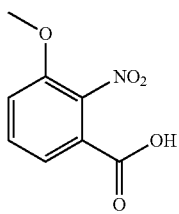

[Formula 2a]

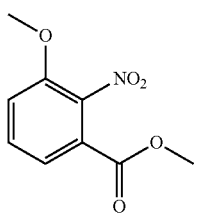

[Formula 2b]

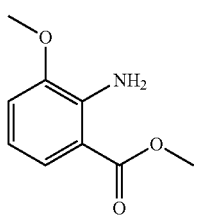

[Formula 2c]

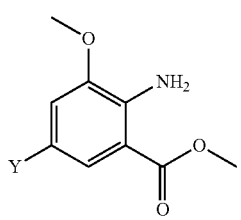

[Formula 2d]

In the formulae, Y is halogen.

As used herein, the term "halogen" means fluorine (F), chlorine (Cl), bromine (Br), or iodine (I).

Step (1)

In the step (1), the compound of Formula 2 is reacted with the compound of Formula 3 and the resultant is subjected to a cyclization reaction, to obtain the compound of Formula 4.

Thus, before being coupled with the glucose group, and also before forming a terminal residue (that is, ring B) of the aglycone group, a pentagonal or hexagonal ring in which oxygen is contained in the aglycone group can be formed in advance.

As a specific example, the step (1) can include the steps of:

(i) reacting the compound of Formula 2 with the compound of Formula 3 to obtain a compound of the following Formula 3a;

(ii) subjecting an allyl group of the compound of Formula 3a to a rearrangement reaction and subjecting the resultant to an oxidation or ozonation reaction followed by performing reduction, to obtain a compound of the following Formula 3d; and (iii) subjecting the compound of Formula 3d to a cyclization reaction, to obtain the compound of Formula 4:

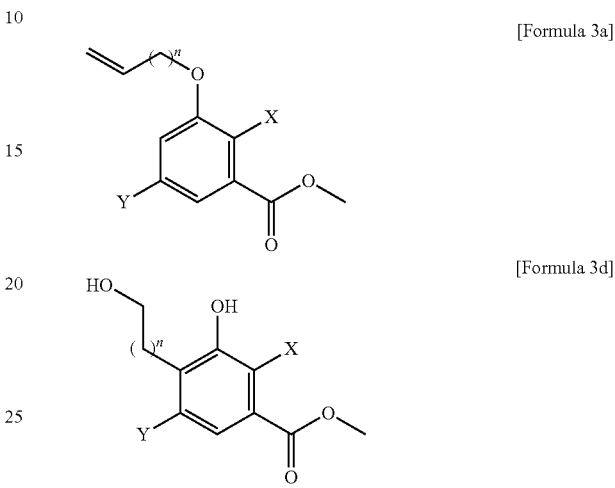

[Formula 3a]

[Formula 3d]

In the formulae, n is 1 or 2; and X and Y are each independently halogen.

In the step (i), the compound of Formula 2 may be subjected to a demethylation step before being reacted with the compound of Formula 3. For example, the compound of Formula 2 may be subjected to demethylation to obtain a compound of the following Formula 2e, and the compound of Formula 2e may be reacted with the compound of Formula 3:

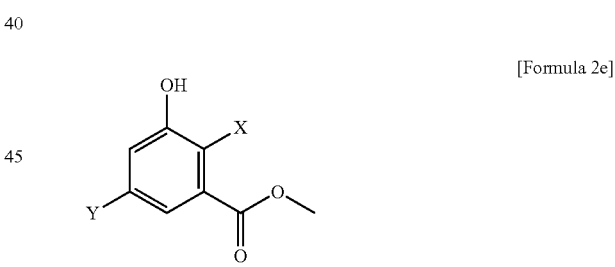

[Formula 2e]

In the formula, X and Y are each independently halogen.

The rearrangement reaction in the step (ii) may be carried out, for example, in a claisen rearrangement reaction.

The rearrangement reaction may be carried out by adding Lewis acid. The Lewis acid may be at least one selected from the group consisting of diisobutylaluminum chloride, diethylaluminum chloride, aluminum chloride, and boron trichloride.

In addition, the rearrangement reaction may be carried out in a solvent-free reaction, or under a heating condition at a high temperature (for example, 150° C. to 170° C.) in diethylamine.

After being subjected to the rearrangement reaction in the step (ii), the compound of Formula 3a can be obtained as a compound of the following Formula 3b:

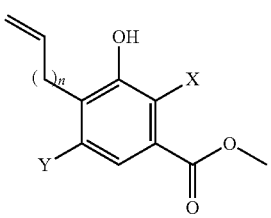

[Formula 3b]

In the formula, n is 1 or 2; and X and Y are each independently halogen.

The oxidation or ozonation reaction in the step (ii) may be carried out by adding osmium tetroxide ($OsO_4$), potassium osmate (VI) dihydrate, or ozone ($O_3$).

After being subjected to the oxidation or ozonation reaction in the step (ii), the compound of Formula 3b can be obtained as a compound of the following Formula 3c:

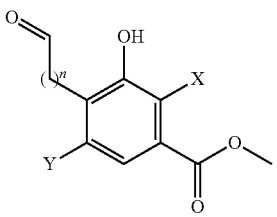

[Formula 3c]

In the formula, n is 1 or 2; and X and Y are each independently halogen.

Then, the compound of Formula 3c can be reduced to obtain the compound of Formula 3d.

In the step (iii), the compound of Formula 3d can be subjected to the cyclization reaction, to obtain the compound of Formula 4. According to such a method, a yield can be improved as compared with the cyclization method disclosed in the prior art document (US Laid-open Patent Publication No. 2015/0152075 A1).

The cyclization reaction may be a cyclization reaction using a Vilsmeier reagent, a cyclization reaction using a leaving group, a cyclization reaction using a halide, or a cyclization reaction using a Mitsunobu reaction.

According to an example, the cyclization reaction may be carried out by adding a Vilsmeier reagent to the compound of Formula 3d. The reaction at this time may be carried out at a temperature of 0° C. to normal temperature. It is preferable in terms of yield that the above-mentioned Vilsmeier reagent is immediately produced at the time of synthesis and used, and for example, a Vilsmeier reagent produced by a reaction of dimethylformamide (DMF) with $SOCl_2$ or $POCl_3$ may be used.

According to another example, the cyclization reaction may be carried out by introducing a tosyl group or a mesyl group as a leaving group. According to still another example, the cyclization reaction may be carried out using a halide such as $I_2$ and $PBr_3$. According to yet another example, the cyclization reaction may also be carried out through a Mitsunobu reaction using diisopropyl azodicarboxylate (DIAD) or the like.

These reactions are reactions in which a primary alcohol group is substituted with a group capable of acting as a leaving group and the substituted group acts as a nucleophile to the phenol group so that a cyclization reaction occurs.

Step (2)

In the step (2), the compound of Formula 4 is subjected to aldehydation or amidation, and then reacted with the compound of Formula 5. The resultant is reduced to obtain the compound of Formula 6.

As an example, the step (2) may include subjecting the compound of Formula 4 to aldehydation, to obtain a compound of the following Formula 4a, and then reacting the compound of Formula 4a with the compound of Formula 5:

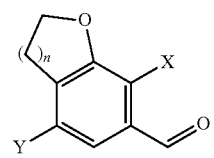

[Formula 4a]

In the formula, n is 1 or 2; and X and Y are each independently halogen.

Specifically, the aldehydation reaction can be carried out by reducing the compound of Formula 4 to obtain a compound of the following Formula 4c, followed by reacting the compound of Formula 4 with pyridinium chlorochromate (PCC), magnesium dioxide, sulfur trioxide pyridine complex, or the like. As a result, the compound of Formula 4a can be obtained:

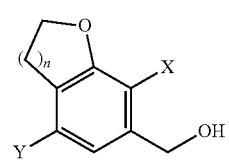

[Formula 4c]

In the formula, n is 1 or 2; and X and Y are each independently halogen.

At this time, a reducing agent such as $NaBH_4$ and $LiBH_4$ may be used at the time of reducing the compound of Formula 4. In addition, at the time of the reduction, alcohol, tetrahydrofuran (THF), or a mixture thereof may be used as a solvent. As a preferred example, at the time of the reduction, a mixed solvent of ethanol and THF may be used, and a mixing volume ratio thereof may be 1:1 to 1:3. In addition, at the time of the reduction, Lewis acid may be further used, and examples of the Lewis acid that can be used include LiCl and $CaCl_2$.

Then, the compound of Formula 4a can be reacted with the compound of Formula 5 to obtain a compound of the following Formula 6a:

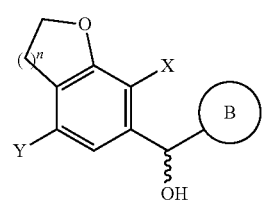

[Formula 6a]

In the formula, n is 1 or 2, X and Y are each independently halogen, and B is as defined above in Formula 1.

The compound of Formula 6a can be reduced to obtain the compound of Formula 6.

As another example, the step (2) may include subjecting the compound of Formula 4 to amidation, to obtain a compound of the following Formula 4b, and then reacting the compound of Formula 4b with the compound of Formula 5:

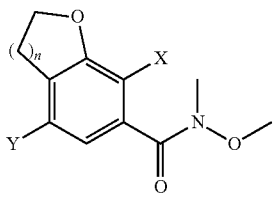

[Formula 4b]

In the formula, n is 1 or 2; and X and Y are each independently halogen.

Specifically, the amidation reaction can be carried out by subjecting the compound of Formula 4 to hydrolyzation, followed by reacting the resultant with N,O-dimethylhydroxyamine hydrochloride (MeO(Me)NH.HCl) or the like. As a result, a Weinreb amide form such as the Formula 4b can be obtained.

Then, the compound of Formula 4b can be reacted with the compound of Formula 5 to obtain a compound of the following Formula 6b:

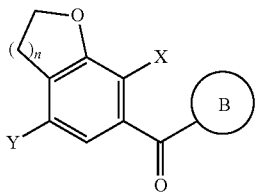

[Formula 6b]

In the formula, n is 1 or 2; X and Y are each independently halogen, and B is as defined above in Formula 1.

Then, the compound of Formula 6b can be reduced to obtain the compound of Formula 6.

The compound of Formula 5 may be a Grignard reagent.

According to a general method of producing the Grignard reagent, a compound of the following Formula 5a can be reacted with metal magnesium (Mg) to produce the compound of Formula 5.

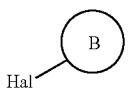

[Formula 5a]

In the formula, B is as defined above in Formula 1 and Hal is halogen.

As described above, according to the present invention, the group B of the final compound (compound of Formula 1a) can be easily introduced in advance according to a method of producing a Grignard reagent before coupling of the aglycone group with the glucose group, which not only allows various derivatization but also allows a final yield to be improved.

On the other hand, according to the prior art document (US Laid-open Patent Publication No. 2015/0152075 A1), in order to complete the group B of the final compound, after being coupled with the glucose group, a complicated synthesis process is required at the end of the synthesis pathway, and thus there is a problem that a reaction yield and a reaction reproducibility vary greatly due to a long process.

Step (3)

In the step (3), the compound of Formula 6 is reacted with the compound of Formula 7, and then deprotection and reduction are performed.

A reaction of the compound of Formula 6 with the compound of Formula 7 may be carried out in the presence of n-butyllithium, sec-butyllithium, t-butyllithium, i-propylmagnesium chloride (i-PrMgCl), or the like.

The compound of Formula 6 can be reacted with the compound of Formula 7 to obtain a compound of the following Formula 7a:

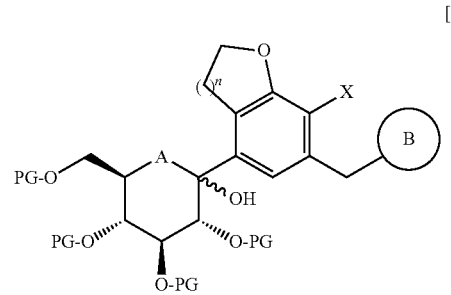

[Formula 7a]

In the formula, A is oxygen or sulfur; n is 1 or 2; X is halogen; PG is a protecting group; and B is as defined above in Formula 1.

The protecting group may be, for example, a trimethylsilyl (TMS) group, a benzyl group, or an acetyl group.

Then, the compound of Formula 7a can be deprotected to obtain the compound of Formula 1a. For example, in a case where the protecting group is a trimethylsilyl (TMS) group, the deprotection is performed by adding methanesulfonic acid ($CH_3SO_3H$) or trimethylsilyl trifluoromethane sulfonate (TMSOTf) to the compound of Formula 7a, so that the compound of Formula 1a can be obtained.

In addition, after the deprotection, reduction may be further performed to obtain the compound of Formula 1a. At this time, dichloromethane ($CH_2Cl_2$) and acetonitrile ($CH_3CN$) may be used in combination as a solvent.

The compound of Formula 1a obtained through the above steps may be a compound in which an α-form and a β-form of the glucose are mixed.

Thus, further isolation can be performed to obtain only the α-form or β-form to be desired. That is, after or during the deprotection and reduction process, it is possible to further perform isolation of only a compound in which the glucose is in a β-form.

For example, a protecting group is introduced into the compound obtained by the deprotection and reduction. Then, the resultant is heated in alcohol, ethyl acetate, or dichloromethane, and the resulting precipitate is isolated and then deprotected, so that only the β-form can be obtained.

Specifically, a hydroxy group of the glucose in the compound obtained by the deprotection and reduction is protected with an acetyl group or the like. Then, the resultant is heated and stirred in a $C_{1-6}$ alcohol solvent (ethanol, isopropanol, or the like), and the resulting precipitate is isolated, so that only a compound of the following Formula 7b in which the glucose is in a β-form can be obtained:

[Formula 7b]

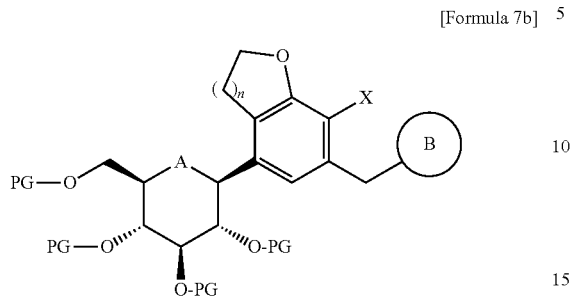

In the formula, A is oxygen or sulfur; n is 1 or 2; X is halogen; PG is a protecting group; and B is as defined above in Formula 1.

Then, the compound of Formula 7b can be deprotected to finally obtain only the β-form which can be represented by the following Formula 7c:

[Formula 7c]

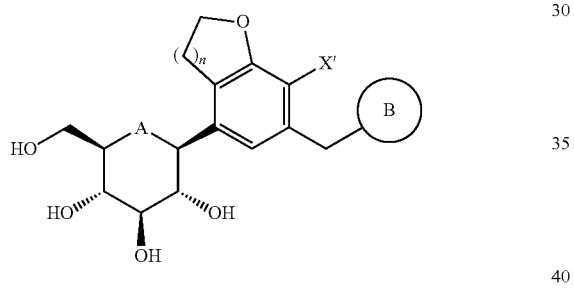

In the formula, A, B, n, and X' are as defined above in Formula 1.

According to a preferred example, the step (3) can be carried out by the method comprising the steps of:

(3a-1) reacting the compound of Formula 6 with the compound of Formula 7 in the presence of n-butyllithium, sec-butyllithium, t-butyllithium, or i-propylmagnesium chloride, to obtain a compound of the following Formula 7a;

(3a-2) subjecting the compound of Formula 7a to deprotection and methylation reactions under an acid condition in the presence of methanol, to obtain a compound of the following Formula 7d;

(3b) reducing the compound of Formula 7b to obtain a compound of the following Formula 7e; and (3c) introducing a protecting group into the compound of Formula 7e, heating the resultant in alcohol, ethyl acetate, or dichloromethane, and isolating and deprotecting the resulting precipitate, to obtain only a β-form:

[Formula 7a]

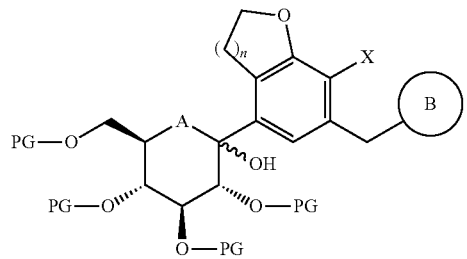

[Formula 7d]

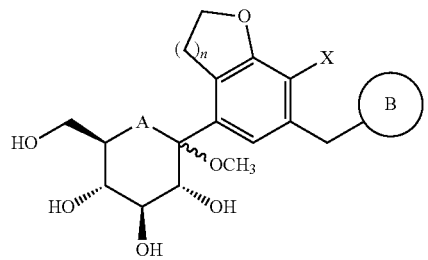

[Formula 7e]

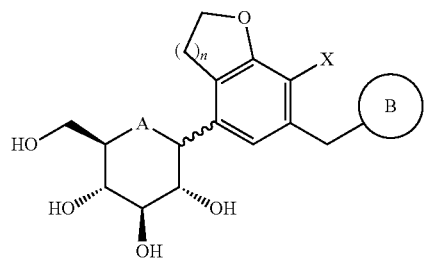

In the formulae, PG is a protecting group; and A, B, n, and X are as defined above in Formula 1a.

After the reaction in the step (3a-1), it is preferable that the compound of Formula 7a is obtained by further performing evaporation, extraction, drying, filtration, or the like, and then used in the next step (3a-2).

The acid used in the step (3a-2) may be hydrochloric acid, sulfuric acid, acetic acid, trifluoroacetic acid, methanesulfonic acid, trifluoromethanesulfonic acid, p-toluenesulfonic acid, hydrogen chloride gas, or the like.

According to another preferred example, the step (3) may be carried out by the method comprising the steps of:

(3a') reacting the compound of Formula 6 with the compound of Formula 7 in the presence of n-butyllithium, sec-butyllithium, t-butyllithium, or i-propylmagnesium chloride, and subjecting the resultant to deprotection and methylation reactions under an acid condition in the presence of methanol without a separate purification, to obtain a compound of the following Formula 7d;

(3b') reducing the compound of Formula 7d to obtain a compound of the following Formula 7e; and (3c') introducing a protecting group into the compound of Formula 7e to isolate only a β-form, and performing deprotection:

[Formula 7d]

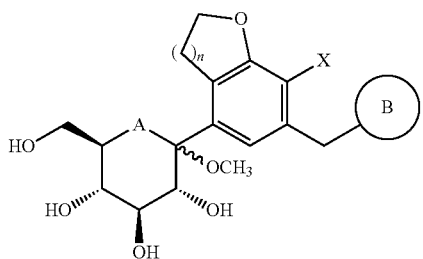

[Formula 7e]

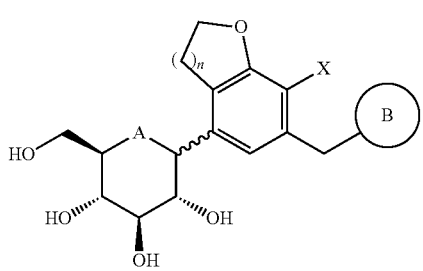

In the formulae, A, B, n, and X are as defined above in Formula 1a.

In the step (3a'), first, a binding reaction is carried out, and at this time, each of the compound of Formula 7 and the reaction reagent (that is, n-butyllithium, sec-butyllithium, t-butyllithium, or i-propylmagnesium chloride) may be used for the reaction in an amount of 1.5 to 2.5 equivalents, more preferably 1.7 to 2.3 equivalents, and particularly about 2.0 equivalents, with respect to 1 equivalent of the compound of Formula 6. The reaction at this time may be carried out at a temperature in a range of −80° C. to −10° C. and more preferably −70° C. to −60° C., for 1 to 12 hours, or for 1 to 3 hours. In addition, as a reaction solvent, a single solvent of tetrahydrofuran or ether, a mixed solvent of tetrahydrofuran/toluene (1:1), or the like may be used.

In addition, in the step (3a'), the deprotection and methylation reactions are carried out under an acid condition. Examples of the acid used at this time include hydrochloric acid, sulfuric acid, acetic acid, trifluoroacetic acid, methanesulfonic acid, trifluoromethanesulfonic acid, p-toluenesulfonic acid, and hydrogen chloride gas. The acid may be used in an amount of 2 to 5 equivalents and more preferably 3 equivalents, with respect to 1 equivalent of the compound of Formula 6. The reaction at this time may be carried out at a temperature in a range of 0° C. to 40° C. and more preferably 20° C. to 30° C., for 6 to 24 hours, or for 6 to 12 hours. As a reaction solvent, methanol or the like may be used.

Then, a reduction reaction is carried out in the step (3b'), and at this time, a reducing agent and an acid may be used. Examples of the reducing agent can include triethylsilane, triisopropylsilane, t-butyldimethylsilane, and sodium borohydride. Examples of the acid can include boron trifluoride diethylether, trimethylsilyl trifluoromethanesulfonate, aluminum chloride, trifluoroacetic acid, and trifluoromethanesulfonic acid. The reducing agent may be used in an amount of 2 to 5 equivalents and more preferably about 3 equivalents, and the acid may be used in an amount of 1.5 to 3 equivalents and more preferably about 2 equivalents. The reaction at this time may be carried out at a temperature in a range of −50° C. to 0° C. and more preferably in a range of −20° C. to −10° C., for 2 to 12 hours, or for 2 to 5 hours.

In addition, as a reaction solvent, a single solvent such as dichloromethane, 1,2-dichloroethane, or acetonitrile, or a mixed solvent such as dichloromethane/acetonitrile (1:1) and 1,2-dichloromethane/acetonitrile (1:1) may be used.

Next, a protecting group is introduced in the step (3c'), and at this time, a reaction using an acetylating agent and a base may be carried out. Examples of the acetylating agent include acetyl chloride, acetyl bromide, and acetic anhydride, and examples of the base include sodium hydroxide, sodium carbonate, triethylamine, diisopropylethylamine, pyridine, lutidine, and 4-dimethylaminopyridine. The acetylating agent may be used in an amount of 4 to 12 equivalents and more preferably about 8 equivalents, and the base may be used in an amount of 1 to 4 equivalents and more preferably about 1.5 equivalents. The reaction at this time may be carried out at a temperature in a range of 0° C. to 50° C. and more preferably 20° C. to 30° C., for 1 to 12 hours, or for 1 to 3 hours. As a reaction solvent, acetone, ethyl acetate, tetrahydrofuran, dimethylformamide, dimethylacetamide, dichloromethane, 1,2-dichloroethane, chloroform, or the like may be used.

Finally, a deprotection reaction is carried out in the step (3c'), and at this time, a reagent such as lithium hydroxide, sodium hydroxide, potassium hydroxide, sodium methoxide, and sodium ethoxide may be used in an amount of 2 to 12 equivalents and more preferably about 5 equivalents. The reaction at the time may be carried out at a temperature in a range of 0° C. to 50° C. and more preferably 20° C. to 30° C., for 1 to 12 hours, or for 1 to 3 hours. As a reaction solvent, methanol/water (1:1 to 3:1), dichloromethane/methanol (1:1 to 1:2), dichloromethane/ethanol (1:1 to 1:2), tetrahydrofuran/methanol (1:1 to 1:2), tetrahydrofuran/ethanol (1:1 to 1:2), tetrahydrofuran/methanol/water (1:1:3 to 2:1:3), tetrahydrofuran/ethanol/water (1:1:3 to 2:1:3), or the like may be used.

According to still another preferred example, the step (3) may be carried out by the method comprising the steps of:

(3a") reacting the compound of Formula 6 with the compound of Formula 7 in the presence of n-butyllithium, sec-butyllithium, t-butyllithium, or i-propylmagnesium chloride, and subjecting the resultant to deprotection and methylation reactions under an acid condition in the presence of methanol without a separate purification, to obtain a compound of the following Formula 7d;

(3b") introducing a protecting group into the compound of Formula 7d to obtain a compound of the following Formula 7f; and (3c") isolating only a β-form of the compound of Formula 7f and performing reduction, and then performing deprotection:

[Formula 7d]

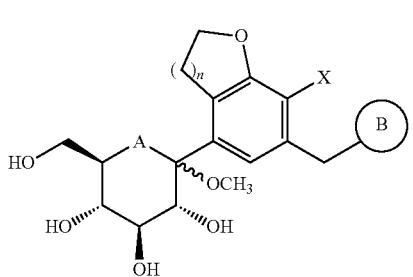

[Formula 7f]

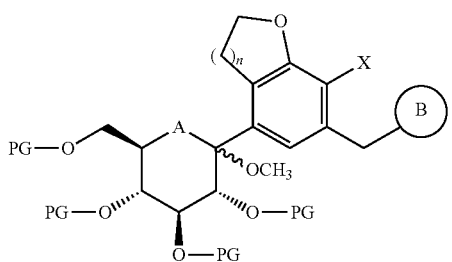

In the formulae, PG is a protecting group; and A, B, n, and X are as defined above in Formula 1a.

In the step (3a″), the binding reaction, the deprotection, and the methylation are carried out. Preferred conditions at this time such as an equivalent ratio, a reaction temperature, and a solvent are as exemplified in the step (3a′).

Then, a protecting group is introduced in the step (3b″), and at this time, a reaction using an acetylating agent and a base may be carried out. Preferred conditions such as a type of the acetylating agent, a type of the base, an equivalence ratio, a reaction temperature, and a solvent are as exemplified above in the step (3c′).

Next, a reduction reaction is carried out in the step (3c″). At this time, a reducing agent and an acid may be used, and preferred conditions such as a type of the reducing agent, a type of the acid, an equivalence ratio, a reaction temperature, and a solvent are as exemplified above in the step (3b′).

In addition, a deprotection reaction is performed in the step (3c″), and preferred conditions at this time such as a type of a reagent, an equivalence ratio, a reaction temperature, and a solvent are as exemplified above in the step (3c′).

As shown in the above-mentioned preferred exemplifications, a process of obtaining the compound of Formula 7d may be carried out in two steps, or may be carried out in one step as an in-situ reaction so that a final yield is further improved. In addition, in a case of being carried out in one step as an in-situ reaction, a crude concentrated residue containing the compound of Formula 7b may be obtained, or the compound of Formula 7d may be obtained therefrom as a solid content via crystallization and used in the next step. In the latter case, it is possible to easily achieve improvement in quality and control of moisture content through removal of reaction by-products.

In addition, the compound of Formula 7d may be used in the next step through purification after synthesis thereof. For example, (i) after being synthesized, the compound of Formula 7d may be caused to form an azeotropic mixture with an organic solvent such as toluene, and the residue obtained by repeating a concentration process to remove residual moisture may be used in the next step, or (ii) after being synthesized, the compound of Formula 7d may be subjected to crystallization, and the solid content obtained by removing residual moisture through vacuum drying may be used in the next step.

Alkylation Step

In addition, according to the present invention, it is possible to further include an alkylation reaction after the step (3), and as a result, X′ in the Formula 1 may be $C_{1-7}$ alkyl.

For example, the product after the step (4) may be reacted with methylboronic acid to obtain the compound of Formula 1a in which X′ is substituted with methyl.

Crystallization Step

The compound of Formula 1a may be produced in a crystalline form, an amorphous form, or a mixture thereof. However, the compound of Formula 1a in a crystalline form is preferred from the viewpoint of being excellent in stability and non-hygroscopicity and thus of having physicochemical properties which facilitate formulation.

Therefore, the method of the present invention may further comprise crystallizing the compound of Formula 1a after the step (3). The crystallization may be performed using various solvents, and thus various crystalline forms can be obtained.

As an example, the solvent used for the crystallization may be selected from toluene; ethyl acetate; dichloromethane; acetone; acetonitrile; a mixture of 2-propanol, tetrahydrofuran, and dichloromethane; and a mixture of tetrahydrofuran and n-hexane, and as a result, a crystalline form A can be produced.

As another example, the solvent used for the crystallization may be selected from a mixture of methanol and distilled water; a mixture of methanol and n-hexane; and a mixture of methanol, dichloromethane, and n-hexane, and as a result, a crystalline form B can be produced.

As still another example, the solvent used for the crystallization may be selected from a mixture of ethanol, distilled water, and n-hexane; and a mixture of tetrahydrofuran and toluene, and as a result, a crystalline form C can be produced.

As yet another example, the solvent used for the crystallization may be a mixture of ethanol and n-hexane, and as a result, a crystalline form D can be produced.

As a preferred example, the solvent used for the crystallization may be selected from the group consisting of toluene, ethyl acetate, dichloromethane, a mixture of tetrahydrofuran and dichloromethane, and a mixture of tetrahydrofuran and n-hexane.

Method for Producing Compound of Formula 1b (Formula 1 in which R=Alkylthio and A=Oxygen)

According to another aspect of the present invention, there is provided a method for producing the compound of Formula 1b (Formula 1 in which R=$C_{1-7}$ alkylthio and A=oxygen), the method comprising the following steps of:

(1) reacting a compound of the following Formula 2 with a compound of the following Formula 3 and subjecting the resultant to a cyclization reaction, to obtain a compound of the following Formula 4;

(2) subjecting the compound of Formula 4 to aldehydation or amidation, followed by reacting the resultant with the compound of Formula 5 and performing reduction, to obtain a compound of the following Formula 6;

(3) reacting the compound of Formula 6 with a compound of the following Formula 8 and then performing reduction, to obtain a compound of the following Formula 9;

(4) forming a furanose ring of the compound of Formula 9 into a pyranose ring under an acidic condition and then introducing a protecting group thereinto, to obtain a compound of the following Formula 10; and (5) treating the compound of Formula 10 with thiourea, reacting the resultant with $C_{1-7}$ alkyl halide, and then performing reduction.

[Formula 1b]

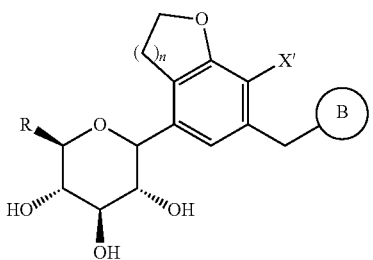

[Formula 2]

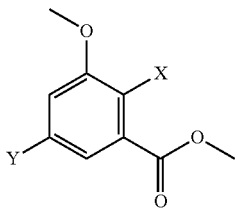

[Formula 3]

[Formula 4]

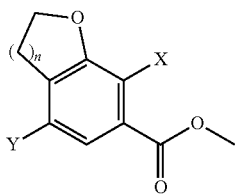

[Formula 5]

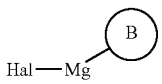

[Formula 6]

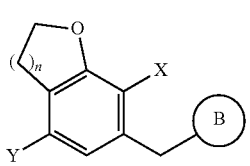

[Formula 8]

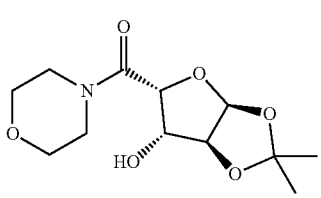

[Formula 9]

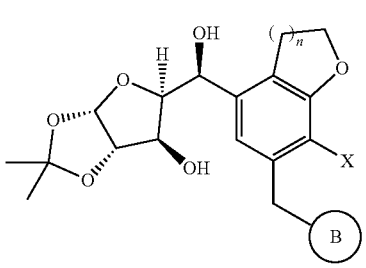

[Formula 10]

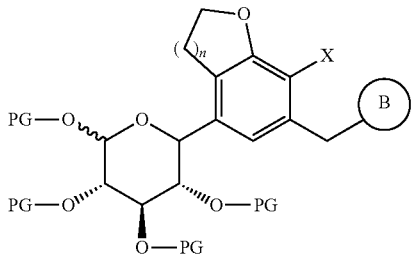

In the formulae,
R is $C_{1-7}$ alkylthio;
n is 1 or 2;
PG is a protecting group;
X' is halogen or $C_{1-7}$ alkyl;
X, Y, and Hal are each independently halogen; and
B is as defined above in Formula 1.

In the above steps, the steps (1) and (2) may be carried out in the same manner as in the steps (1) and (2) of the method for producing the compound of Formula 1a (Formula 1 in which R=hydroxymethyl).

The steps (3) to (5) will be described in detail below.

Step (3)

In the step (3), the compound of Formula 6 is reacted with the compound of Formula 8 to obtain the compound of Formula 9.

The compound of Formula 8 can be produced according to a known method, for example, the method disclosed in WO 2009/014970. Specifically, the compound of Formula 8 can be produced according to the method disclosed in WO 2009/014970 starting from L-xylose.

According to an example, the compound of Formula 6 can be reacted with the compound of Formula 8 to obtain a compound of the following Formula 9a.

[Formula 9a]

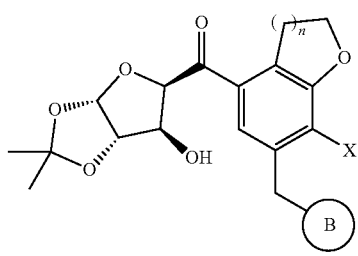

In the formula, B, n, and X are as defined above in Formula 1.

Then, the compound of Formula 9a can be reduced to obtain the compound of Formula 9.

Step (4)

In the step (4), a furanose ring of the compound of Formula 9 is formed into a pyranose ring under an acidic condition, and then a protecting group is introduced thereinto to obtain the compound of Formula 10. Through this step, the pyranose ring constituting the glucose group can be completed.

The protecting group may be, for example, an acetyl group.

Step (5)

In the step (5), the compound of Formula 10 is treated with thiourea, reacted with $C_{1-7}$ alkyl halide, and then reduced. Through this step, an alkylthio group can be introduced into the final compound (compound of Formula 1b).

The $C_{1-7}$ alkyl halide may be, for example, $C_{1-7}$ alkyl iodide.

In addition, after the step (5), an alkylation reaction may be further comprised, and as a result, the compound of Formula 1b in which X' is $C_{1-7}$ alkyl can be obtained.

Crystalline Form

According to still another aspect of the present invention, there is provided a crystalline form of the compound produced according to the above-described production method.

As an example, the present invention provides a crystalline form of the compound of Formula 1a.

As a specific example, the present invention provides a crystalline form of the compound of Formula 1a in which A is O, B is cyclopropylphenyl, n is 1, and X' is Cl, and which is in a β-form.

That is, the present invention provides a crystalline form of a compound of the following Formula c28.

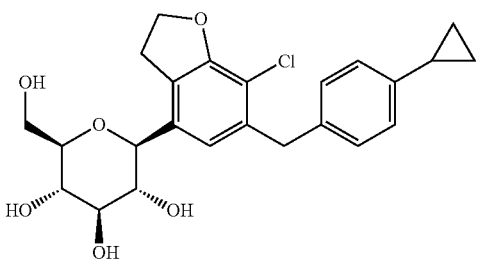

[Formula c28]

The compound of Formula c28 can be produced by the above-described production method of Formula 1a.

According to the present invention, it is possible that the compound of Formula c28 is in various crystalline forms, and the respective crystalline forms will be described in detail below.

In the following, the term "about" may mean to be within 5% and preferably within 2%, of a predetermined value or range. For example, "about 10%" may mean 9.5% to 10.5%, and preferably 9.8% to 10.2%. As another example, "about 100° C." may mean 95° C. to 105° C., and preferably 98° C. to 102° C.

First, the present invention provides a crystalline form A of the compound of Formula c28. The crystalline form A has an XRD spectrum which includes peaks at diffraction angles (2θ) of 6.2°±0.2°, 7.2°±0.2°, 8.8°±0.2°, 17.6°±0.2°, 19.0°±0.2°, 22.5°±0.2°, and 25.1°±0.2° in a case of being irradiated using a Cu—$K_\alpha$ light source. These peaks may be peaks with a relative intensity ($I/I_o$) being about 5% or higher and preferably about 10% or higher.

The XRD spectrum of the crystalline form A may further include peaks at diffraction angles (2θ) of 15.4°±0.2°, 18.6°±0.2°, 21.6°±0.2°, and 23.8°±0.2°.

In addition, the crystalline form may have an endothermic peak in which a starting point is about 157° C. and the lowest point is about 159° C., at DSC (10° C./minute).

In addition, the present invention provides a crystalline form B of the compound of Formula c28. The crystalline form B has an XRD spectrum which includes peaks at diffraction angles (2θ) of 7.0°±0.2°, 14.9°±0.2°, 17.7°±0.2°, 18.8°±0.2°, 20.6°±0.2°, 21.8°±0.2°, and 23.5°±0.2° in a case of being irradiated using a Cu—$K_\alpha$ light source. These peaks may be peaks with a relative intensity ($I/I_o$) being about 5% or higher and preferably about 10% or higher.

The XRD spectrum of the crystalline form B may further include peaks at diffraction angles (2θ) of 5.6°±0.2°, 9.4°±0.2°, and 11.0°±0.2°.

In addition, the crystalline form may have an endothermic peak in which a starting point is about 79° C. and the lowest point is about 88° C., and an endothermic peak in which a starting point is about 103° C. and the lowest point is about 111° C., at DSC (10° C./minute).

In addition, the present invention provides a crystalline form C of the compound of Formula c28. The crystalline form C has an XRD spectrum which includes peaks at diffraction angles (2θ) of 5.6°±0.2°, 7.3°±0.2°, 15.7°±0.2°, 17.2°±0.2°, 18.9°±0.2°, 21.2°±0.2°, and 21.9°±0.2° in a case of being irradiated using a Cu—$K_\alpha$ light source. These peaks may be peaks with a relative intensity ($I/I_o$) being about 5% or higher and preferably about 10% or higher.

The XRD spectrum of the crystalline form C may further include peaks at diffraction angles (2θ) of 19.9°±0.2° and 23.1°±0.2°.

In addition, the crystalline form may have an endothermic peak in which a starting point is about 157° C. and the lowest point is about 159° C., at DSC (10° C./minute).

In addition, the present invention provides a crystalline form D of the compound of Formula c28. The crystalline form D has an XRD spectrum which includes peaks at diffraction angles (2θ) of 5.5°±0.2°, 7.2°±0.2°, 15.3°±0.2°, 17.2°±0.2°, 17.6°±0.2°, 18.9°±0.2°, and 21.1°±0.2° in a case of being irradiated using a Cu—$K_\alpha$ light source. These peaks may be peaks with a relative intensity ($I/I_o$) being about 5% or higher.

The XRD spectrum of the crystalline form D may further include peaks at diffraction angles (2θ) of 20.0°±0.2°, 22.5°±0.2°, and 25.1°±0.2°.

In addition, the crystalline form may have an endothermic peak in which a starting point is about 157° C. and the lowest point is about 160° C., at DSC (10° C./minute).

Such crystalline forms of the compound of Formula c28 are excellent in physicochemical properties (for example, hygroscopicity and chemical stability), and thus can be easily handled in various fields (for example, production of pharmaceuticals).

MODE FOR CARRYING OUT INVENTION

Hereinafter, the present invention will be described in more detail with reference to examples. However, the following examples are intended to merely illustrate the present invention, and the scope of the present invention is not limited to these examples.

The meanings of abbreviations indicated in the following examples are as follows.

AcOH: Acetic acid
ACN: Acetonitrile
$Ac_2O$: Acetic anhydride
$BF_3.OEt_2$: Boron trifluoride etherate
DIPEA: N,N-Diisopropylethylamine
DCM: Dichloromethane
DMAP: 4-Dimethylaminopyridine
DMF: N,N-Dimethylformamide
EtOAc: Ethyl acetate
EtOH: ethanol
$Et_3SiH$: Triethylsilane
HBTU: 2-(1H-benzotriazol-1-yl)-1,1,3,3-tetramethyluronium hexafluorophosphate
Hex: Hexane i-PrOH: Isopropyl alcohol
MeI: Iodomethane
MeOH: Methanol
MsCl: Mesyl chloride
NaOMe: Sodium methoxide
NBS: N-Bromosuccinimide
PCC: Pyridinium chlorochromate
Pd(PPh$_3$)$_4$: Tetrakis(triphenylphosphine)palladium(0)
TEA: Triethylamine
TEMPO: (2,2,6,6-Tetramethylpiperidin-1-yl)oxadinyl
THF: Tetrahydrofuran
TMSOTf: Trimethylsilyl trifluoromethanesulfonate
RT or rt: Room temperature Comparative Example 1: Synthesis of (2S,3R,4R, 5S,6R)-2-(7-chloro-6-(4-cyclopropylbenzyl)-2,3-dihydrobenzofuran-4-yl)-6-(hydroxymethyl)tetrahydro-2H-pyran-3,4,5-triol The title compound was produced by the method disclosed in US Laid-open Patent Publication No. 2015/0152075. For specific synthesis steps of Comparative Example 1, reference is made to Scheme 1 as described above in the Background Art section.

Step 1: Methyl 3-methoxy-2-nitrobenzoate (Compound c2)

To a mixture of 3-methoxy-2-nitrobenzoic acid (25.0 g, 126 mmol) and K$_2$CO$_3$ (35.0 g, 253 mmol) in DMF (126 mL) was added MeI (15.8 mL, 253 mmol) at room temperature. The mixture was stirred at room temperature for 2 hours. To the mixture was poured the water (200 mL) and then stirred at 5° C. for 30 min. The precipitated solid was collected by filtration, washed with water and hexane. The solid was dried under reduced pressure to afford the title compound in a crude form (26.2 g, 98%) as a white solid.

$^1$H NMR (400 MHz, CDCl$_3$) δ 7.60 (dd, J=8.2, 1.2 Hz, 1H), 7.50 (t, J=8.2 Hz, 1H), 7.26 (dd, J=8.2, 1.2 Hz, 1H), 3.39 (s, 3H), 3.99 (s, 3H); [M+Na]$^+$ 235.

Step 2: Methyl 2-amino-3-methoxybenzoate (Compound c3)

A suspension of methyl 3-methoxy-2-nitrobenzoate (26.2 g, 124 mmol) and Pd/C (10 wt. %, 6.0 g) in THF (400 mL) and MeOH (200 mL) was stirred under an atmosphere of H$_2$ at room temperature for 18 hours. EtOAc (300 mL) was added to the mixture and filtered through a Celite pad. The filtrate was concentrated in vacuo to provide the title compound (22.4 g, 99%) as colorless oil.

$^1$H NMR (400 MHz, CDCl$_3$) δ 7.47 (dd, J=8.2, 1.2 Hz, 1H), 6.85 (dd, J=8.2, 1.2 Hz, 1H), 6.58 (t, J=8.2 Hz, 1H), 6.00 (brs, 2H), 3.87 (s, 3H); [M+H]$^+$ 182.

Step 3: Methyl 2-amino-5-bromo-3-methoxybenzoate (Compound c4)

To a solution of methyl 2-amino-3-methoxybenzoate (22.4 g 123 mmol) in DMF (250 mL) was added N-bromosuccinimide (21.9 g, 123 mmol) portionwise at 0° C. The mixture was stirred at 0° C. for 0.5 h. To the mixture was added water and extracted with EtOAc (500 mL×2). The combined organic layer was dried over MgSO$_4$, filtered, and concentrated in vacuo. The residue was purified by silica gel column chromatography to provide the title compound (27.5 g, 86%) as a white solid.

$^1$H NMR (400 MHz, CDCl$_3$) δ 7.60 (d, J=2.2 Hz, 1H), 6.90 (d, J=2.2 Hz, 1H), 6.03 (brs, 1H), 3.87 (s, 3H); [M+H]$^+$ 260.

Step 4: Methyl 5-bromo-2-chloro-3-methoxybenzoate (Compound c5)

To a solution of methyl 2-amino-5-bromo-3-methoxybenzoate (27.0 g, 103 mmol) in H$_2$O (70 mL) and conc. HCl (70 mL) was added dropwise a solution of NaNO$_2$ (21.5 g, 311 mmol) in H$_2$O (50 mL) at 0° C. After being stirred for 1 hour, a solution of Cu(I)Cl in conc. HCl (80 mL) was added to the reaction mixture dropwise at 0° C. The mixture was stirred at room temperature for 18 hours. To the mixture was added water (300 mL) and extracted with EtOAc (500 mL). The organic layer was dried over MgSO$_4$, filtered, and concentrated in vacuo. The crude title compound was dried under high vacuum and used for the next step without further purification (29.0 g, 100%) as a white solid.

$^1$H NMR (400 MHz, CDCl$_3$) δ 7.49 (d, J=2.4 Hz, 1H), 7.16 (d, J=2.4 Hz, 1H), 3.93 (s, 36H), 3.92 (s, 3H); [M+H]$^+$ 278

Step 5: 5-Bromo-2-chloro-3-methoxybenzoic acid (Compound c6)

To a solution of methyl 5-bromo-2-chloro-3-methoxybenzoate (25.0 g, 89.4 mmol) in THF (100 mL), H$_2$O (100 mL) and MeOH (100 mL) was added aq. 5 N NaOH solution dropwise at 0° C. The mixture was stirred at room temperature for 1 hour. conc. HCl was added to the mixture to acidify and the mixture was extracted with EtOAc (500 mL×2). The combined organic layers were dried over MgSO$_4$, filtered and concentrated in vacuo to afford the title compound (22.6 g, 96%) as an orange solid.

$^1$H NMR (400 MHz, CDCl$_3$) δ 7.55 (s, 1H), 7.13 (s, 1H), 3.89 (s, 3H); [M+H]$^+$ 265.

Step 6: 5-Bromo-2-chloro-3-methoxybenzoyl chloride (Compound c7)

To a suspension of 5-bromo-2-chloro-3-methoxybenzoic acid (6.0 g, 22.6 mmol) in CH$_2$Cl$_2$ (100 mL) were added oxalyl chloride (2.4 mL, 27.1 mmol) and catalytic amounts of DMF at room temperature. The mixture was stirred at room temperature for 2 hours. The mixture was evaporated in vacuo and dried under high vacuum to obtain the crude title compound.

$^1$H NMR (400 MHz, CDCl$_3$) δ 7.49 (d, J=2.4 Hz, 1H), 7.16 (d, J=2.4 Hz, 1H), 3.93 (s, 3H), 3.92 (s, 3H).

Step 7: (5-Bromo-2-chloro-3-hydroxyphenyl)(phenyl)methanone (Compound c8)

The crude 5-bromo-2-chloro-3-methoxybenzoyl chloride was dissolved with benzene (100 mL) and cooled to 0° C. To the reaction mixture was added AlCl$_3$ (6.9 g, 52.0 mmol) portionwise at 0° C. The mixture was stirred at 90° C. for 15 hours. The mixture was cooled to rt and evaporated in vacuo. The residue was cooled to 0° C. and aq. 1N HCl solution was added. The mixture was extracted with EtOAc (150 mL×1). The organic layer was dried over MgSO$_4$, filtered, and concentrated in vacuo. The residue was purified by silica gel column chromatography to provide the title compound (7.33 g, quantitative yield).

$^1$H NMR (400 MHz, CDCl$_3$) δ 7.85-7.82 (m, 2H), 7.70-7.64 (m, 1H), 7.55-7.49 (m, 2H), 7.37 (d, J=2.2 Hz, 1H), 7.13 (d, J=2.2 Hz, 1H), 5.94 (s, 1H).

Step 8: 3-Benzyl-5-bromo-2-chlorophenol (Compound c9)

To a mixture of (5-bromo-2-chloro-3-hydroxyphenyl)(phenyl)methanone (362 mg, 1.16 mmol) in trifluoroacetic acid (3 mL) was added added triethylsilane (0.37 mL, 2.32 mmol) and catalytic triflic acid at 0° C. The mixture was stirred at room temperature for 12 hours. The resulting mixture was quenched with saturated NaHCO$_3$ solution at 0° C. and extracted with EtOAc. The organic layer was dried over MgSO$_4$, filtered, and concentrated in vacuo. The crude product was purified by silica gel column chromatography (Biotage Isolera™ FLASH Purification System, EtOAc/Hex) to provide the title compound (267 mg, 77%).

$^1$H NMR (400 MHz, CDCl$_3$) δ 7.37-7.32 (m, 2H), 7.30-7.27 (m, 1H), 7.22-7.19 (m, 2H), 7.13 (d, J=2.4 Hz, 1H), 6.92 (d, J=2.0 Hz, 1H), 4.07 (s, 2H). [M+H]$^+$ 297.

Step 9: 1-(Allyloxy)-3-benzyl-5-bromo-2-chlorobenzene (Compound c10)

To a mixture of 3-benzyl-5-bromo-2-chlorophenol (1.72 g, 5.78 mmol) and K$_2$CO$_3$ (1.6 g, 11.56 mmol) in acetone (35 mL) was added allyl bromide (0.73 mL, 8.67 mmol) at room temperature. The reaction mixture was stirred for 12 hours at 65° C. The resulting mixture was filtered to remove inorganic materials. The filtrate was concentrated in vacuo. The crude product was purified by silica gel column chromatography (Biotage Isolera™ FLASH Purification System, EtOAc/Hex) to provide the title compound (1.96 g, 100%).

$^1$H NMR (400 MHz, CDCl$_3$) δ 7.32-7.27 (m, 2H), 7.25-7.22 (m, 1H), 7.21-7.17 (m, 2H), 6.92 (d, J=2.4 Hz, 1H), 6.92 (d, J=2.0 Hz, 1H), 6.10-6.00 (m, 1H), 5.48 (dq, J=17.2 Hz, 1.6 Hz, 1H), 5.33 (dq, J=12.4, 1.6 Hz, 1H), 4.59 (dt, J=4.4 Hz, 1.6 Hz, 2H), 4.08 (s, 2H). [M+H]$^+$ 337.

Step 10: (3R,4S,5S,6R)-2-(3-(Allyloxy)-5-benzyl-4-chlorophenyl)-6-(hydroxymethyl)-2-methoxytetrahydro-2H-pyran-3,4,5-triol (Compound c12)

To a solution of 1-(allyloxy)-3-benzyl-5-bromo-2-chlorobenzene (1.96 g, 5.82 mmol) in tetrahydrofuran (5.5 mL)/toluene (11 mL) was added dropwise n-butyllithium (2.5 M in hexanes, 2.6 mL, 6.41 mmol) at −78° C. under nitrogen atmosphere. After stirring for 1 hour, a solution of (3R,4S,5R,6R)-3,4,5-tris((trimethylsilyl)oxy)-6-(((trimethylsilyl)oxy)methyl)tetrahydro-2H-pyran-2-one (a; 3.54 g, 7.58 mmol) in tetrahydrofuran (6.6 mL) was added dropwise to the mixture by cannular for 20 min at −78° C. The reaction mixture was stirred for 3 hours at −78° C. CH$_3$SO$_3$H (0.6 mL, 9.25 mmol) in MeOH (15 mL) was added dropwise to the mixture at 0° C. The mixture was warmed up to room temperature over 18 hours, and then quenched with saturated NaHCO$_3$ at 0° C. The mixture was evaporated under reduced pressure to remove volatiles. The aqueous residue was extracted with EtOAc (100 mL×2). The combined organic layers were dried over MgSO$_4$, filtered and concentrated in vacuo to provide the crude title product as a yellow solid. [M+Na]$^+$ 473.

Step 11: (3R,4R,5S,6R)-2-(3-(Allyloxy)-5-benzyl-4-chlorophenyl)-6-(hydroxymethyl)tetrahydro-2H-pyran-3,4,5-triol (Compound c13)

To a mixture of (3R,4S,5S,6R)-2-(3-(allyloxy)-5-benzyl-4-chlorophenyl)-6-(hydroxymethyl)-2-methoxytetrahydro-2H-pyran-3,4,5-triol (2.55 g, 5.65 mmol) in CH$_2$Cl$_2$ (30 mL) and CH$_3$CN (30 mL) was added dropwise Et$_3$SiH (1.82 mL, 11.3 mmol) and BF$_3$.Et$_2$O (1.07 mL, 8.48 mmol) at 0° C. The reaction mixture was stirred for 5 hours at room temperature. The resulting mixture was quenched with saturated NaHCO$_3$ solution and extracted with EtOAc The organic layer was dried over MgSO$_4$, filtered, and concentrated in vacuo. The crude product was used for the next step without further purification.

Step 12: (2R,3R,4R,5S,6S)-2-(Acetoxymethyl)-6-(3-(allyloxy)-5-benzyl-4-chlorophenyl)tetrahydro-2H-pyran-3,4,5-triyl triacetate (Compound c14)

To a mixture of (3R,4R,5S,6R)-2-(3-(allyloxy)-5-benzyl-4-chlorophenyl)-6-(hydroxymethyl)tetrahydro-2H-pyran-3,4,5-triol (c13) in CH$_2$Cl$_2$ (12 mL) was added Ac$_2$O (4.7 mL, 49.72 mmol), pyridine (4.0 mL, 49.45 mmol), and DMAP (35 mg, 0.28 mmol) at room temperature. The reaction mixture was stirred for 12 hours at room temperature. The resulting mixture was diluted with EtOAc and washed with 1 N HCl solution. The organic layer was dried over MgSO$_4$, filtered, and concentrated in vacuo. The crude product was purified by silica gel column chromatography (Biotage Isolera™ FLASH Purification System, EtOAc/Hex) to provide the title compound (1.55 g, 47%).

$^1$H NMR (400 MHz, DMSO-d$_6$) δ 7.31-7.27 (m, 2H), 7.22-7.21 (m, 1H), 7.19-7.16 (m, 2H), 7.09 (d, J=1.6 Hz, 1H), 6.88 (d, J=1.6 Hz, 1H), 6.12-6.03 (m, 1H), 5.47 (dq, J=17.6, 2.0 Hz, 1H), 5.35 (t, J=9.6 Hz, 1H), 5.30 (dq, J=10.4, 1.6 Hz, 1H), 5.12 (t, J=9.6 Hz, 1H), 5.06 (t, J=9.6 Hz, 1H), 4.66-4.62 (m, 3H), 4.13-4.03 (m, 5H), 2.04 (s, 3H), 2.03 (s, 3H), 1.95 (s, 3H), 1.70 (s, 3H); [M+Na]$^+$ 611.

Step 13: (2S,3R,4R,5S,6R)-2-(3-(Allyloxy)-5-benzyl-4-chlorophenyl)-6-(hydroxymethyl)tetrahydro-2H-pyran-3,4,5-triol (Compound c15)

To a mixture of (2R,3R,4R,5S,6S)-2-(Acetoxymethyl)-6-(3-(allyloxy)-5-benzyl-4-chlorophenyl)tetrahydro-2H-pyran-3,4,5-triyl triacetate (1.55 g, 2.63 mmol) in MeOH (50 mL) was added NaOMe (25 wt % in MeOH, 2.34 mL) at room temperature. The mixture was stirred at room temperature for 12 hours. The resulting mixture was neutralized with glacial AcOH. The mixture was diluted with EtOAc and washed with saturated NaHCO$_3$ solution. The organic layer was dried over MgSO$_4$, filtered, and concentrated in vacuo. The crude product was used for the next step without further purification. [M+Na]$^+$ 443.

Step 14: (2S,3S,4R,5R,6R)-2-(3-(Allyloxy)-5-benzyl-4-chlorophenyl)-3,4,5-tris(benzyloxy)-6-((benzyloxy)methyl)tetrahydro-2H-pyran (Compound c16)

To a mixture of (2S,3R,4R,5S,6R)-2-(3-(allyloxy)-5-benzyl-4-chlorophenyl)-6-(hydroxymethyl)tetrahydro-2H-pyran-3,4,5-triol in DMF (26 mL) was added NaH (60% dispersion in mineral oil, 842 mg, 21.0 mmol) at 0° C. and stirred for 1 hour at room temperature. Benzyl bromide (2.5 mL, 21.0 mmol) was added dropwise to the reaction mixture at 0° C. The mixture was stirred for 12 hours at room temperature. The resulting mixture was quenched with water and extracted with EtOAc. The organic layer was dried over MgSO$_4$, filtered, and concentrated in vacuo. The crude product was purified by silica gel column chromatography (Biotage Isolera™ FLASH Purification System, EtOAc/Hex) to provide the title compound (1.80 g, 88%).

$^1$H NMR (400 MHz, CDCl$_3$) δ 7.36-7.31 (m, 13H), 7.26-7.19 (m, 10H), 6.94 (d, J=1.6 Hz, 2H), 6.91 (dd, J=14.8, 2.0 Hz, 2H), 6.10-6.00 (m, 1H), 5.46 (dq, J=17.2, 1.6 Hz, 1H), 5.31 (dq, J=10.8, 1.6 Hz, 1H), 4.94 (ABq, J$_{AB}$=15.2 Hz, 2H), 4.90 (d, J=10.8 Hz, 1H), 4.70-4.64 (m, 2H), 4.57 (d, J=12.4 Hz, 1H), 4.52-4.49 (m, 2H), 4.46 (d, J=10.8 Hz, 1H), 4.23-4.16 (m, 2H), 4.08 (d, J=15.2 Hz, 1H), 3.89 (d, J=10.8 Hz, 1H), 3.84-3.75 (m, 4H), 3.61-3.57 (m, 1H), 3.48-3.44 (m, 1H); [M+Na]$^+$ 803.

Step 15: 3-Benzyl-2-chloro-5-((2S,3S,4R,5R,6R)-3,4,5-tris(benzyloxy)-6-((benzyloxy)methyl)tetrahydro-2H-pyran-2-yl)phenol (Compound c17)

To a mixture of ((2S,3S,4R,5R,6R)-2-(3-(Allyloxy)-5-benzyl-4-chlorophenyl)-3,4,5-tris(benzyloxy)-6-((benzyloxy)methyl)tetrahydro-2H-pyran (1.80 g, 2.30 mmol) in THF (25 mL) was added NaBH$_4$ (700 mg, 18.4 mmol) and Pd(PPh$_3$)$_4$ (266 mg, 0.23 mmol) at room temperature. The reaction mixture was stirred for 12 hours at room temperature. The resulting mixture was quenched with saturated NaHCO$_3$ solution and extracted with EtOAc. The organic layer was dried over MgSO$_4$, filtered, and concentrated in vacuo. The crude product was purified by silica gel column chromatography (Biotage Isolera™ FLASH Purification System, EtOAc/Hex) to provide the title compound (1.62 g, 95%).

$^1$H NMR (400 MHz, CDCl$_3$) δ 7.37-7.31 (m, 13H), 7.27-7.21 (m, 8H), 7.18-7.16 (m, 2H), 7.08 (d, J=2.0 Hz, 1H), 6.98 (dd, J=7.6, 2.0 Hz, 2H), 6.89 (d, J=2.0 Hz, 1H), 4.93 (ABq, J$_{AB}$=16.0 Hz, 2H), 4.89 (d, J=10.8 Hz, 1H), 4.67 (d, J=4.8 Hz, 1H), 4.64 (d, J=6.0 Hz, 1H), 4.57 (d, J=12.4 Hz, 1H), 4.46 (d, J=10.4 Hz, 1H), 4.19-4.12 (m, 2H), 4.03 (d, J=15.2 Hz, 1H), 3.95 (d, J=10.4 Hz, 1H), 3.82-3.75 (m, 4H), 3.61-3.57 (m, 1H), 3.49-3.45 (m, 1H); [M+Na]$^+$ 763.

Step 16: 3-Benzyl-6-bromo-2-chloro-5-((2S,3S,4R,5R,6R)-3,4,5-tris(benzyloxy)-6-((benzyloxy)methyl)tetrahydro-2H-pyran-2-yl)phenol (Compound c18)

To a mixture of 3-benzyl-2-chloro-5-((2S,3S,4R,5R,6R)-3,4,5-tris(benzyloxy)-6-((benzyloxy)methyl)tetrahydro-2H-pyran-2-yl)phenol (1.62 g, 2.18 mmol) in AcOH (11 mL) was added triethylamine (0.46 mL, 3.27 mmol) and bromine (0.11 mL, 2.18 mmol) at 0° C. The reaction mixture was stirred for 12 hours at room temperature. The resulting mixture was quenched with saturated NaHCO$_3$ solution and extracted with EtOAc. The organic layer was dried over MgSO$_4$, filtered, and concentrated in vacuo. The crude product was purified by silica gel column chromatography (Biotage Isolera™ FLASH Purification System, EtOAc/Hex) to provide the title compound (1.04 g, 58%). [M+Na]$^+$ 841.

Step 17: 3-(3-Benzyl-6-bromo-2-chloro-5-((2S,3S,4R,5R,6R)-3,4,5-tris(benzyloxy)-6-((benzyloxy)methyl)tetrahydro-2H-pyran-2-yl)phenoxy)propan-1-ol (Compound c19)

To a mixture of 3-benzyl-6-bromo-2-chloro-5-((2S,3S,4R,5R,6R)-3,4,5-tris(benzyloxy)-6-((benzyloxy)methyl)tetrahydro-2H-pyran-2-yl)phenol (1.04 g, 1.27 mmol) and K$_2$CO$_3$ (0.35 g, 2.54 mmol) in acetone (13 mL) was added 2-bromoethanol (0.14 mL, 1.90 mmol) at room temperature. The reaction mixture was stirred for 12 hours at 50° C. The resulting mixture was filtered to remove inorganic materials. The filtrate was concentrated in vacuo. The crude product was purified by silica gel column chromatography (Biotage Isolera™ FLASH Purification System, EtOAc/Hex) to provide the compound c19 (1.10 g, 100%). [M+Na]$^+$ 899.

Step 18: (2S,3S,4R,5R,6R)-2-(5-Benzyl-2-bromo-4-chloro-3-(2-chloroethoxy)phenyl)-3,4,5-tris(benzyloxy)-6-((benzyloxy)methyl)tetrahydro-2H-pyran (Compound c20)

To a mixture of 3-(3-benzyl-6-bromo-2-chloro-5-((2S,3S,4R,5R,6R)-3,4,5-tris(benzyloxy)-6-((benzyloxy)methyl)tetrahydro-2H-pyran-2-yl)phenoxy)propan-1-ol (1.09 g, 1.25 mmol) and triphenylphosphine (1.64 g, 6.28 mmol) in CH$_3$CN (12 mL) was added carbon tetrachloride (12 mL, 134 mmol) at room temperature. The reaction mixture was stirred for 12 hours at 55° C. The resulting mixture was evaporated to remove the solvents. The crude product was purified by silica gel column chromatography (Biotage Isolera™ FLASH Purification System, EtOAc/Hex) to provide the title compound (0.61 g, 55%). [M+Na]$^+$ 903.

Step 19: 6-Benzyl-7-chloro-4-((2S,3S,4R,5R,6R)-3,4,5-tris(benzyloxy)-6-((benzyloxy)methyl)tetrahydro-2H-pyran-2-yl)-2,3-dihydrobenzofuran (Compound c21)

To a mixture of (2S,3S,4R,5R,6R)-2-(5-benzyl-2-bromo-4-chloro-3-(2-chloroethoxy)phenyl)-3,4,5-tris(benzyloxy)-6-((benzyloxy)methyl)tetrahydro-2H-pyran (10.02 g, 11.4 mmol) in THF (114 mL) was added dropwise n-butyllithium (2.5 M in hexanes, 6.8 mL, 17.0 mmol) at −78° C. The reaction mixture was stirred for 3 hours at −78° C. The resulting mixture was quenched with 1 N HCl solution (100 mL) and extracted with EtOAc. The organic layer was dried over MgSO$_4$, filtered, and concentrated in vacuo. The crude product was purified by silica gel column chromatography (Biotage Isolera™ FLASH Purification System, EtOAc/Hex) to provide the title compound (6.0 g, 69%). [M+Na]$^+$ 789.

Step 20: (2S,3R,4R,5S,6R)-2-(6-Benzyl-7-chloro-2,3-dihydrobenzofuran-4-yl)-6-(hydroxymethyl)tetrahydro-2H-pyran-3,4,5-triol (Compound c22)

A mixture of 6-benzyl-7-chloro-4-((2S,3S,4R,5R,6R)-3,4,5-tris(benzyloxy)-6-((benzyloxy)methyl)tetrahydro-2H-pyran-2-yl)-2,3-dihydrobenzofuran (6.0 g, 7.82 mmol) and Pd/C (0.35 g, 2.54 mmol) in MeOH (220 mL)/THF (220 mL) was stirred for 5 hours at room temperature under H$_2$. The resulting mixture was filtered to remove inorganic materials through Celite. The filtrate was concentrated in vacuo to provide the title compound (quantitative amount). The crude product was used for the next step without further purification.

$^1$H NMR (400 MHz, CD$_3$OD) δ 7.28-7.14 (m, 5H), 6.89 (s, 1H), 4.65 (t, J=8.6 Hz, 2H), 4.17 (d, J=8.8 Hz, 1H), 4.07 (ABq, Δν$_{AB}$=18.0 Hz, J$_{AB}$=15.0 Hz, 2H), 3.90 (dd, J=11.8, 1.4 Hz, 1H), 3.72-3.67 (m, 1H), 3.53-3.42 (m, 3H), 3.40-3.37 (m, 2H); [M+Na]$^+$ 507.

Step 21: (2R,3R,4R,5S,6S)-2-(Acetoxymethyl)-6-(6-benzyl-7-chloro-2,3-dihydrobenzofuran-4-yl)tetrahydro-2H-pyran-3,4,5-triyl triacetate (Compound c23)

To a mixture of (2S,3R,4R,5S,6R)-2-(6-benzyl-7-chloro-2,3-dihydrobenzofuran-4-yl)-6-(hydroxymethyl)tetrahydro-2H-pyran-3,4,5-triol in CH$_2$Cl$_2$ (78 mL) was added Ac$_2$O (5.9 mL, 62.6 mmol), pyridine (5.0 mL, 62.6 mmol), and DMAP (48 mg, 0.39 mmol) at room temperature. The reaction mixture was stirred for 12 hours at room temperature. The resulting mixture was diluted with EtOAc and washed with 1 N HCl solution. The organic layer was dried over MgSO$_4$, filtered, and concentrated in vacuo. The crude product was purified by silica gel column chromatography (Biotage Isolera™ FLASH Purification System, EtOAc/Hex) to provide the title compound (4.54 g, 100%).

$^1$H NMR (400 MHz, CDCl$_3$) δ 7.32-7.28 (m, 2H), 7.25-7.18 (m, 3H), 6.59 (s, 1H), 5.30 (t, J=9.2 Hz, 2H), 5.19 (t, J=9.6 Hz, 1H), 4.77-4.68 (m, 2H), 4.35-4.32 (m, 1H), 4.31-4.26 (m, 1H), 4.21-4.14 (m, 1H), 4.11 (m, 1H), 4.02 (d, J=15.6 Hz, 1H), 3.83-3.79 (m, 1H), 3.42 (td, J=8.8, 1.6 Hz, 2H), 2.10 (s, 3H), 2.09 (s, 3H), 2.03 (s, 3H), 1.70 (s, 3H); [M+Na]$^+$ 597.

Step 22: (2R,3R,4R,5S,6S)-2-(Acetoxymethyl)-6-(6-(4-acetylbenzyl)-7-chloro-2,3-dihydrobenzofuran-4-yl)tetrahydro-2H-pyran-3,4,5-triyl triacetate (Compound c24)

To a mixture of (2R,3R,4R,5S,6S)-2-(acetoxymethyl)-6-(6-benzyl-7-chloro-2,3-dihydrobenzofuran-4-yl)tetrahydro-2H-pyran-3,4,5-triyl triacetate (3.75 g, 6.52 mmol) in CH$_2$Cl$_2$ (78 mL) was added dropwise acetyl chloride (3.71 mL, 52.16 mmol) and aluminum chloride (6.95 mg, 52.16 mmol) at 0° C. The reaction mixture was stirred for 12 hours at room temperature. The resulting mixture was quenched with ice-water and extracted with CH$_2$Cl$_2$. The organic layer was dried over MgSO$_4$, filtered, and concentrated in vacuo. The crude product was purified by silica gel column chromatography (Biotage Isolera™ FLASH Purification System, EtOAc/Hex) to provide the title compound (3.73 g, 93%).

$^1$H NMR (400 MHz, CDCl$_3$) δ 7.92-7.89 (m, 2H), 7.29-7.28 (m, 2H), 6.63 (s, 1H), 5.34-5.31 (m, 1H), 5.24-5.18 (m, 2H), 4.78-4.68 (m, 2H), 4.37-4.27 (m, 2H), 4.19-4.16 (m, 1H), 4.16-4.08 (m, 3H), 3.84-3.77 (m, 1H), 3.45-3.40 (m, 2H), 2.61 (s, 3H), 2.10 (s, 3H), 2.09 (s, 3H), 2.03 (s, 3H), 1.70 (s, 3H); [M+Na]$^+$ 639.

Step 23: (2R,3R,4R,5S,6S)-2-(Acetoxymethyl)-6-(7-chloro-6-(4-(1-hydroxyethyl)benzyl)-2,3-dihydrobenzofuran-4-yl)tetrahydro-2H-pyran-3,4,5-triyl triacetate (Compound c25)

To a mixture of (2R,3R,4R,5S,6S)-2-(acetoxymethyl)-6-(6-(4-acetylbenzyl)-7-chloro-2,3-dihydrobenzofuran-4-yl)tetrahydro-2H-pyran-3,4,5-triyl triacetate (1.0 g, 1.62 mmol) in THF (7 mL) was slowly added sodium borohydride (0.12 g, 3.24 mmol) at −20° C., and then MeOH (0.24 mL) was added dropwise to the mixture. The mixture was stirred for 3 hours at room temperature. The resulting mixture was quenched with saturated NaHCO$_3$ and extracted with EtOAc. The organic layer was dried over MgSO$_4$, filtered, and concentrated in vacuo. The crude product was purified by silica gel column chromatography (Biotage Isolera™ FLASH Purification System, EtOAc/Hex) to provide the title compound (0.52 g, 52%).

$^1$H NMR (400 MHz, CDCl$_3$) δ 7.29-7.27 (m, 2H), 7.15-7.12 (m, 2H), 6.54 (d, J=5.2 Hz, 1H), 5.29-5.26 (m, 1H), 5.18-5.13 (m, 2H), 4.89-4.84 (m, 2H), 4.71-4.66 (m, 2H), 4.32-4.29 (m, 1H), 4.27-4.22 (m, 1H), 4.15-4.11 (m, 1H), 4.04-3.96 (m, 2H), 3.80-3.75 (m, 1H), 3.40-3.35 (m, 2H), 2.06 (s, 3H), 2.05 (s, 3H), 1.99 (s, 3H), 1.68 (s, 3H), 1.47 (d, J=6.4 Hz, 3H); [M+Na]$^+$ 641.

Step 24: (2R,3R,4R,5S,6S)-2-(Acetoxymethyl)-6-(7-chloro-6-(4-vinylbenzyl)-2,3-dihydrobenzofuran-4-yl)tetrahydro-2H-pyran-3,4,5-triyl triacetate (Compound c26)

A mixture of (2R,3R,4R,5S,6S)-2-(acetoxymethyl)-6-(7-chloro-6-(4-(1-hydroxyethyl)benzyl)-2,3-dihydrobenzofuran-4-yl)tetrahydro-2H-pyran-3,4,5-triyl triacetate (520 mg, 0.84 mmol) and p-Toluenesulfonic acid monohydrate (16 mg, 0.084 mmol) in toluene (10 mL) was stirred for 2 hours at 120° C. The resulting mixture was diluted with EtOAc and washed with water. The organic layer was dried over MgSO$_4$, filtered, and concentrated in vacuo. The crude product was purified by silica gel column chromatography (Biotage Isolera™ FLASH Purification System, EtOAc/Hex) to provide the title compound (407 mg, 81%).

$^1$H NMR (400 MHz, CDCl$_3$) δ 7.32-7.30 (m, 2H), 7.12-7.10 (m, 2H), 6.71-6.63 (m, 1H), 6.55 (s, 1H), 5.71-5.66 (m, 1H), 5.29-5.25 (m, 1H), 5.25-5.13 (m, 3H), 4.71-4.66 (m, 2H), 4.33-4.29 (m, 1H), 4.28-4.22 (m, 1H), 4.15-4.11 (m, 1H), 4.08-3.96 (m, 2H), 3.79-3.75 (m, 1H), 3.41-3.35 (m, 2H), 2.06 (s, 3H), 2.05 (s, 3H), 1.99 (s, 3H), 1.68 (s, 3H); [M+Na]$^+$ 623.

Step 25: (2R,3R,4R,5S,6S)-2-(Acetoxymethyl)-6-(7-chloro-6-(4-cyclopropylbenzyl)-2,3-dihydrobenzofuran-4-yl)tetrahydro-2H-pyran-3,4,5-triyl triacetate (Compound c27)

To a solution of diethyl zinc (1.1 M in toluene, 1.74 mL, 1.91 mmol) in CH$_2$Cl$_2$ (3 mL) was added dropwise trifluoroacetic acid (0.15 mL, 1.91 mmol) in CH$_2$Cl$_2$ (1.5 mL) at 0° C. After 1 hour, diiodomethane (0.16 mL, 1.91 mmol) in CH$_2$Cl$_2$ (1.5 mL) was added dropwise to the mixture at 0° C. After 1 hour, (2R,3R,4R,5S,6S)-2-(acetoxymethyl)-6-(7-chloro-6-(4-vinylbenzyl)-2,3-dihydrobenzofuran-4-yl)tetrahydro-2H-pyran-3,4,5-triyl triacetate (460 mg, 0.77 mmol) in CH$_2$Cl$_2$ (3 mL) was slowly added to the mixture at 0° C. The reaction mixture was stirred for 12 hours at room temperature. The resulting mixture was quenched with saturated with NH$_4$Cl solution and extracted with EtOAc. The organic layer was dried over MgSO$_4$, filtered, and concentrated in vacuo. The crude product was purified by silica gel column chromatography (Biotage Isolera™ FLASH Purification System, EtOAc/Hex) to provide the title compound (285 mg, 60%).

$^1$H NMR (400 MHz, CDCl$_3$) δ 7.04-7.02 (m, 2H), 6.98-6.95 (m, 2H), 6.53 (s, 1H), 5.29-5.24 (m, 1H), 5.18-5.12 (m, 2H), 4.71-4.65 (m, 2H), 4.31-4.26 (m, 1H), 4.25-4.22 (m, 1H), 4.15-4.11 (m, 1H), 4.05-3.91 (m, 2H), 3.79-3.74 (m, 1H), 3.40-3.35 (m, 2H), 2.06 (s, 3H), 2.05 (s, 3H), 1.99 (s, 3H), 1.88-1.81 (m, 1H), 1.66 (s, 3H), 0.94-0.89 (m, 2H), 0.66-0.61 (m, 2H); [M+Na]$^+$ 637.

Step 26: (2S,3R,4R,5S,6R)-2-(7-Chloro-6-(4-cyclopropylbenzyl)-2,3-dihydrobenzofuran-4-yl)-6-(hydroxymethyl)tetrahydro-2H-pyran-3,4,5-triol (Compound c28)

A mixture of (2R,3R,4R,5S,6S)-2-(Acetoxymethyl)-6-(7-chloro-6-(4-cyclopropylbenzyl)-2,3-dihydrobenzofuran-4- yl)tetrahydro-2H-pyran-3,4,5-triyl triacetate (298 mg, 0.48 mmol) and K₂CO₃ (536 mg, 3.88 mmol) in MeOH (20 mL) was stirred for 12 hours at 12 hours. The resulting mixture was filtered to remove inorganic materials. The filtrate was concentrated in vacuo. The crude product was purified by prep HPLC (Gilson system, CH₃CN/H₂O) to provide the title compound (101 mg, 47%).

A total yield of the final compound of Comparative Example 1 according to the synthetic pathway of the above steps 1 to 26 was calculated as 1% or less.

¹H NMR (400 MHz, CD₃OD) δ 7.02 (d, J=8.0 Hz, 2H), 6.92 (d, J=8.0 Hz, 2H), 6.81 (s, 1H), 4.59 (t, J=8.8 Hz, 2H), 4.11 (d, J=9.2 Hz, 1H), 3.96 (ABq, $\Delta v_{AB}$=19.0 Hz, $J_{AB}$=15.2 Hz, 2H), 3.87-3.84 (m, 1H), 3.67-3.63 (m, 1H), 3.47-3.37 (m, 3H), 3.35-3.33 (m, 3H), 1.85-1.79 (m, 1H), 0.91-0.86 (m, 2H), 0.61-0.57 (m, 2H); [M+Na]⁺ 469.

Example 1: Synthesis of (2S,3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol

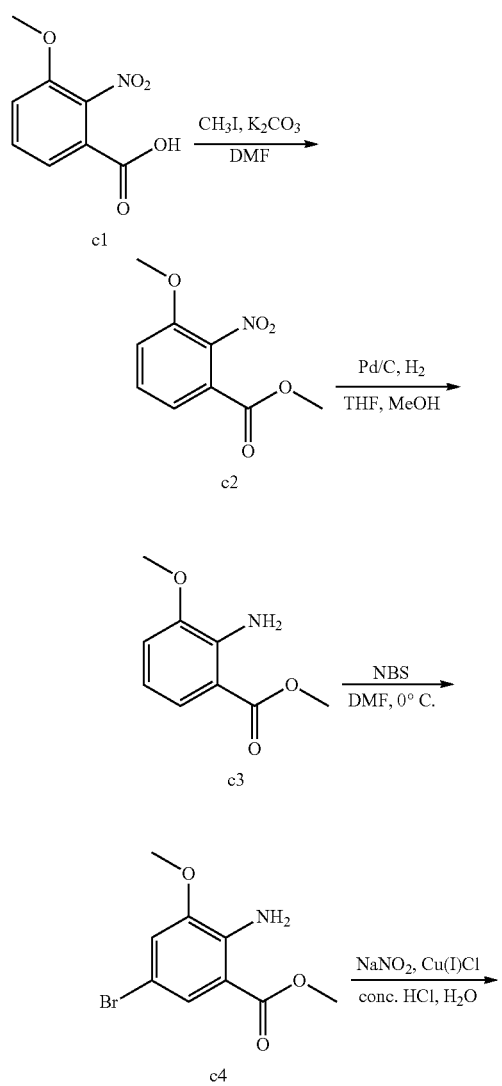

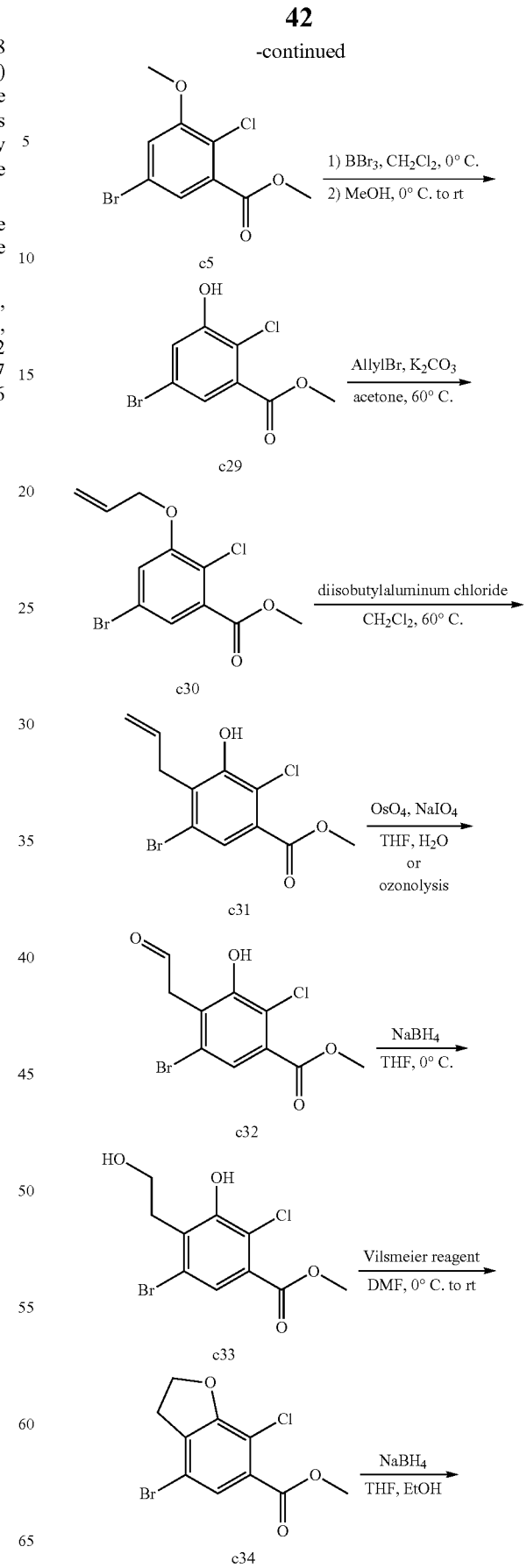

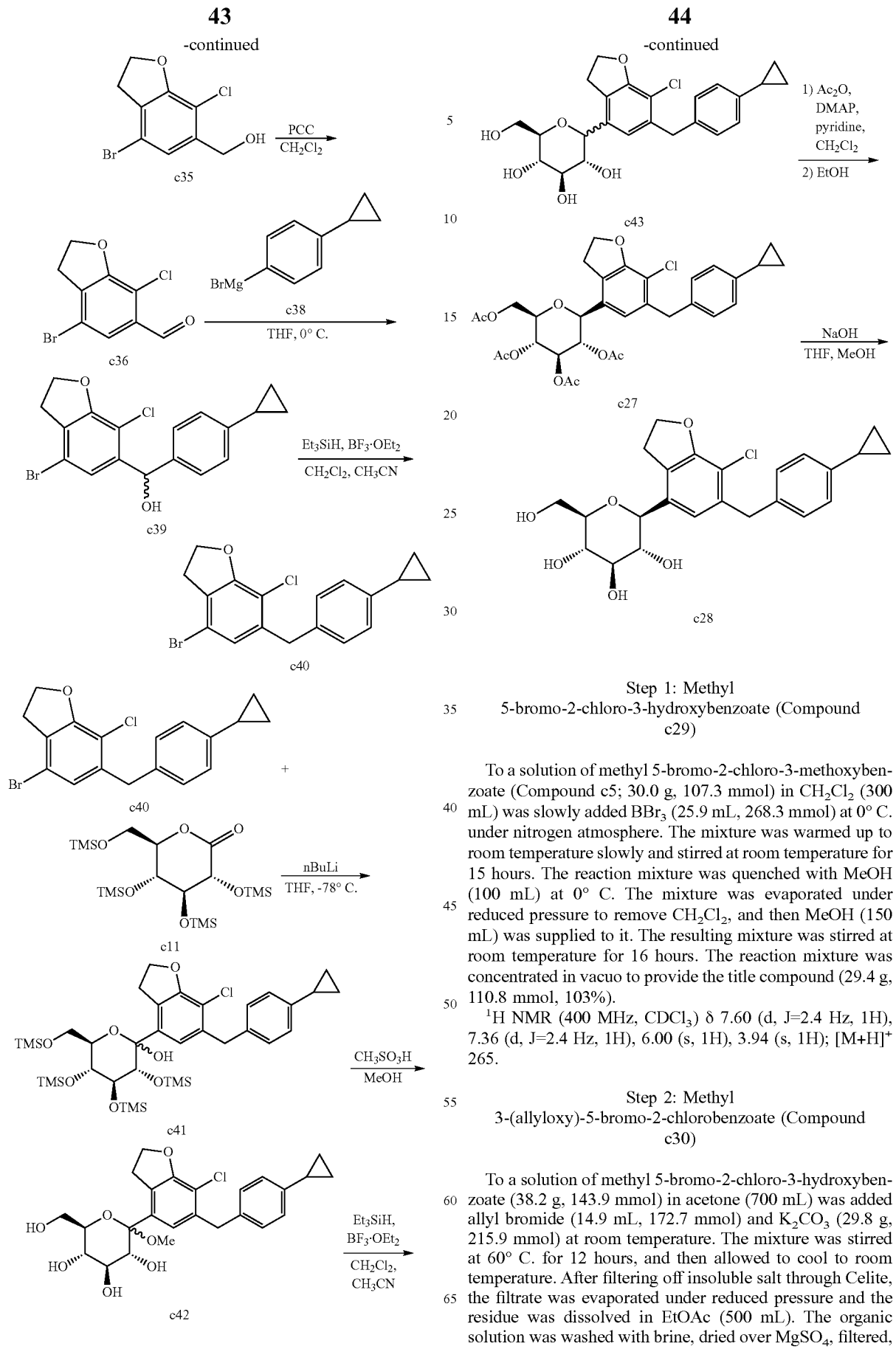

Step 1: Methyl 5-bromo-2-chloro-3-hydroxybenzoate (Compound c29)

To a solution of methyl 5-bromo-2-chloro-3-methoxybenzoate (Compound c5; 30.0 g, 107.3 mmol) in $CH_2Cl_2$ (300 mL) was slowly added $BBr_3$ (25.9 mL, 268.3 mmol) at 0° C. under nitrogen atmosphere. The mixture was warmed up to room temperature slowly and stirred at room temperature for 15 hours. The reaction mixture was quenched with MeOH (100 mL) at 0° C. The mixture was evaporated under reduced pressure to remove $CH_2Cl_2$, and then MeOH (150 mL) was supplied to it. The resulting mixture was stirred at room temperature for 16 hours. The reaction mixture was concentrated in vacuo to provide the title compound (29.4 g, 110.8 mmol, 103%).

$^1$H NMR (400 MHz, $CDCl_3$) δ 7.60 (d, J=2.4 Hz, 1H), 7.36 (d, J=2.4 Hz, 1H), 6.00 (s, 1H), 3.94 (s, 1H); $[M+H]^+$ 265.

Step 2: Methyl 3-(allyloxy)-5-bromo-2-chlorobenzoate (Compound c30)

To a solution of methyl 5-bromo-2-chloro-3-hydroxybenzoate (38.2 g, 143.9 mmol) in acetone (700 mL) was added allyl bromide (14.9 mL, 172.7 mmol) and $K_2CO_3$ (29.8 g, 215.9 mmol) at room temperature. The mixture was stirred at 60° C. for 12 hours, and then allowed to cool to room temperature. After filtering off insoluble salt through Celite, the filtrate was evaporated under reduced pressure and the residue was dissolved in EtOAc (500 mL). The organic solution was washed with brine, dried over $MgSO_4$, filtered, and concentrated in vacuo (44.1 g, 144.3 mmol, 100%). The crude residue was carried on to the next step without further purification.

$^1$H NMR (400 MHz, CDCl$_3$) δ 7.49 (d, J=2.4 Hz, 1H), 7.16 (d, J=2.4 Hz, 1H), 6.09-6.00 (m, 1H), 5.48 (dd, J=17.2 Hz, 1.2 Hz, 1H), 5.35 (dd, J=10.6 Hz, 1.4 Hz, 1H), 4.63-4.61 (m, 2H), 3.93 (s, 3H); [M+H]$^+$ 305.

Step 3: Methyl 4-allyl-5-bromo-2-chloro-3-hydroxybenzoate (Compound c31)

To a solution of methyl 3-(allyloxy)-5-bromo-2-chlorobenzoate (10.0 g, 32.7 mmol) in CH$_2$Cl$_2$ (150 mL) was added diisobutylaluminum chloride (25% in hexane, 64.0 mL) dropwise (0.5 to 1 h) at 0° C. under nitrogen atmosphere. The mixture was warmed up to room temperature slowly and additionally stirred at room temperature for 12 hours. The reaction mixture was cooled to 0° C. and quenched with 1 M HCl (50 mL), followed by extraction with EtOAc (150 mL×2). The combined organic layers were dried over MgSO$_4$, filtered, and concentrated in vacuo (9.9 g, 32.3 mmol, 99%). The crude residue was carried on to the next step without further purification to provide the title compound.

$^1$H NMR (400 MHz, CDCl$_3$) δ 7.23 (s, 1H), 6.20 (s, 1H), 5.96-5.86 (m, 1H), 5.11-5.07 (m, 2H), 3.92 (s, 3H), 3.65 (dt, J=5.4 Hz, 1.4 Hz, 2H); [M+H]$^+$ 305.

Step 4: Methyl 5-bromo-2-chloro-3-hydroxy-4-(2-hydroxyethyl)benzoate (Compound c33)

Method A) Synthesis Through Reduction of Aldehyde

To a mixture of methyl 4-allyl-5-bromo-2-chloro-3-hydroxybenzoate (9.9 g, 32.3 mmol) in THF/H$_2$O (100 mL/100 mL) was added NaIO$_4$ (20.8 g, 97.0 mmol) and OsO$_4$ (82 mg, 0.32 mmol) at 0° C. After stirring at 0° C. for 1 h, the reaction mixture was warmed up to room temperature and stirred at room temperature for 2 hours. The mixture was filtered to remove insoluble materials. The filtrate was poured into a saturated solution of Na$_2$S$_2$O$_3$ (100 mL) and the mixture was extracted with EtOAc (200 mL×2). The organic layer was dried over MgSO$_4$, filtered, and concentrated in vacuo (9.0 g, 29.4 mmol, 91%). The crude residue was carried on to the next step without further purification to provide methyl 5-bromo-2-chloro-3-hydroxy-4-(2-oxoethyl)benzoate (Compound c32). [M+H]$^+$ 307.

To solution of methyl 5-bromo-2-chloro-3-hydroxy-4-(2-oxoethyl)benzoate (20.1 g, 65.3 mmol) in THF (200 mL) was added NaBH$_4$ (2.72 g, 71.8 mmol) at 0° C. under nitrogen atmosphere. The reaction mixture was stirred at 0° C. for 2 hours. The mixture was quenched with saturated NH$_4$Cl (100 mL) and extracted with EtOAc (100 mL×2) [One extraction could not be enough]. The combined organic layers were dried over MgSO$_4$, filtered, and concentrated in vacuo (19.9 g). To a suspension of the residue in EtOAc (20 mL) was added hexane (10 to 20 mL). The resulting precipitate was collected by filtration and washed with hexane (50 mL). The precipitate was dried under high vacuum to provide the title compound (14.3 g, 72%).

$^1$H NMR (400 MHz, CDCl$_3$) δ 7.68 (s, 1H), 7.35 (s, 1H), 3.97-3.93 (m, 2H), 3.92 (s, 3H), 3.21 (t, J=6.2 Hz, 2H); [M+H]$^+$ 309.

Method B) Synthesis Through Ozonation Followed by Reduction

Ozone gas was bubbled through a methyl 4-allyl-5-bromo-2-chloro-3-hydroxybenzoate (10.2 g, 33.4 mmol, 80% purity) in CH$_2$Cl$_2$/MeOH (150 mL/35 mL) at −78° C. for 4 h (The solution color changed yellow to pale green). After stopping ozone addition, the reaction solution was purged with nitrogen until the green color is discharged (The solution color returned to yellow). Sodium borohydride (2.5 g, 66.8 mmol) was added as portionwise at −78° C. The resulting mixture was slowly warmed up to room temperature for 2 h, concentrated, suspended in EtOAc, and concentrated. To the residue, 1 N HCl aqueous solution (200 ml) was added, and stirred for 30 min. The precipitate was collected by filtration. (quantitative, 80% purity) The precipitate was suspended in EtOAc and stirred. To the resultant mixture, hexane was added slowly. The precipitate was obtained by filtration to provide the title compound (7.9 g, 76.4%, 92% purity).

$^1$H NMR (400 MHz, MeOD) δ 7.57 (s, 1H), 3.93 (s, 3H), 3.76 (t, J=7.24 Hz, 2H), 3.20 (t, J=7.28 Hz, 2H); [M+H]$^+$ 309.

Step 5: Methyl 4-bromo-7-chloro-2,3-dihydrobenzofuran-6-carboxylate (Compound c34)

Preparation of Vilsmeier reagent; To a solution of N,N-dimethylformamide (7.9 ml, 102.2 mmol) was added SOCl$_2$ (7.5 ml, 102.2 mmol) at room temperature. The reaction mixture was stirred for 2 hours at 40° C. The resulting mixture was concentrated in vacuo to provide hydroscopic white solid.

To a mixture of Vilsmeier reagent (13.08 g, 102.2 mmol) in DMF (100 mL) was slowly added methyl 5-bromo-2-chloro-3-hydroxy-4-(2-hydroxyethyl)benzoate (21.08 g, 68.10 mmol) in DMF (130 mL) at 0° C. The mixture was stirred for 1 h at 0° C. to 15° C. (gradiently warmed). The reaction mixture was quenched with triethylamine (38 ml, 272.4 mmol) in DMF (38 ml) at 0° C. After stirring for 10 min, the mixture was poured into water (1400 ml) at 0° C. and stirred for 2 hours at room temperature. The resulting precipitate was collected by filtration, washed with water and dried concentrated in vacuo to provide the title compound (13.0 g, 44.6 mmol, 65%) as a pale yellow solid.

$^1$H NMR (400 MHz, CDCl$_3$) δ 7.53 (s, 1H), 4.75 (t, J=8.8 Hz, 2H), 3.91 (s, 3H), 3.33 (t, J=8.8 Hz, 2H); [M+H]$^+$ 291.

Step 6: (4-Bromo-7-chloro-2,3-dihydrobenzofuran-6-yl)methanol (Compound c35)

To a mixture of methyl 4-bromo-7-chloro-2,3-dihydrobenzofuran-6-carboxylate (13.0 g, 44.7 mmol) in THF/EtOH (150 mL/75 mL) was slowly added sodium borohydride (5.07 g, 133.98 mmol) at room temperature. The mixture was stirred for 12 hours at room temperature. The resulting mixture was quenched with saturated NH$_4$Cl at 0° C. and extracted with EtOAc (aqueous pH∼7.0). The organic layer was dried over MgSO$_4$, filtered, and concentrated in vacuo to provide the title compound (11.7 g, 44.4 mmol, 99%) as a white solid. The crude product was used for the next step without further purification.

$^1$H NMR (400 MHz, CDCl$_3$) δ 7.15 (s, 1H), 4.73 (m, 4H), 3.29 (t, J=8.8 Hz, 2H), 1.91 (t, J=6.4 Hz, 1H); [M−H$_2$O]$^+$ 245.

Step 7: 4-Bromo-7-chloro-2,3-dihydrobenzofuran-6-carbaldehyde (Compound c36)

To a solution of (4-bromo-7-chloro-2,3-dihydrobenzofuran-6-yl)methanol (11.7 g, 44.4 mmol) in CH$_2$Cl$_2$ (450 ml) was slowly added PCC (14.4 g, 66.6 mmol, pyridinium chlorochromate) at room temperature. After stirring for 8 hours, precipitates were filtered off using Silica-gel pad and washed with $CH_2Cl_2$. The filtrate was concentrated in vacuo to provide the title compound (10.4 g, 39.8 mmol, 90%) as a white solid. The crude product was used for the next step without further purification.

$^1$H NMR (400 MHz, $CDCl_3$) δ 10.33 (s, 1H), 7.59 (s, 1H), 4.79 (t, J=8.8 Hz, 2H), 3.35 (t, J=8.8 Hz, 2H); $[M+H]^+$ 261.

Step 8: (4-Bromo-7-chloro-2,3-dihydrobenzofuran-6-yl)(4-cyclopropylphenyl)methanol (Compound c39)

Preparation of (4-cyclopropylphenyl)magnesium bromide (Compound c38); A 250 mL 3-neck-flask containing magnesium (turnings, 1.1 g, 46.6 mmol) was flame-dried. The flask was equipped with a condenser and an addition funnel under nitrogen atmosphere. 4-Cyclopropylphenyl bromide (PepTech, USA) (6.0 ml, 42.4 mmol) in anhydrous THF (32.4 mL) was transferred to the addition funnel. The Grignard reaction was initiated with approximately 5 mL of the 4-cyclopropylphenyl bromide solution. The remained bromide solution was added at room temperature for 4 hours. The resulting solution was used for next step directly.

To a solution of 4-bromo-7-chloro-2,3-dihydrobenzofuran-6-carbaldehyde (4.6 g, 17.6 mmol) in anhydrous THF (170 mL) was added a freshly prepared solution of (4-cyclopropylphenyl)magnesium bromide (Compound c38) (30.0 mL of 0.85 M in THF, 26.4 mmol) at 0° C. under nitrogen atmosphere. The reaction mixture was stirred at 0° C. for 30 min. The reaction mixture was quenched with water (100 mL) and extracted with EtOAc (100 mL). The organic layer was dried over $MgSO_4$, filtered, and concentrated in vacuo to provide the crude title product (7.6 g, 20.0 mmol, 114%). The crude residue was carried on to the next step without further purification to provide the crude title compound. $[M-H_2O]^+$ 361.

Step 9: 4-Bromo-7-chloro-6-(4-cyclopropylbenzyl)-2,3-dihydrobenzofuran (Compound c40)

To a solution of (4-bromo-7-chloro-2,3-dihydrobenzofuran-6-yl)(4-cyclopropylphenyl)methanol (7.6 g, 20.0 mmol) in $CH_2Cl_2$/$CH_3CN$ (100 mL/100 mL) were added triethylsilane (4.6 mL, 40 mmol) and boron trifluoride diethyl etherate (3.8 mL, 30 mmol) at −20° C. under nitrogen atmosphere. The mixture was gradually warmed up to room temperature and additionally stirred at room temperature for 50 min. The reaction mixture was quenched by slow addition of a saturated $NaHCO_3$ solution (200 mL) and extracted with EtOAc (100 mL). The organic layer was dried over $MgSO_4$, filtered, and concentrated in vacuo. The residue was purified by silica gel column chromatography to provide the title product (4.4 g, 12.1 mmol, 2 steps 85%).

$^1$H NMR (400 MHz, $CDCl_3$) δ 7.07 (d, J=8.0 Hz, 2H), 6.99 (d, J=8.0 Hz, 2H), 6.80 (s, 1H), 4.70 (t, J=8.8 Hz, 2H), 3.97 (s, 2H), 3.26 (t, J=8.8 Hz, 2H), 1.88-1.84 (m, 1H), 0.95-0.90 (m, 2H), 0.68-0.64 (m, 2H).

Step 10: (3R,4S,5R,6R)-2-(7-Chloro-6-(4-cyclopropylbenzyl)-2,3-dihydrobenzofuran-4-yl)-3,4,5-tris(trimethylsilyloxy)-6-((trimethylsilyloxy)methyl)tetrahydro-2H-pyran-2-ol (Compound c41)

To a solution of 4-bromo-7-chloro-6-(4-cyclopropylbenzyl)-2,3-dihydrobenzofuran (5.16 g, 14.2 mmol) in tetrahydrofuran (80 mL) was added dropwise n-butyllithium (2.5 M in hexanes, 7.38 mL, 18.4 mmol) at −78° C. under nitrogen atmosphere. After stirring for 40 to 60 min at the same temperature (yellowish solution), a pre-cooled (at −78° C.) solution of (3R,4S,5R,6R)-3,4,5-tris((trimethylsilyl)oxy)-6-(((trimethylsilyl)oxy)methyl)tetrahydro-2H-pyran-2-one (Compound a1; 8.6 g, 18.4 mmol) in tetrahydrofuran (20 mL) was added dropwise to the mixture by cannular for 20 min. The reaction mixture was stirred for 2 to 3 hours at the same temperature (yellowish solution).

The reaction mixture was quenched with 1% acetic acid (20 mL) at −78° C., and then evaporated under reduced pressure to remove volatiles. The aqueous residue was extracted with EtOAc (150 mL×2). The combined organic layers were dried over $MgSO_4$, filtered, and concentrated in vacuo to provide the crude title compound (11.8 g, quantitative) as pale yellow oil. The crude residue was carried on to the next step without further purification

Step 11: (3R,4S,5S,6R)-2-(7-Chloro-6-(4-cyclopropylbenzyl)-2,3-dihydrobenzofuran-4-yl)-6-(hydroxymethyl)-2-methoxytetrahydro-2H-pyran-3,4,5-triol (Compound c42)

To a solution of (3R,4S,5R,6R)-2-(7-chloro-6-(4-cyclopropylbenzyl)-2,3-dihydrobenzofuran-4-yl)-3,4,5-tris(trimethylsilyloxy)-6-((trimethylsilyloxy)methyl)tetrahydro-2H-pyran-2-ol; 11.8 g) in MeOH (150 mL) was added $CH_3SO_3H$ (1.5 mL, 23.5 mmol) at 0° C. by dropwise. The mixture was warmed up to rt over 18 hours, and then quenched with sat. $NaHCO_3$ at 0° C. The mixture was evaporated under reduced pressure to remove volatiles. The aqueous residue was extracted with EtOAc (100 mL×2). The combined organic layers were dried over $MgSO_4$, filtered and concentrated in vacuo to provide the crude title compound (6.0 g, 88% 2 steps) as a yellow solid. $[M+Na]^+$ 499 and $[M-OMe]^+$ 445.

Step 12: (3R,4R,5S,6R)-2-(7-Chloro-6-(4-cyclopropylbenzyl)-2,3-dihydrobenzofuran-4-yl)-6-(hydroxymethyl)tetrahydro-2H-pyran-3,4,5-triol (Compound c43)

To a stirred solution of (3R,4S,5S,6R)-2-(7-chloro-6-(4-cyclopropylbenzyl)-2,3-dihydrobenzofuran-4-yl)-6-(hydroxymethyl)-2-methoxytetrahydro-2H-pyran-3,4,5-triol (6.0 g, 12.6 mmol) in $CH_2Cl_2$/$CH_3CN$ (v:v=1:1, 120 mL) was added $Et_3SiH$ (6.0 mL, 37.8 mmol) followed by $BF_3OEt_2$ (3.2 mL, 25.2 mmol) at −50 to −45° C. by dropwise. The reaction mixture was warmed up to −10 to 0° C. over 3 to 3.5 hours prior to quenching with sat. $NaHCO_3$ (130 mL). The mixture was evaporated under reduced pressure to remove volatiles and the resulting residue was extracted with EtOAc (150 mL×2). The combined organic layers were dried over $MgSO_4$, filtered and concentrated in vacuo to provide the crude title compound (5.8 g, 12.9 mmol, 102%) as a yellow solid. $[M+Na]^+$ 469.

Step 13: (2R,3R,4R,5S,6S)-2-(Acetoxymethyl)-6-(7-chloro-6-(4-cyclopropylbenzyl)-2,3-dihydrobenzofuran-4-yl)tetrahydro-2H-pyran-3,4,5-triyl triacetate (Compound c27)

To a solution of (3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol (5.8 g, 12.9 mmol) in $CH_2Cl_2$ (120 mL) was added DMAP (1.9 g, 15.5 mmol) and $Ac_2O$ (9.7 mL, 103.76 mmol) at room temperature. After stirring for 18 hours at room temperature, the reaction was quenched with water (120 mL). The resulting mixture was extracted with CH$_2$Cl$_2$ (100 mL×2). After washing with 1 M HCl and brine, the combined organic layers were dried over MgSO$_4$, filtered and evaporated under reduced pressure (7.0 g, crude). The slurried residue in EtOH (45 mL) was heated at 80° C. to reflux for 1 h. The mixture was cooled to rt with stirring for 18 hours. The resulting precipitate was filtered, washed with EtOH and dried in vacuo to provide the title compound (4.7 g, 7.6 mmol, 59%) as a white solid.

$^1$H NMR (400 MHz, CDCl$_3$) δ 7.04-7.02 (m, 2H), 6.98-6.95 (m, 2H), 6.53 (s, 1H), 5.29-5.24 (m, 1H), 5.18-5.12 (m, 2H), 4.71-4.65 (m, 2H), 4.31-4.26 (m, 1H), 4.25-4.22 (m, 1H), 4.15-4.11 (m, 1H), 4.05-3.91 (m, 2H), 3.79-3.74 (m, 1H), 3.40-3.35 (m, 2H), 2.06 (s, 3H), 2.05 (s, 3H), 1.99 (s, 3H), 1.88-1.81 (m, 1H), 1.66 (s, 3H), 0.94-0.89 (m, 2H), 0.66-0.61 (m, 2H); [M+Na]$^+$ 637.

Step 14: (2S,3R,4R,5S,6R)-2-(7-Chloro-6-(4-cyclopropylbenzyl)-2,3-dihydrobenzofuran-4-yl)-6-(hydroxymethyl)tetrahydro-2H-pyran-3,4,5-triol (Compound c28)

To a solution of (2R,3R,4R,5S,6S)-2-(acetoxymethyl)-6-(7-chloro-6-(4-cyclopropylbenzyl)-2,3-dihydrobenzofuran-4-yl)tetrahydro-2H-pyran-3,4,5-triyl triacetate (1.5 g, 2.44 mmol) in THF/MeOH (5.4 mL/10.8 mL; 0.15 M) was added 4 M NaOH aqueous solution (2.8 mL). The reaction mixture was stirred at room temperature for 1.5 hours. The solution was cooled to 0° C. prior to neutralizing with 1 N HCl. The reaction solution was diluted with EtOAc and water. The organic layer was separated and the aqueous layer was extracted twice with EtOAc. The combined organic layers were dried over MgSO$_4$, filtered and concentrated in vacuo to provide the crude title compound.

A suspension of the crude title compound in toluene (8 mL) was heated at 40° C. for 30 min (sticky solution→clear solution→generation of white solid) and cooled to room temperature. The slurry was filtrated in filter funnel, and the cake was washed with 2 cake volumes of toluene. The wet cake was dried under vacuum to provide 1.0 g (2.24 mmol; quantitative) of the title compound.

A total yield of the final compound of Example 1 according to the synthetic pathway of the above steps 1 to 14 was calculated as about 12%.

$^1$H NMR (400 MHz, CD$_3$OD) δ 7.02 (d, J=8.0 Hz, 2H), 6.92 (d, J=8.0 Hz, 2H), 6.81 (s, 1H), 4.59 (t, J=8.8 Hz, 2H), 4.11 (d, J=9.2 Hz, 1H), 3.96 (ABq, Δv$_{AB}$=19.0 Hz, J$_{AB}$=15.2 Hz, 2H), 3.87-3.84 (m, 1H), 3.67-3.63 (m, 1H), 3.47-3.37 (m, 3H), 3.35-3.33 (m, 3H), 1.85-1.79 (m, 1H), 0.91-0.86 (m, 2H), 0.61-0.57 (m, 2H); [M+Na]$^+$ 469.

Example 2: Synthesis of (2S,3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol

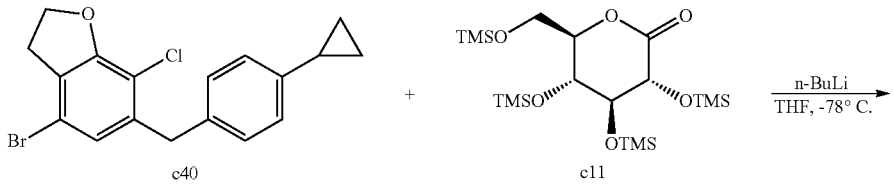

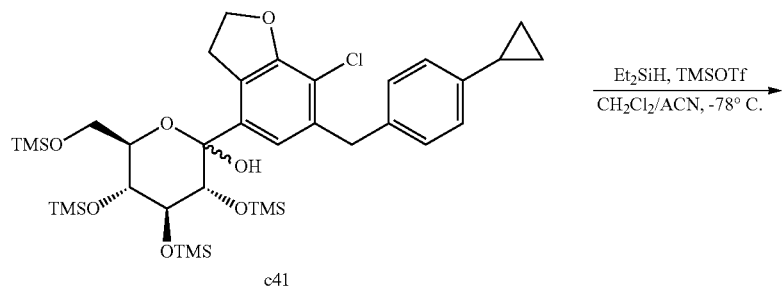

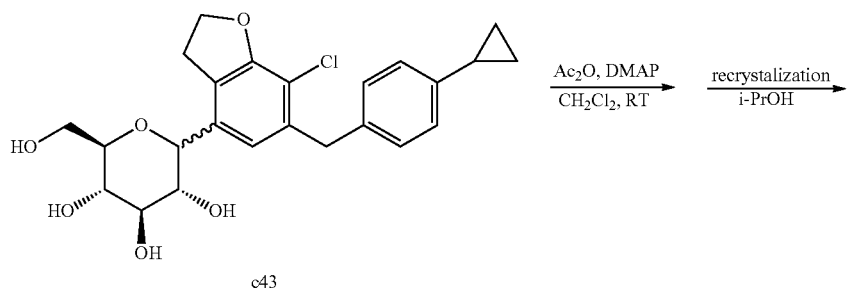

-continued

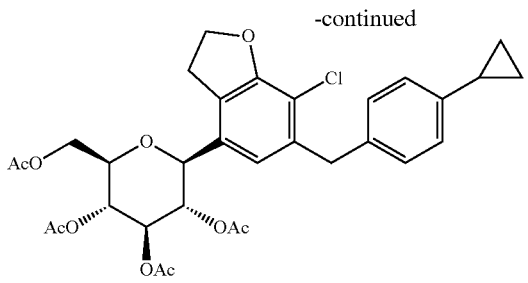

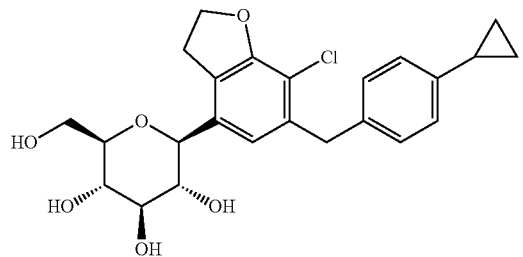

Step 1: (3R,4S,5R,6R)-2-(7-Chloro-6-(4-cyclopropylbenzyl)-2,3-dihydrobenzofuran-4-yl)-3,4,5-tris(trimethylsilyloxy)-6-((trimethylsilyloxy)methyl)tetrahydro-2H-pyran-2-ol (Compound c41)

To a solution of 4-bromo-7-chloro-6-(4-cyclopropylbenzyl)-2,3-dihydrobenzofuran (Compound c40, 5.00 g, 13.8 mmol) in tetrahydrofuran (140 mL) was added dropwise n-butyllithium (2.5 M in hexane, 8.28 mL, 20.7 mmol) at −78° C. under a nitrogen atmosphere. After performing stirring at the same temperature for 5 minutes, to the mixture was added dropwise a solution of TMS-protected lactone (Compound c11; 7.70 g, 16.6 mmol) in tetrahydrofuran for 30 minutes. The reaction mixture was stirred at the same temperature for 1 hour. The reaction mixture was quenched with a saturated NH$_4$Cl aqueous solution (300 mL) at 0° C., and extraction with EtOAc was performed. The organic layer was dried over Na$_2$SO$_4$, filtered, and concentrated in vacuo to obtain the crude title compound (10.3 g, quantitative) as yellow oil. The crude residue was used in the next step without further purification.

Step 2: (3R,4R,5S,6R)-2-(7-Chloro-6-(4-cyclopropylbenzyl)-2,3-dihydrobenzofuran-4-yl)-6-(hydroxymethyl)tetrahydro-2H-pyran-3,4,5-triol (Compound c43)

To crude (3R,4S,5R,6R)-2-(7-chloro-6-(4-cyclopropylbenzyl)-2,3-dihydrobenzofuran-4-yl)-3,4,5-tris(trimethylsilyloxy)-6-((trimethylsilyloxy)methyl)tetrahydro-2H-pyran-2-ol (10.3 g) in CH$_2$Cl$_2$ (70 mL) and CH$_3$CN (70 mL) was added triethylsilane (8.8 mL, 55.2 mmol) and TMSOTf (10 mL, 55.2 mmol) at −78° C. After performing stirring at −78° C. for 1 hour, the reaction mixture was quenched with water (200 mL) at 0° C., and extraction with CH$_2$Cl$_2$ (300 mL) was performed. The organic layer was dried over Na$_2$SO$_4$, filtered, and concentrated in vacuo to obtain the crude title compound (6.3 g, quantitative) as yellow oil. The crude residue was used in the next step without further purification.

Step 3: (2R,3R,4R,5S,6S)-2-(Acetoxymethyl)-6-(7-chloro-6-(4-cyclopropylbenzyl)-2,3-dihydrobenzofuran-4-yl)tetrahydro-2H-pyran-3,4,5-triyl triacetate (Compound c27)

To a solution of (3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol (6.3 g, 13.8 mmol) in CH$_2$CL$_2$ (140 mL) was added DMAP (0.84 g, 6.9 mmol) and Ac$_2$O (13.0 mL, 13.8 mmol) at room temperature. After performing stirring at room temperature for 18 hours, the reaction mixture was quenched with water (120 mL), and extraction with DCM (200 mL) was performed. The organic layer was washed with a NaHCO$_3$ aqueous solution (100 mL), dried over Na$_2$SO$_4$, filtered, and concentrated in vacuo. The slurried residue in isopropyl alcohol (20 mL) was heated at 80° C. for 10 minutes and cooled to room temperature. Then, the resulting precipitate was filtered and concentrated in vacuo to obtain the title compound (4.52 g, 7.35 mmol, 53%) in a β-form as a white solid.

$^1$H NMR (400 MHz, CDCl$_3$) δ 7.04-7.02 (m, 2H), 6.98-6.95 (m, 2H), 6.53 (s, 1H), 5.29-5.24 (m, 1H), 5.18-5.12 (m, 2H), 4.71-4.65 (m, 2H), 4.31-4.26 (m, 1H), 4.25-4.22 (m, 1H), 4.15-4.11 (m, 1H), 4.05-3.91 (m, 2H), 3.79-3.74 (m, 1H), 3.40-3.35 (m, 2H), 2.06 (s, 3H), 2.05 (s, 3H), 1.99 (s, 3H), 1.88-1.81 (m, 1H), 1.66 (s, 3H), 0.94-0.89 (m, 2H), 0.66-0.61 (m, 2H); [M+Na]+ 637.

Step 4: (2S,3R,4R,5S,6R)-2-(7-Chloro-6-(4-cyclopropylbenzyl)-2,3-dihydrobenzofuran-4-yl)-6-(hydroxymethyl)tetrahydro-2H-pyran-3,4,5-triol (Compound c28)

To a solution of (2R,3R,4R,5S,6S)-2-(acetoxymethyl)-6-(7-chloro-6-(4-cyclopropylbenzyl)-2,3-dihydrobenzofuran-4-yl)tetrahydro-2H-pyran-3,4,5-triyl triacetate (4.52 g, 7.35 mmol) in MeOH (70 mL) was added NaOMe (25 wt %, 0.35 mL). After performing stirring at room temperature for 18 hours, the reaction mixture was concentrated in vacuo, diluted with water (200 mL), and extracted with EtOAc (300 mL). The organic layer was dried over Na$_2$SO$_4$, filtered, and concentrated in vacuo. The residue was purified by recrystallization in toluene to obtain the title compound (3.16 g, 96%) in a β-form as yellow solid.

$^1$H NMR (400 MHz, CD$_3$OD) δ 7.02 (d, J=8.0 Hz, 2H), 6.92 (d, J=8.0 Hz, 2H), 6.81 (s, 1H), 4.59 (t, J=8.8 Hz, 2H), 4.11 (d, J=9.2 Hz, 1H), 3.96 (ABq, ΔvAB=19.0 Hz, JAB=15.2 Hz, 2H), 3.87-3.84 (m, 1H), 3.67-3.63 (m, 1H), 3.47-3.37 (m, 3H), 3.35-3.33 (m, 3H), 1.85-1.79 (m, 1H), 0.91-0.86 (m, 2H), 0.61-0.57 (m, 2H); [M+Na]+469.

Example 3: Synthesis of (2S,3R,4R,5S,6R)-2-(7-chloro-6-(4-methoxybenzyl)-2,3-dihydrobenzofuran-4-yl)-6-(hydroxymethyl)tetrahydro-2H-thiopyran-3,4,5-triol

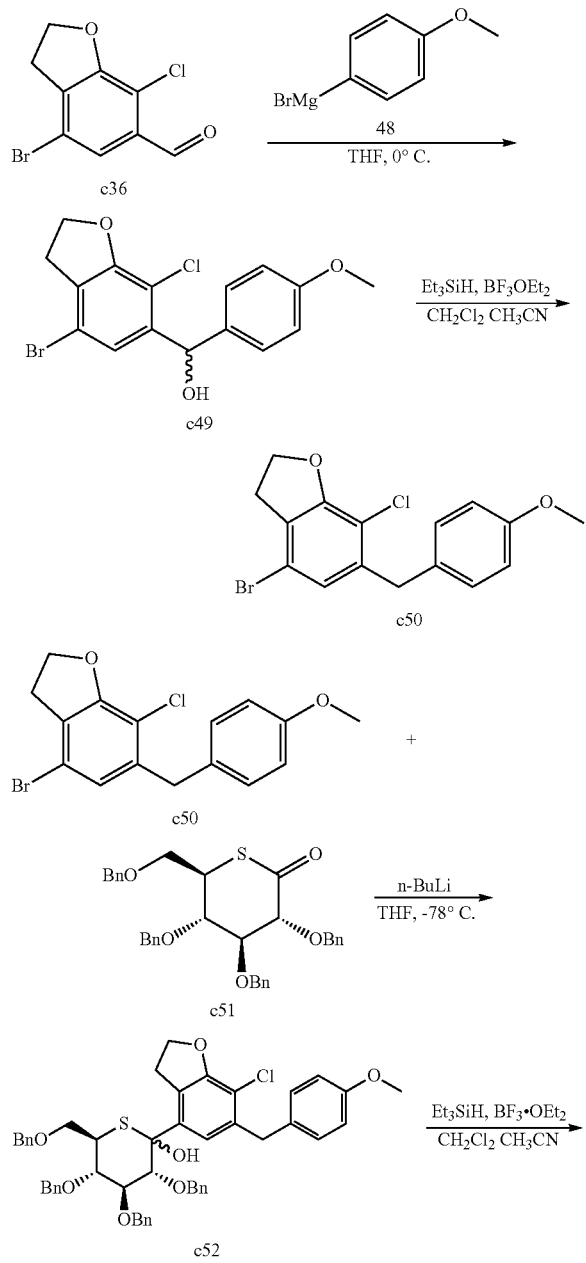

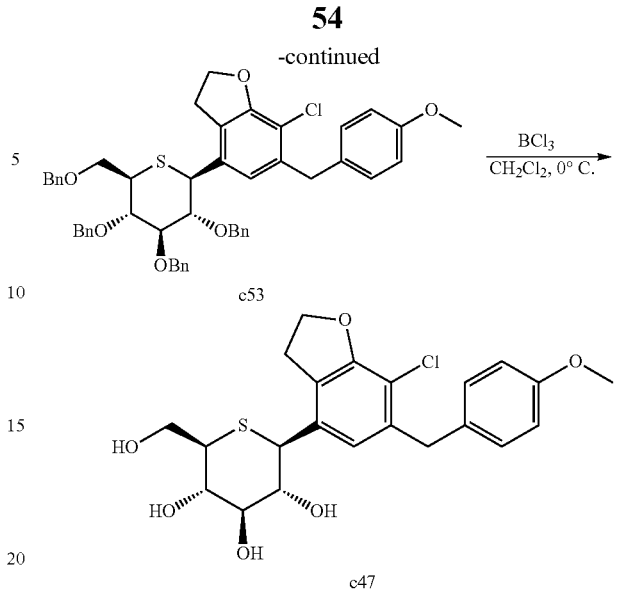

Step 1: (3R,4S,5S,6R)-3,4,5-tris(benzyloxy)-6-((benzyloxy)methyl)-2-(7-chloro-6-(4-methoxybenzyl)-2,3-dihydrobenzofuran-4-yl)tetrahydro-2H-thiopyran-2-ol (Compound c52)

The synthesis procedure of step 8 in Example 4 was repeated except that 4-bromo-7-chloro-2,3-dihydrobenzofuran-6-carbaldehyde was used as a starting material and (4-methoxyphenyl)magnesium bromide (Compound c48) was used as a Grignard reagent to provide (4-bromo-7-chloro-2,3-dihydrobenzofuran-6-yl)(4-methoxyphenyl)methanol (Compound c49). Then the synthesis procedure of step 9 in Example 4 was repeated except that (4-bromo-7-chloro-2,3-dihydrobenzofuran-6-yl)(4-methoxyphenyl)methanol (Compound c49) was used as a starting material to provide 4-bromo-7-chloro-6-(4-methoxybenzyl)-2,3-dihydrobenzofuran (Compound c50).

To a solution of 4-bromo-7-chloro-6-(4-methoxybenzyl)-2,3-dihydrobenzofuran (Compound c50, 859 mg, 2.43 mmol) in tetrahydrofuran (8 mL) at −78° C. under an atmosphere of nitrogen was added dropwise n-butyllithium (2.5 M in hexane, 1.3 mL, 3.24 mmol), and the mixture was stirred for 1.5 hours at the same temperature. Then a solution of (3R,4S,5S,6R)-3,4,5-tris(benzyloxy)-6-((benzyloxy)methyl)tetrahydro-2H-thiopyran-2-one (Compound c51, 898 mg, 1.62 mmol. This compound was synthesized by reference to H. Driguez and B. Henrissat, Tetrahedron Lett. 1981, 22, 5061-5062, Kakinuma, H., et al., J. Med. Chem. 2010, 53, 3247-3261) in tetrahydrofuran (4 mL) was added dropwise, and the mixture was stirred for 1.5 hours at the same temperature. The reaction mixture was quenched by addition of saturated ammonium chloride solution. After complete addition, the solution was gradually raised to room temperature. The organic layer was separated and the aqueous layer was extracted with ethyl acetate. The combined organic layers were washed with brine, dried over magnesium sulfate, filtered and concentrated in vacuo to provide the crude compound (3R,4S,5S,6R)-3,4,5-tris(benzyloxy)-6-((benzyloxy)methyl)-2-(7-chloro-6-(4-methoxybenzyl)-2,3-dihydrobenzofuran-4-yl)tetrahydro-2H-thiopyran-2-ol (quantitative yield).

Step 2: 7-chloro-6-(4-methoxybenzyl)-4-((2S,3R, 4R,5S,6R)-3,4,5-tris(benzyloxy)-6-((benzyloxy) methyl)tetrahydro-2H-thiopyran-2-yl)-2,3-dihydrobenzofuran (Compound c53)

To a stirred at −20° C. solution of lactol (c52) in dichloromethane (16 mL) was added triethylsilane (1.6 mL, 9.72 mmol) followed by boron trifluoride diethyl etherate (0.8 mL, 6.48 mmol) at a rate such that the reaction temperature was maintained between −20 and 0° C. The solution was allowed to warm to 0° C. over 1.5 hours prior to quenching with saturated sodium bicarbonate solution. After removal of organic volatiles under reduced pressure, the residue was partitioned between ethyl acetate and water. Following extraction of the aqueous layer with ethyl acetate, the combined organic layers were washed with brine, dried over magnesium sulfate, filtered and concentrated in vacuo. The crude residue was purified by silica gel chromatography (silica gel, 3 to 25% ethyl acetate in hexane) to provide the crude compound 7-chloro-6-(4-methoxybenzyl)-4-((2S,3R, 4R,5S,6R)-3,4,5-tris(benzyloxy)-6-((benzyloxy)methyl)tetrahydro-2H-thiopyran-2-yl)-2,3-dihydrobenzofuran (603 mg, 46%, 2 steps) as a white solid. [M+Na]+ 835.

Step 3: (2S,3R,4R,5S,6R)-2-(7-Chloro-6-(4-methoxybenzyl)-2,3-dihydrobenzofuran-4-yl)-6-(hydroxymethyl)tetrahydro-2H-thiopyran-3,4,5-triol (Compound c47)

To a solution of 7-chloro-6-(4-methoxybenzyl)-4-((2S, 3R,4R,5S,6R)-3,4,5-tris(benzyloxy)-6-((benzyloxy)methyl) tetrahydro-2H-thiopyran-2-yl)-2,3-dihydrobenzofuran (c53, 570 mg, 0.70 mmol) in dichloromethane (8 mL) was added $BCl_3$ (1.0 M in dichloromethane, 2.8 mL) at 0° C. The reaction mixture was stirred at 0° C. for 1 hour. After quenching the reaction with methanol, solvent was evaporated under reduced pressure. Purification by reverse phase preparative HPLC (Gilson, SunFire™ Prep, 5 to 50% acetonitrile in water gradient) provided the title compound (18 mg, 6%) as a white solid.

$^1$H NMR (400 MHz, $CD_3OD$) δ 7.07 (d, J=8.4 Hz, 2H), 6.79 (d, J=8.8 Hz, 2H), 6.76 (s, 1H), 4.63 (td, J=8.0, 1.6 Hz, 2H), 3.95 (s, 2H), 3.92 (d, J=3.6 Hz, 1H), 3.79-3.75 (m, 3H), 3.74 (s, 3H), 3.71 (d, J=6.4 Hz, 1H), 3.56 (dd, J=10.0, 8.8 Hz, 1H), 3.42-3.35 (m, 2H), 3.24-3.20 (m, 1H), 3.01-2.96 (m, 1H), 0.90 (t, J=7.2 Hz, 3H); [M+Na]+ 475.

Example 4: Production of (2S,3R,4R,5S,6R)-2-(7-chloro-6-(4-ethoxybenzyl)-2,3-dihydrobenzofuran-4-yl)-6-(methylthio)tetrahydro-2H-pyran-3,4,5-triol

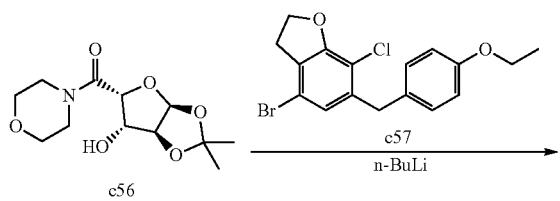

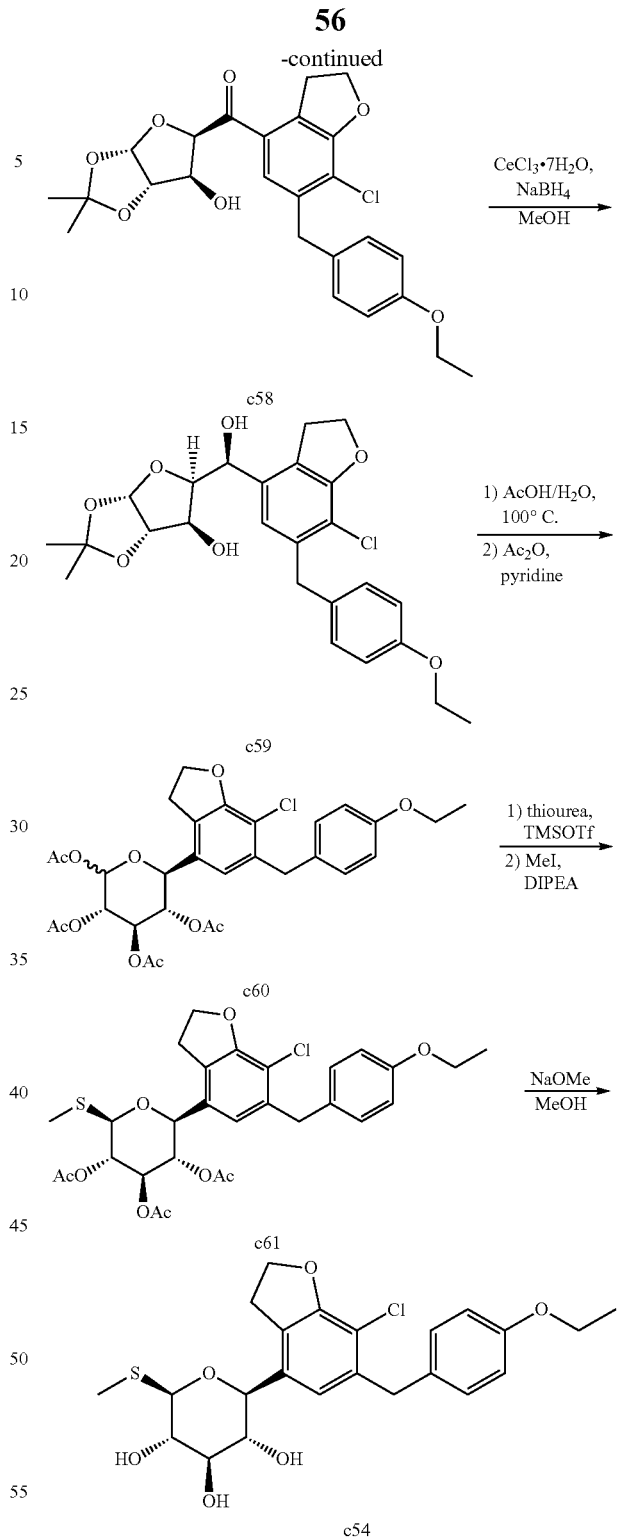

Step 1: ((3aS,5S,6R,6aS)-5-(Hydroxymethyl)-2,2-dimethyltetrahydrofuro[3,2-d][1,3]dioxol-6-ol To a suspension of L-(−)-xylose (19.15 g, 127.5 mmol) and $MgSO_4$ (30.72 g, 255.0 mmol) in acetone (190 mL) was added concentrated $H_2SO_4$ (1.9 mL) at room temperature. After 12 hours, the reaction mixture (in which all L-(−)-xylose had been consumed) was filtered and the combined solid was washed twice with acetone (20 mL per wash). The yellow filtrate was neutralized to about pH 9 with a NH$_4$OH solution while performing stirring. The suspended solid was removed by filtration. The filtrate was concentrated to obtain a bis-acetonide intermediate as yellow oil. The yellow oil was suspended in water (5 mL), and then the pH was adjusted from 9 to 2 with a 1 N HCl solution in water. The reaction mixture was stirred at room temperature for 12 hours. The resulting mixture was neutralized by addition of 25% (w/w) K$_3$PO$_4$ in water until the pH became about 7. The mixture was extracted with EtOAc. The organic layer was dried over MgSO$_4$, filtered, and concentrated in vacuo. The crude product was purified by silica gel column chromatography to obtain the title compound (12.63 g, 52%) as yellow oil.

$^1$H NMR (400 MHz, CD$_3$OD) δ 5.88 (d, J=4.0 Hz, 1H), 4.47 (d, J=4.0 Hz, 1H), 4.18-4.14 (m, 1H), 4.11 (d, J=2.8 Hz, 1H), 3.83-3.71 (m, 2H), 1.45 (s, 3H), 1.29 (s, 3H).

Step 2: (3aS,5R,6S,6aS)-6-Hydroxy-2,2-dimethyl-tetrahydrofuro[3,2-d][1,3]dioxole-5-carboxylic acid To a solution of ((3aS,5S,6R,6aS)-5-(hydroxymethyl)-2,2-dimethyltetrahydrofuro[3,2-d][1,3]dioxol-6-ol (14.6 g, 76.7 mmol), NaHCO$_3$ (19.3 g, 230.3 mmol), and NaBr (1.6 g, 15.4 mmol) in acetone/water (120 mL/40 mL) was added TEMPO (0.24 g, 1.5 mmol) at room temperature. The mixture was cooled to 0° C., and then trichloroisocyanuric acid (17.8 g, 76.7 mmol) was added in small portions. The suspension was stirred at room temperature for 12 hours. Methanol (2.0 mL) was added and the mixture was stirred at room temperature for 2 hours. The mixture was filtered and washed with acetone (twice, 20 mL per wash). The organic solvent was removed in vacuo, the aqueous layer was extracted with EtOAc, and the organic layer was concentrated in vacuo. Acetone was added thereto and the mixture was filtered. The filtrate was concentrated to obtain the desired acid (9.0 g, 58%) as a light yellow solid.

$^1$H NMR (400 MHz, CD$_3$OD) δ 5.98 (d, J=3.6 Hz, 1H), 4.71 (d, J=3.2 Hz, 1H), 4.51 (d, J=3.6 Hz, 1H), 4.36 (d, J=3.6 Hz, 1H), 1.45 (s, 3H), 1.31 (s, 3H).

Step 3: ((3aS,5R,6S,6aS)-6-Hydroxy-2,2-dimethyl-tetrahydrofuro[3,2-d][1,3]dioxol-2-yl)(morpholino)methanone (Compound c56)

To a suspension of (3aS,5R,6S,6aS)-6-hydroxy-2,2-dimethyltetrahydrofuro[3,2-d][1,3]dioxole-5-carboxylic acid (9.0 g, 44.2 mmol) and HBTU (25.1 g, 66.3 mmol, N,N,N',N'-tetramethyl-O-(1H-benzotriazol-1-yl)uronium hexafluorophosphate) in tetrahydrofuran was added 4-methylmorpholine (7.3 mL, 66.3 mmol) at room temperature. After 1 hour, to the mixture was added morpholine (5.8 mL, 66.3 mmol) at room temperature. After 12 hours, the resulting mixture was filtered and the filter cake was washed with tetrahydrofuran. The filtrate was concentrated in vacuo and the crude material was purified by silica gel column chromatography to obtain the title compound (5.8 g, 48%) as a yellow solid.

$^1$H NMR (400 MHz, CD$_3$OD) δ 6.01 (d, J=3.6 Hz, 1H), 5.10 (s, 1H), 4.59 (d, J=2.4 Hz, 1H), 4.57 (d, J=3.6 Hz, 1H), 4.47 (d, J=2.4 Hz, 1H), 3.85-3.62 (m, 6H), 3.53-3.49 (m, 2H), 1.49 (s, 3H), 1.33 (s, 3H). [M+H]$^+$ 274.

Step 4: (7-Chloro-6-(4-ethoxybenzyl)-2,3-dihydrobenzofuran-4-yl)((3aS,5R,6S,6aS)-6-hydroxy-2,2-dimethyltetrahydrofuro[2,3-d][1,3]dioxol-5-yl)methanone (Compound c58)

To a solution of 4-bromo-7-chloro-6-(4-ethoxybenzyl)-2,3-dihydrobenzofuran (Compound c57, 0.7 g, 1.90 mmol) in THF (17.5 mL) was added n-BuLi (2.5 M solution in hexane, 0.9 mL, 2.28 mmol) at −78° C. After 1 hour, to the mixture was added dropwise ((3aS,5R,6S,6aS)-6-hydroxy-2,2-dimethyltetrahydrofuro[3,2-d][1,3]dioxol-5-yl)(morpholino)methanone (Compound c56, 0.17 g, 0.63 mmol) in THF (8.0 mL) at −78° C. After 4 hours, the resulting mixture was quenched with a saturated NH$_4$Cl solution, and extraction with EtOAc was performed. The organic layer was dried over MgSO$_4$, filtered, and concentrated in vacuo. The crude product was purified by silica gel column chromatography (Biotage Isolera™ FLASH Purification System) to obtain the title compound (0.13 g, 43%); [M+H]$^+$ 475.

Step 5: (3aS,5S,6R,6aS)-5-((S)-(7-Chloro-6-(4-ethoxybenzyl)-2,3-dihydrobenzofuran-4-yl)(hydroxyl)methyl)-2,2-dimethyltetrahydrofuro[2,3-d][1,3]dioxol-6-ol (Compound c59)

To a solution of (7-chloro-6-(4-ethoxybenzyl)-2,3-dihydrobenzofuran-4-yl)((3aS,5R,6S,6aS)-6-hydroxy-2,2-dimethyltetrahydrofuran[2,3-d][1,3]dioxol-5-yl)methanone (0.13 g, 0.27 mmol) in methanol (18 mL) was added CeCl$_3$.7H$_2$O (0.12 g, 0.32 mmol), and the mixture was stirred at room temperature until all solids were dissolved. Then, the mixture was cooled to −78° C. and NaBH$_4$ (0.012 g, 0.32 mmol) was added in small portions. The mixture was stirred at −78° C. for 2 hours, slowly warmed to 0° C., and quenched with a saturated NH$_4$Cl solution. The mixture was concentrated under reduced pressure to remove CH$_3$OH, extracted with EtOAc, and washed with a saturated NaCl solution. The organic layer was dried over MgSO$_4$, filtered, and concentrated in vacuo. The crude title compound was dried under high vacuum and used in the next step as a white solid (0.13 g) without purification.

[M+Na]$^+$ 499.

Step 6: (3S,4R,5S,6S)-6-(7-Chloro-6-(4-ethoxybenzyl)-2,3-dihydrobenzofuran-4-yl)tetrahydro-2H-pyran-2,3,4,5-tetrayl tetraacetate (Compound c60)

A solution of (3aS,5S,6R,6aS)-5-((S)-(7-chloro-6-(4-ethoxybenzyl)-2,3-dihydrobenzofuran-4-yl)(hydroxyl)methyl)-2,2-dimethyltetrahydrofuro[2,3-d][1,3]dioxol-6-ol (0.13 g, 0.27 mmol) in AcOH/water (4.0/2.5 mL) was stirred at 100° C. for 12 hours. The resulting mixture was cooled to room temperature and concentrated under reduced pressure. The crude oil was treated with acetic anhydride (0.2 mL, 2.16 mmol) in pyridine (0.7 mL) at 0° C. The mixture was stirred at room temperature for 8 hours. The resulting mixture was quenched with water, extraction with EtOAc was performed, and washing with brine was performed. The organic layer was dried over MgSO$_4$, filtered, and concentrated in vacuo. The residue was purified by silica gel column chromatography to obtain the title compound (0.16 g, 96%) as a white solid. [M+Na]$^+$ 627.

Step 7: (2S,3S,4R,5S,6R)-2-(7-Chloro-6-(4-ethoxybenzyl)-2,3-dihydrobenzofuran-4-yl)-6-(methylthio)tetrahydro-2H-pyran-3,4,5-triyl triacetate (Compound c61)

To a solution of (3S,4R,5S,6S)-6-(7-chloro-6-(4-ethoxybenzyl)-2,3-dihydrobenzofuran-4-yl)tetrahydro-2H-pyran-2,3,4,5-tetrayl tetraacetate (160 mg, 0.26 mmol) and thiourea (39 mg, 0.52 mmol) in 1,4-dioxane (3.1 mL) was added TMSOTf (70 μl, 0.39 mmol), and the reaction mixture was heated at 80° C. for 4 hours. The mixture was cooled to room temperature, MeI (40 μl, 0.65 mmol) and DIPEA (452 μl, 2.60 mmol) were added thereto, and stirring was performed for 3 hours. The resulting mixture was diluted with EtOAc and washed with water. The organic layer was dried over MgSO₄, filtered, and concentrated in vacuo. The crude title compound was dried under high vacuum and used in the next step as a white solid (150 mg, 48%) without purification. [M+Na]⁺ 615.

Step 8: (2S,3R,4R,5S,6R)-2-(7-Chloro-6-(4-ethoxybenzyl)-2,3-dihydrobenzofuran-4-yl)-6-(methylthio)tetrahydro-2H-pyran-3,4,5-triol (Compound c54)

To a suspension of (2S,3S,4R,5S,6R)-2-(7-chloro-6-(4-ethoxybenzyl)-2,3-dihydrobenzofuran-4-yl)-6-(methylthio)tetrahydro-2H-pyran-3,4,5-triyl triacetate (150 mg, 0.25 mmol) in CH₃OH (0.7 mL) was added NaOMe (catalytic amount, 25% solution in CH₃OH) at room temperature. After 20 hours, the resulting mixture was concentrated in vacuo. The crude product was diluted with EtOAc and filtered through a membrane. The crude product was purified by preparative HPLC (Gilson system, CH₃CN/H₂O) to obtain the title compound (41 mg, 35%).
¹H NMR (400 MHz, CDCl₃) δ 7.09 (d, J=8.4 Hz, 2H), 6.80 (d, J=8.8 Hz, 2H), 6.68 (s, 1H), 4.69-4.64 (m, 2H), 4.35 (d, J=10.0 Hz, 1H), 4.20 (d, J=9.2 Hz, 1H), 4.02-3.88 (m, 4H), 3.67-3.65 (m, 2H), 3.61-3.58 (m, 1H), 3.56-3.52 (m, 1H), 3.42-3.40 (m, 2H), 3.29-3.27 (m, 2H), 2.17 (s, 3H), 1.40 (t, J=7.0 Hz, 3H); [M+Na]⁺ 489.

Example 5: Production of (2S,3R,4R,5S,6R)-2-(7-chloro-6-(4-ethylbenzyl)-2,3-dihydrobenzofuran-4-yl)-6-(methylthio)tetrahydro-2H-pyran-3,4,5-triol The title compound was obtained by repeating the synthesis procedure of Example 4 except that 4-bromo-7-chloro-6-(4-ethylbenzyl)-2,3-dihydrobenzofuran was used in place of 4-bromo-7-chloro-6-(4-ethoxybenzyl)-2,3-dihydrobenzofuran in the step 4.
¹H NMR (400 MHz, CDCl₃) δ 7.10-7.90 (m, 4H), 6.71 (s, 1H), 4.68-4.62 (m, 2H), 4.33 (d, J=9.6 Hz, 1H), 4.18 (d, J=9.2 Hz, 1H), 4.07-4.00 (m, 2H), 3.63-3.57 (m, 3H), 3.52-3.49 (m, 1H), 3.39-3.37 (m, 2H), 3.27-3.25 (m, 2H), 2.60 (q, J=7.4 Hz, 2H), 2.15 (s, 3H), 1.20 (t, J=7.6 Hz, 3H); [M+Na]⁺ 473.

Example 6: Production of (2S,3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol

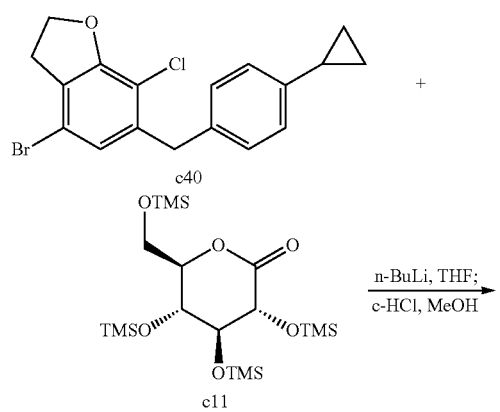

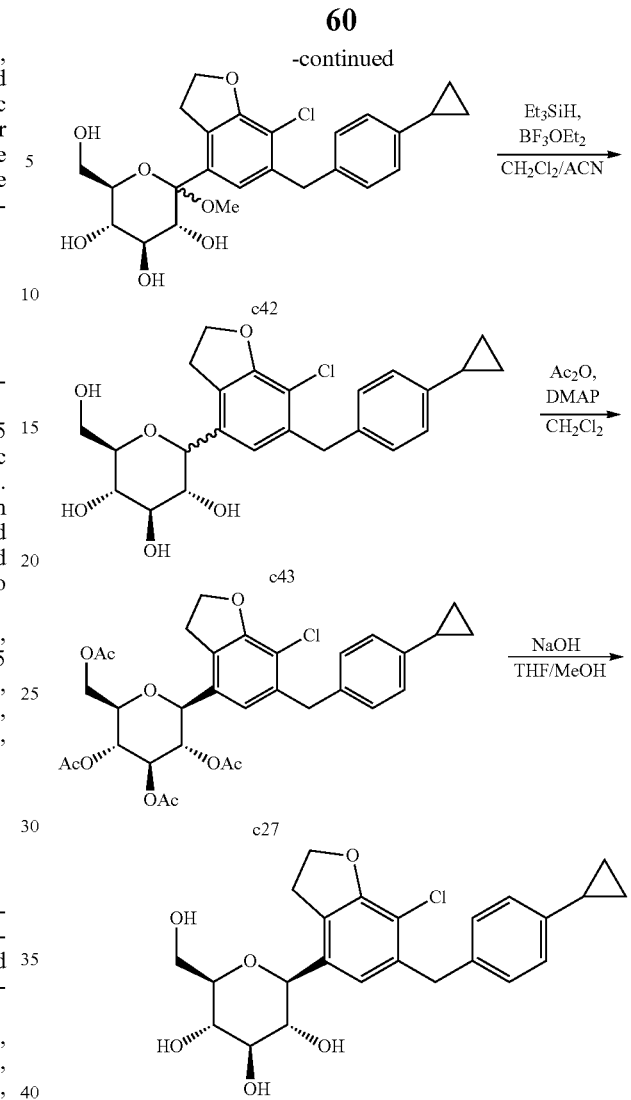

Step 1: (3R,4S,5S,6R)-2-[7-Chloro-6-(4-cyclopropylbenzyl)-2,3-dihydrobenzofuran-4-yl])-6-(hydroxymethyl)-2-methoxytetrahydro-2H-pyran-3,4,5-triol (Compound c42)

The title compound was synthesized via the following pathway of 1a or 1b.

(1a) To a reaction vessel were added dropwise 4-bromo-7-chloro-6-(4-cyclopropylbenzyl)-2,3-dihydrobenzofuran (250 g, 0.687 mol), (3R,4S,5R,6R)-3,4,5-tris((trimethylsilyl)oxy)-6-(((trimethylsilyl)oxy)methyl)tetrahydro-2H-pyran-2-one (642 g, 1.38 mol), and anhydrous tetrahydrofuran (2.00 L) at room temperature under nitrogen, and the mixture was completely dissolved. After the reaction vessel was cooled to −78° C., n-butyllithium (550 mL, 2.0 M in hexane, 1.38 mol) was added dropwise thereto for 1 hour while keeping the internal temperature at −60° C. or lower. Once the dropwise addition of n-butyllithium was complete, the mixture was further stirred at −78° C. for 40 minutes. To the reaction mixture was added dropwise a concentrated hydrochloric acid/methanol (152 mL/1,750 mL) solution for 20 minutes while keeping the internal temperature at −30° C. or lower. Once the dropwise addition was complete, the reaction vessel was moved to room temperature and stirred for 18 hours. After confirming completion of the reaction, the reaction vessel was cooled to 0° C., a saturated NaHCO$_3$ aqueous solution (2.5 L) was added thereto, the pH was adjusted to 9 to 10 using a pH meter, and then the reaction solvent was removed using a vacuum concentrator. The concentrate was diluted with EtOAc (2.5 L), distilled water (1.25 L), and brine (1.25 L), and layered. Then, the organic layers were pooled and the aqueous layer was extracted with EtOAc (2×1.25 L). The organic layers were combined and rinsed with distilled water (2.5 L) and brine (2.5 L). The organic layer was dried over MgSO$_4$ (50 g) and filtered. Then, the filtrate was concentrated under reduced pressure to remove the solvent. An operation of diluting the residue with toluene (500 mL) and performing removal by distillation under reduced pressure was repeated twice to obtain the title compound (328 g) as a yellow liquid. The crude residue was used in the next step without further purification.

(1b) To a reaction vessel were added dropwise 4-bromo-7-chloro-6-(4-cyclopropylbenzyl)-2,3-dihydrobenzofuran (10.0 g, 27.5 mol), (3R,4S,5R,6R)-3,4,5-tris((trimethylsilyl)oxy)-6-(((trimethylsilyl)oxy)methyl)tetrahydro-2H-pyran-2-one (25.7 g, 54.9 mol) and anhydrous tetrahydrofuran (80 mL) at room temperature under nitrogen, and the mixture was completely dissolved. After the reaction vessel was cooled to −78° C., n-butyllithium (22.1 mL, 2.5 M in hexane, 54.9 mmol) was added dropwise thereto for 15 minutes while keeping the internal temperature at −60° C. or lower. Once the dropwise addition of n-butyllithium was complete, the mixture was further stirred at −78° C. for 30 minutes. To the reaction mixture was added dropwise a concentrated hydrochloric acid/methanol (7.01 mL/70 mL) solution for 10 minutes while keeping the internal temperature at −30° C. or lower. Once the dropwise addition was complete, the reaction vessel was moved to room temperature and stirred for 18 hours. After confirming completion of the reaction, the reaction vessel was cooled to 0° C., a saturated NaHCO$_3$ aqueous solution (60 mL) was added thereto, the pH was adjusted to 9 to 10 using a pH meter, and then the reaction solvent was removed using a vacuum concentrator. The concentrate was diluted with EtOAc (60 mL), distilled water (60 mL), and brine (60 mL), and layered. Then, the organic layers were pooled and the aqueous layer was extracted with EtOAc (2×30 mL). The organic layers were combined and rinsed with distilled water (60 mL) and brine (60 mL). The organic layer was dried over MgSO$_4$ (5 g), filtered, and the filtrate was concentrated under reduced pressure to remove the solvent. The residue was diluted with toluene (50 mL), and then the toluene solution was slowly added dropwise to hexane (200 mL) at room temperature while stirring the hexane. The resulting suspension was stirred at the same temperature for 1 hour and then filtered in vacuo. The resulting filtrate was washed with hexane (10 mL), and then dried in a vacuum oven (40° C.) until a moisture content thereof became 1% or lower through a Karl-Fischer analysis, to obtain the title compound (12.6 g, 96%) as a yellow solid.

$^1$H NMR (500 MHz, CDCl$_3$): δ 7.02 (d, J=8.0 Hz, 2H), 6.92 (d, J=8.0 Hz, 2H), 6.81 (s, 1H), 4.64 (m, 1H), 4.57 (m, 1H), 4.05 (d, J=15.0 Hz, 1H), 3.96 (d, J=15.0 Hz, 1H), 3.93 (dd, J=11.8, 3.0 Hz, 1H), 3.87 (m, 2H), 3.65 (m, 2H), 3.51 (m, 1H), 3.30 (d, J=9.5 Hz, 1H), 3.14 (s, 3H), 1.83 (m, 1H), 0.91 (m, 2H), 0.63 (m, 2H); LC-MS: [M-OMe]$^+$ 445.

Step 2: (3R,4S,5R,6R)-2-[7-Chloro-6-(4-cyclopropylbenzyl)-2,3-dihydrobenzofuran-4-yl]-6-(hydroxymethyl)tetrahydro-2H-pyran-3,4,5-triol (Compound c43)

In a reaction vessel, a CH$_2$Cl$_2$/CH$_3$CN (=v/v, 1:1, 5.00 L) solution of the crude residue (328 g, 0.687 mol) obtained in accordance with the reaction pathway of 1a in the step 1 was completely dissolved while performing stirring at room temperature under nitrogen. The reaction vessel was cooled to −50° C., and then Et$_3$SiH (329 mL, 2.08 mol) and BF$_3$—OEt$_2$ (170 mL, 1.37 mol) were added dropwise for 10 minutes while keeping the internal temperature at −45° C. or lower. The reaction mixture was slowly warmed to −10° C. for 1 hour and the resulting mixture was warmed to 0° C. After performing stirring for 3 hours at 0° C., to the reaction mixture was added a saturated NaHCO$_3$ aqueous solution (5.5 L), and the pH was adjusted to 7.0 to 7.5 using a pH meter. The organic solvent was removed from the mixture using a vacuum concentrator, and the concentrate was diluted with EtOAc (2.5 L). Then, the organic layer was isolated. The aqueous layer was diluted with EtOAc (2×125 L) and extraction was performed. All organic layers were combined, dried over anhydrous MgSO$_4$ (50 g), filtered, and then the filtrate was concentrated under reduced pressure to remove the solvent. The residue was vacuum dried to obtain the title compound (307 g) as a yellow liquid. The crude residue thus obtained was used in the next step without further purification.

$^1$H NMR (500 MHz, CD$_3$OD): δ 7.04 (d, J=8.0 Hz, 2H), 6.93 (d, J=8.0 Hz, 2H), 6.83 (s, 1H), 4.61 (t, J=9.0 Hz, 2H), 4.13 (d, J=9.0 Hz, 1H), 3.99 (d, J=15.0 Hz, 1H), 3.94 (d, J=15.0 Hz, 1H), 3.87 (d, J=12.0 Hz, 1H), 3.66 (m, 1H), 3.44 (m, 1H), 3.41 (t, J=9.0 Hz, 2H), 3.36 (m, 2H), 3.31 (m, 1H), 1.83 (m, 1H), 0.91 (m, 2H), 0.63 (m, 2H); LC-MS: [M+Na]$^+$ 469.

Step 3: (2R,3R,4R,5S,6S)-2-(Acetoxymethyl)-6-[7-chloro-6-(4-cyclopropylbenzyl)-2,3-dihydrobenzofuran-4-yl]tetrahydro-2H-pyran-3,4,5-triyl triacetate (Compound c27)

To a reaction vessel were sequentially added dropwise DMAP (101 g, 0.825 mol) and Ac$_2$O (520 mL, 5.50 mol) at room temperature while stirring a CH$_2$Cl$_2$ (5.00 L) solution of the crude residue (307 g, 0.687 mol) in the step 2. The resulting yellow reaction mixture was stirred at room temperature for 2 hours. The reaction mixture was quenched with distilled water (500 mL). The mixture was layered. The organic layer was stored and the aqueous layer was extracted with dichloromethane (2×1.25 L). All organic layers were combined and rinsed with a 1 N HCl aqueous solution (2.5 L) and brine (2.5 L). The organic layer was dried over MgSO$_4$ (50 g), filtered, and then the filtrate was concentrated under reduced pressure. The residue was diluted with MeOH (2.5 L) and stirred at room temperature for 30 min. The resulting solid was filtered under reduced pressure and the filtrate was rinsed with MeOH (500 mL). The filtered solid was dried to obtain the title compound (357 g, yield: 84%, purity: >97.6%) as a white solid.

$^1$H NMR (500 MHz, CDCl$_3$): δ 7.04 (d, J=8.0 Hz, 2H), 6.95 (d, J=8.0 Hz, 2H), 6.53 (s, 1H), 5.24 (dd, J=9.5, 9.5 Hz, 1H), 5.12 (m, 2H), 4.67 (m, 2H), 4.29 (d, J=10.0 Hz, 1H), 4.24 (dd, J=12.5, 4.5 Hz, 1H), 4.13 (dd, J=12.5, 1.5 Hz, 1H), 4.02 (d, J=15.0 Hz, 1H), 3.92 (d, J=15.0 Hz, 1H), 3.77 (m, 1H), 3.38 (m, 2H), 2.07 (s, 3H), 2.06 (s, 3H), 1.99 (s, 3H), 1.84 (m, 1H), 1.66 (s, 3H), 0.92 (m, 2H), 0.63 (m, 2H); LC-MS: [M+Na]$^+$ 637.

Step 4: (2S,3R,4R,5S,6R)-2-[7-Chloro-6-(4-cyclopropylbenzyl)-2,3-dihydrobenzofuran-4-yl]-6-(hydroxymethyl)tetrahydro-2H-pyran-3,4,5-triol (Compound c28)

To a THF/MeOH (=v/v, 1:2, 4.28 L) suspension of (2R,3R,4R,5S,6S)-2-(acetoxymethyl)-6-(7-chloro-6-(4-cyclopropylbenzyl)-2,3-dihydrobenzofuran-4-yl)tetrahydro-2H-pyran-3,4,5-triyl triacetate (357 g, 0.580 mol) was added dropwise 4 M NaOH aqueous solution (668 mL, 2.67 mol) at room temperature for 20 minutes while stirring the suspension. The resulting suspension was further stirred at room temperature for 2 hours. After the reaction vessel was cooled to 0° C., to the reaction mixture was slowly added dropwise a 1 N HCl aqueous solution (1.18 L), and the pH was adjusted to 6.5 to 7.0 using a pH meter. The reaction solvent was removed using a vacuum concentrator and the concentrate was diluted with EtOAc (5.36 L) and distilled water (5.36 L). The mixture was layered. The organic layer was stored and the aqueous layer was extracted with EtOAc (2×1.79 L). All organic layers were combined and rinsed with distilled water (1.79 L). The organic layer was dried over MgSO$_4$ (710 g), filtered, and then the filtrate was concentrated under reduced pressure to obtain the crude title compound.

The crude title compound was diluted with EtOAc (3.89 L) and then stirred at reflux for 30 minutes to completely dissolve the solid. Then, the resultant was cooled to room temperature. To the resulting suspension was added dropwise isopropyl ether (1.29 L) for 10 minutes and stirring was performed 30 minutes (including the dropwise addition time). The process of adding the isopropyl ether was repeated twice. Then, the reaction vessel was cooled to 0° C. and stirred for 30 minutes. The resulting solid was filtered under reduced pressure and the filtrate was rinsed with a mixed liquid of EtOAc/isopropyl ether (=v/v, 1:1, 357 mL). The filtered solid was dried in a vacuum oven (40° C., 18 hours) to obtain the title compound (236 g, yield: 92%, purity: >99.7%) as a white solid. In addition, a total yield of the final compound of Example 6 according to the synthetic pathway of the above steps 1 to 4 was calculated as about 77%.

$^1$H NMR (500 MHz, CD$_3$OD): δ 7.04 (d, J=8.0 Hz, 2H), 6.93 (d, J=8.0 Hz, 2H), 6.83 (s, 1H), 4.61 (t, J=9.0 Hz, 2H), 4.13 (d, J=9.0 Hz, 1H), 3.99 (d, J=15.0 Hz, 1H), 3.94 (d, J=15.0 Hz, 1H), 3.87 (d, J=12.0 Hz, 1H), 3.66 (m, 1H), 3.44 (m, 1H), 3.41 (t, J=9.0 Hz, 2H), 3.36 (m, 2H), 3.31 (m, 1H), 1.83 (m, 1H), 0.91 (m, 2H), 0.63 (m, 2H); LC-MS: [M+Na]$^+$ 469.

Example 7: Production of (2S,3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol

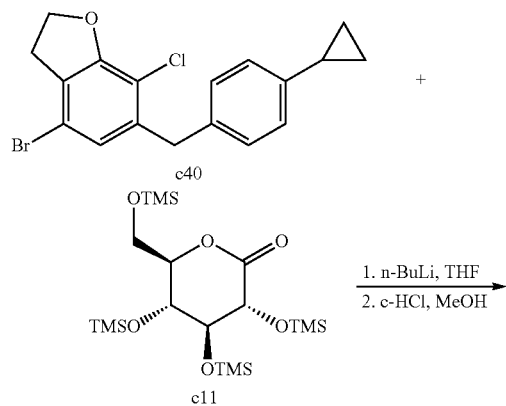

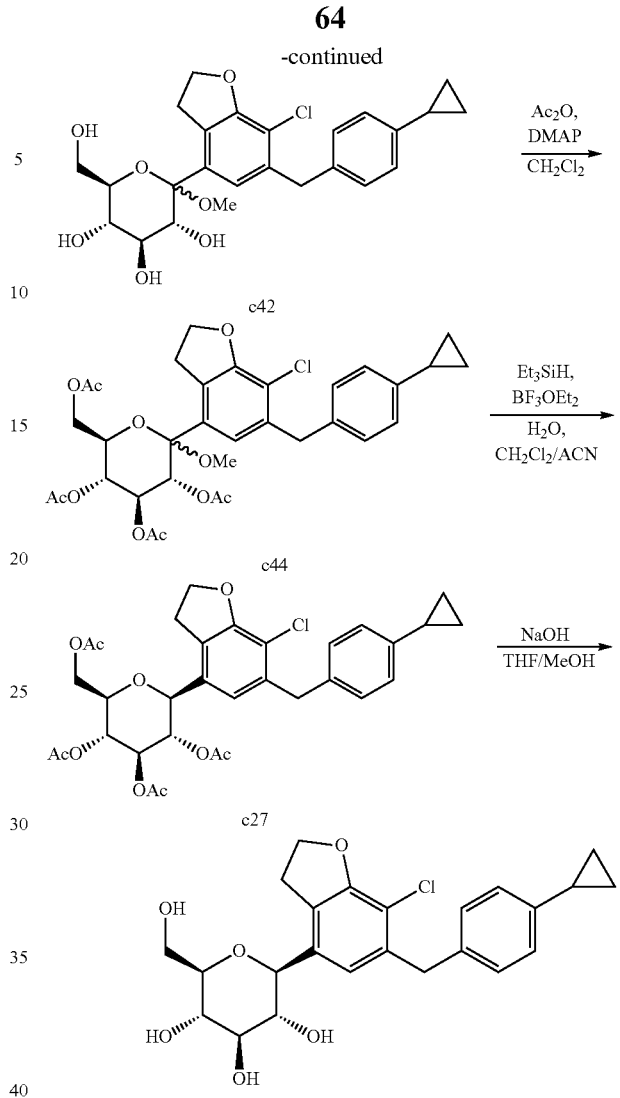

Step 1: (3R,4S,5S,6R)-2-[7-Chloro-6-(4-cyclopropylbenzyl)-2,3-dihydrobenzofuran-4-yl]-6-(hydroxymethyl)-2-methoxytetrahydro-2H-pyran-3,4,5-triol (Compound c42)

According to the reaction pathway of 1b in the step 1 of Example 6, 4-bromo-7-chloro-6-(4-cyclopropylbenzyl)-2,3-dihydrobenzofuran (21.6 g) was used to obtain the title compound (26.2 g, 93%) as a light yellow solid.

Step 2: (3R,4S,5R,6R)-6-(Acetoxymethyl)-2-[7-chloro-6-(4-cyclopropylbenzyl)-2,3-dihydrobenzofuran-4-yl]-2-methoxytetrahydro-2H-pyran-3,4,5-triyl triacetate (Compound c44)

To a reaction vessel were sequentially added dropwise DMAP (8.06 g, 66.0 mmol) and Ac$_2$O (51.8 mL, 550 mol) at room temperature while stirring a CH$_2$Cl$_2$ (65.5 L) solution of (3R,4S,5S,6R)-2-[7-chloro-6-(4-cyclopropylbenzyl)-2,3-dihydrobenzofuran-4-yl]-6-(hydroxymethyl)-2-methoxytetrahydro-2H-pyran-3,4,5-triol (26.2 g, 55.0 mmol). The resulting yellow reaction mixture was stirred at room temperature for 6 hours. The reaction mixture was quenched with distilled water (50 mL). The mixture was layered. The organic layer was stored and the aqueous layer was extracted with $CH_2Cl_2$ (2×30 mL). All organic layers were combined and rinsed with a 1 N HCl aqueous solution (50 mL) and brine (30 mL). The organic layer was dried over $MgSO_4$ (6 g), filtered, and then the filtrate was concentrated under reduced pressure. The residue was diluted with MeOH (100 mL) and stirred at room temperature for 12 hours. The resulting solid was filtered under reduced pressure and the filtrate was rinsed with MeOH (30 mL). The filtered solid was dried to obtain the title compound (29.2 g, 71% over two steps in total) as a white solid.

$^1$H NMR (500 MHz, $CDCl_3$): δ 7.01 (d, J=8.5 Hz, 2H), 6.95 (d, J=8.5 Hz, 2H), 6.65 (s, 1H), 5.53 (dd, J=10.0, 9.5 Hz, 1H), 5.19 (dd, J=10.0, 9.5 Hz, 1H), 4.99 (d, j=10.0 Hz, 1H), 4.63 (m, 2H), 4.34 (dd, J=12.0, 4.5 Hz, 1H), 4.14 (dd, J=12.0, 2.0 Hz, 1H), 4.05 (d, J=15.5 Hz, 1H), 4.01 (m, 1H), 3.99 (d, J=15.5 Hz, 1H), 3.49 (m, 1H), 3.33 (m, 1H), 3.17 (s, 3H), 2.08 (s, 3H), 2.05 (s, 3H), 1.94 (s, 3H), 1.83 (m, 1H), 1.61 (s, 3H), 0.90 (m, 2H), 0.62 (m, 2H).

Step 3: (2R,3R,4R,5S,6S)-2-(Acetoxymethyl)-6-[7-chloro-6-(4-cyclopropylbenzyl)-2,3-dihydrobenzofuran-4-yl]tetrahydro-2H-pyran-3,4,5-triyl triacetate (Compound c27)

In a reaction vessel, a $CH_2Cl_2/CH_3CN$ (=v/v, 1:10, 550 mL) solution of (3R,4S,5R,6R)-6-(acetoxymethyl)-2-[7-chloro-6-(4-cyclopropylbenzyl)-2,3-dihydrobenzofuran-4-yl]-2-methoxytetrahydro-2H-pyran-3,4,5-triyl triacetate (5.00 g, 7.75 mmol) was completely dissolved by performing stirring at room temperature. After the reaction vessel was cooled to 0° C., $Et_3SiH$ (9.89 mL, 62.0 mmol) and $BF_3$—$OEt_2$ (4.96 mL, 40.3 mmol) were sequentially added dropwise thereto for 10 minutes while keeping the internal temperature at 5° C. or lower. The reaction mixture was stirred at 5° C. or lower for 1 hour. Then, the reaction mixture was warmed to 10° C. and further stirred for 2 hours. To the reaction mixture was added a saturated $NaHCO_3$ aqueous solution, and confirmation as to whether the pH was 7.0 to 7.5 was made using a pH meter. Then, the organic solvent was removed using a vacuum concentrator. The concentrate was diluted with EtOAc (50 mL) and the organic layer was isolated. The aqueous layer was extracted with EtOAc (2×30 mL). All organic layers were combined, dried over $MgSO_4$ (5 g), filtered, and then the filtrate was concentrated under reduced pressure. The residue was dissolved in $CH_2Cl_2$ (5 mL), hexane (10 mL) was added thereto, and stirring was performed at room temperature for 5 minutes. Isopropyl ether (20 mL) was added to the mixture and stirring was performed for 30 minutes. To the resulting suspension was further added isopropyl ether (20 mL). The reaction vessel was cooled to 0° C. and stirred for 2 hours. The resulting solid was filtered under reduced pressure and the filtrate was rinsed with isopropyl ether (10 mL). The filtered solid was vacuum dried to obtain the title compound (4.38 g, 92%) as a white solid.

Step 4: (2S,3R,4R,5S,6R)-2-[7-Chloro-6-(4-cyclopropylbenzyl)-2,3-dihydrobenzofuran-4-yl]-6-(hydroxymethyl)tetrahydro-2H-pyran-3,4,5-triol (Compound c28)

According to the synthesis method described in the step 4 of Example 1 as mentioned above, (2R,3R,4R,5S,6S)-2-(acetoxymethyl)-6-[7-chloro-6-(4-cyclopropylbenzyl)-2,3-dihydrobenzofuran-4-yl]tetrahydro-2H-pyran-3,4,5-triyl triacetate (4.38 g, 7.12 mmol) was used to obtain the crude title compound. The residue was diluted with EtOAc (45.3 mL) and then stirred at reflux for 10 min to completely dissolve the solid. The resultant was cooled to room temperature. To the resulting suspension was added dropwise isopropyl ether (15.1 mL) for 10 minutes and stirring was performed 30 minutes (including the dropwise addition time). The process of adding the isopropyl ether was repeated twice. Then, the reaction vessel was cooled to 0° C. and stirred for 30 minutes. The resulting solid was filtered under reduced pressure and the filtrate was rinsed with isopropyl ether (10 mL). The filtered solid was dried in a vacuum oven (40° C., 18 hours) to obtain the title compound (2.93 g, yield: 92%, purity: >99.5%) as a white solid. A total yield of the final compound of Example 2 according to the synthetic pathway of the above steps 1 to 4 was calculated as about 60%.

Experimental Example 1: Evaluation of Yield Depending on Rearrangement Reaction Condition

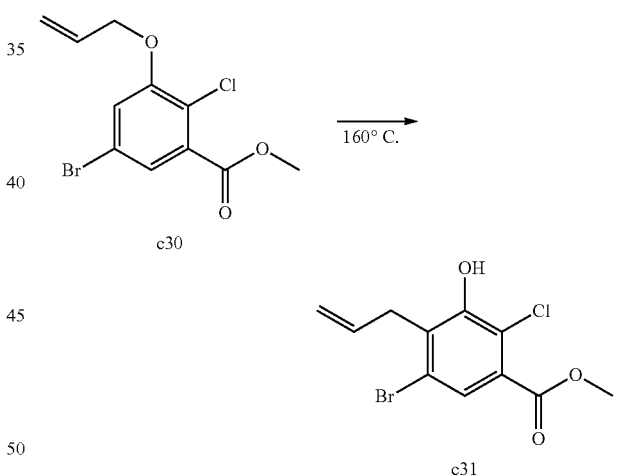

(1) Reaction Using Amine-Based Solvent or without Using Solvent

Methyl 3-(allyloxy)-5-bromo-2-chlorobenzoate (Compound c30) as a starting material was subjected to a rearrangement reaction at 160° C., so that methyl 4-allyl-5-bromo-2-chloro-3-hydroxybenzoate (Compound c31) was obtained and a yield thereof was calculated.

At this time, an amount of the starting material and a reaction condition were adjusted as shown in Table 1 below. 5 M Diethylamine (DEA) was used as a reaction solvent, or reaction was carried out without any solvent.

As a result, the yield was 67% at maximum and was not increased any further.

TABLE 1

| Test no. | Purification of starting material | Amount of starting material (g) | Reaction solvent | Reaction temperature (° C.) | Reaction time (h) | Amount of product (g) | Yield (%) |
|---|---|---|---|---|---|---|---|
| 1 | Crude | 5 | DEA (5M) | 160 | 6 | 2.0 | 40 |
| 2 | Crude | 11.2 | DEA (5M) | 160 | 13 | 6.4 | 57 |
| 3 | Crude | 10.6 | DEA (5M) | 160 | 18 | 7.1 | 67 |
| 4 | Crude | 5.4 | DEA (5M) | 160 | 24 | 3.4 | 63 |
| 5 | Crude | 10 | DEA (5M) | 160 | 13 | 5.7 | 57 |
| 6 | Crude | 1 | — | 160 | 6 | 0.2 | 20 |
| 7 | Crude | 10 | — | 160 | 5 | 2.9 | 29 |
| 8 | Crude | 10 | — | 160 | 13 | 5.8 | 58 |
| 9 | Crude | 18.6 | — | 160 | 12.5 | 11.1 | 60 |
| 10 | Crude | 13.6 | — | 160 | 12 | 8.7 | 64 |
| 11 | Crude | 10 | — | 160 | 18 | 6.1 | 61 |
| 12 | Purified | 10.5 | — | 160 | 12.5 | 4.8 | 46 |
| 13 | Purified | 9.9 | — | 160 | 18 | 3.3 | 33 |

(2) Reaction with Addition of Lewis Acid

Methyl 3-(allyloxy)-5-bromo-2-chlorobenzoate (Compound c30) as a starting material was dissolved in a solvent, and subjected to a rearrangement reaction. Then, the residue was purified by silica gel column chromatography to obtain methyl 4-allyl-5-bromo-2-chloro-3-hydroxybenzoate (Compound c31), and a yield thereof was calculated.

At this time, a reaction solvent, a reaction temperature, and Lewis acid were adjusted as shown in Table 2 below, and reaction was carried out with or without addition of the Lewis acid.

As a result, the yield was increased up to 80% in a case where diisobutylaluminum chloride ($(i\text{-}Bu)_2AlCl$) or diethylaluminum chloride ($Et_2AlCl$), which is Lewis acid, was added.

TABLE 2

| Test no. | Lewis acid | Reaction solvent | Reaction temperature | Yield |
|---|---|---|---|---|
| 1 | $BCl_3$ | $CH_2Cl_2$ | −25° C. to rt | 17% |
| 2 | $(i\text{-}Bu)_2AlCl$ | Hexane/$CH_2Cl_2$ | 0° C. to rt | 71% |
| 3 | $TiCl_4$ | Methylimidazole | rt | Unreacted |
| 4 | $TiCl_4$ | $CH_2Cl_2$ | rt | Unreacted |
| 5 | — | Water | rt | Unreacted |
| 6 | $BF_3 \cdot OEt_2$ | $CH_2Cl_2$ | 0° C. to rt | Unreacted |
| 7 | $AlCl_3$ | $CH_2Cl_2$ | 0° C. to rt | 35% |
| 8 | $(i\text{-}Bu)_2AlCl$ | Hexane/$CH_2Cl_2$ | 0° C. to rt | 80% |
| 9 | $Et_2AlCl$ | Hexane/$CH_2Cl_2$ | 0° C. to rt | 72% |

Experimental Example 2: Evaluation of Yield Depending on Cyclization Reaction Condition (1) Cyclization Using Vilsmeier Reagent

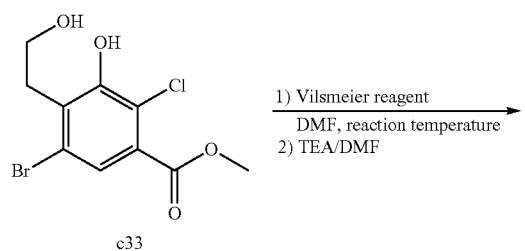

c33

1) Vilsmeier reagent
DMF, reaction temperature
2) TEA/DMF

-continued

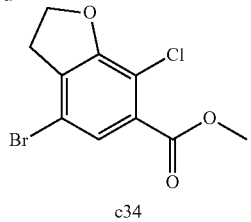

c34

Production of Vilsmeier reagent (production reagent A);
To a solution of N,N-dimethylformamide (5.6 mL, 74.24 mmol) was added $SOCl_2$ (5.3 mL, 72.24 mmol) at room temperature. The mixture was stirred at 40° C. for 2 hours, and then concentrated in vacuo to obtain a Vilsmeier reagent which is a hygroscopic white solid.

Production of Vilsmeier reagent (production reagent B);
To a solution of N,N-dimethylformamide (2.9 mL, 37.07 mmol) was added $SOCl_2$ (2.7 mL, 37.07 mmol) at room temperature. The mixture was stirred at 40° C. for 2 hours, and then concentrated in vacuo to obtain a Vilsmeier reagent which is a hygroscopic white solid.

Then, to a mixture of the Vilsmeier reagent in DMF was slowly added methyl 5-bromo-2-chloro-3-hydroxy-4-(2-hydroxyethyl)benzoate (Compound c33) in DMF. The mixture was subjected to a cyclization reaction while performing stirring for 1 hour, to obtain methyl 4-bromo-7-chloro-2,3-dihydrobenzofuran-6-carboxylate (Compound c34), and a yield thereof was calculated.

At this time, a starting material, a reaction temperature, and the like were adjusted as shown in Table 3 below, and a reaction was performed.

As a result, a cyclized product was obtained at a generally high yield. However, in a case where the starting material was impure, the product was recovered as a low yield.

TABLE 3

| Test no. | Properties of starting material | Amount of starting material | Vilsmeier reagent | Reaction temperature | Color of product | Amount of product | Yield |
|---|---|---|---|---|---|---|---|
| 1 | Brown solid | 0.5 g | Reagent manufactured by Sigma-Aldrich Co. LLC | −20° C. | Light yellow | 0.31 g | 66% |
| 2 | Brown solid | 1.0 g | Production reagent A | −20° C. | Light yellow | 0.66 g | 70% |
| 3 | Brown solid | 5.4 g | Production reagent A | −20° C. | Light yellow | 3.57 g | 70% |
| 4 | White solid | 1.0 g | Production reagent A | 0° C. to 15° C. | Light yellow | 0.75 g | 80% |
| 5 | Brown viscous solid | 1.0 g | Production reagent A | 0° C. to 15° C. | Light yellow | 0.12 g | 13% |
| 6 | Brown solid | 7.6 g | Production reagent B | 0° C. to 15° C. | Light brown | 5.86 g | 81% |

(2) Cyclization Using Leaving Group

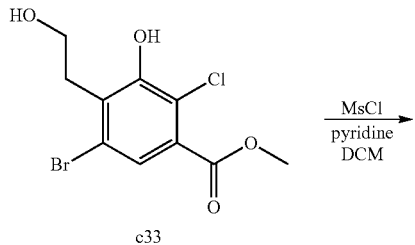

c33

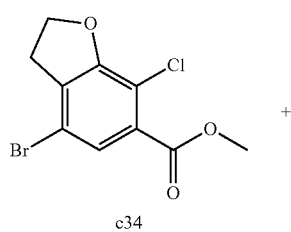

c34

+

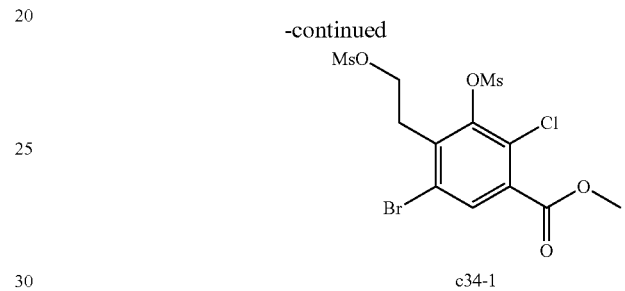

c34-1

To methyl 5-bromo-2-chloro-3-hydroxy-4-(2-hydroxyethyl)benzoate (Compound c33) as a starting material was added mesyl chloride (MsCl) together with a solvent. The mixture was subjected to a cyclization reaction, to obtain methyl 4-bromo-7-chloro-2,3-dihydrobenzofuran-6-carboxylate (Compound c34), and a yield thereof was calculated.

At this time, an amount used of a reactant, an addition method, and a reaction condition were adjusted as shown in Table 4 below, and a reaction was performed.

As a result, the desired compound was sometimes obtained at a high yield. However, there was inconvenience caused by equivalent control of MsCl and dropwise addition.

TABLE 4

| Test no. | Reactant | Solvent | Addition method | Reaction temperature | Reaction time | Product (c34) yield | By-product (c34-1) yield |
|---|---|---|---|---|---|---|---|
| 1 | MsCl 1.1 eq | Pyridine/DCM | Addition | −18° C. | Overnight | 62% | 34% |
| 2 | MsCl 3.3 eq | Pyridine/DCM | Dropwise addition for 2 hours | rt | Overnight | 19% | 35% |
| 3 | MsCl 3.3 eq | Pyridine/DCM | Dropwise addition for 2 hours | rt | 1 hour | 46% | 47% |
| 4 | MsCl 1.2 eq | Pyridine/DCM | Dropwise addition for 2 hours | 0° C. | 1 hour | 51% | 46% |
| 5 | MsCl 1.2 eq | Pyridine/DCM | Dropwise addition for 2 hours | 55° C. | 1 hour | 86% | 9% |
| 6 | MsCl 1.1 eq | Pyridine/DCM | Trace amount addition | 55° C. | 1 hour | 71% | |
| 7 | MsCl 1.1 eq | Pyridine/DCM | Trace amount addition | 55° C. | 1 hour | 56% | |

TABLE 4-continued

| Test no. | Reactant | Solvent | Addition method | Reaction temperature | Reaction time | Product (c34) yield | By-product (c34-1) yield |
|---|---|---|---|---|---|---|---|
| 8 | MsCl 1.1 eq | Pyridine/DCM | Dropwise addition for 2 hours | 60° C. | 1 hour | 90% | |

(3) Cyclization Using Halide or Mitsunobu Reaction

Methyl 5-bromo-2-chloro-3-hydroxy-4-(2-hydroxyethyl)benzoate (Compound c33) as a starting material was subjected to a cyclization reaction through a halide or a Mitsunobu reaction, to obtain methyl 4-bromo-7-chloro-2,3-dihydrobenzofuran-6-carboxylate (Compound c34), and a yield thereof was calculated.

At this time, a reagent in which triphenylphosphine ($PPh_3$), imidazole, iodine ($I_2$), and toluene are combined was used for the cyclization reaction using a halide, and a reagent in which triphenylphosphine ($PPh_3$), diisopropyl azodicarboxylate (DIAD), and tetrahydrofuran (THF) are combined was used for the Mitsunobu reaction.

As a result, a yield of up to about 60% was obtained. However, there was inconvenience of having to remove triphenylphosphine oxide, which is a by-product generated after the reaction.

Experimental Example 3: Evaluation of Yield Depending on Reduction Reaction Conditions

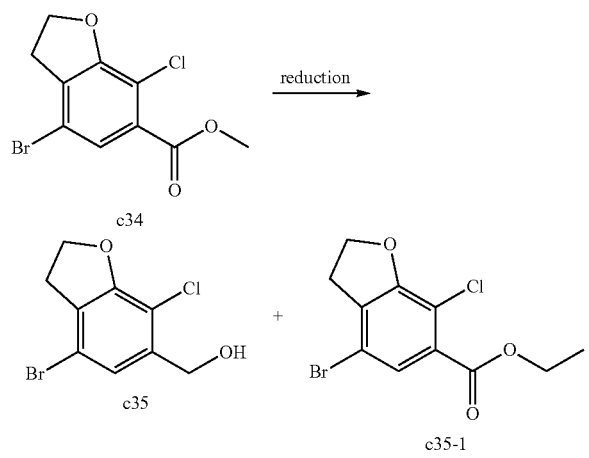

To methyl 4-bromo-7-chloro-2,3-dihydrobenzofuran-6-carboxylate (Compound c34) as a starting material was added $NaBH_4$ (3 eq) and was also added or not added Lewis acid. Then, the mixture was subjected to a reduction reaction in a solvent at room temperature, to obtain (4-bromo-7-chloro-2,3-dihydrobenzofuran-6-yl)methanol (Compound c35), and a yield thereof was calculated. In addition, an amount of a by-product 1 (Compound c35-1) was also measured.

(1) A reaction solvent and an amount added of Lewis acid were adjusted as shown in Table 5 below, and a reaction was performed. As a result, it was possible to obtain the product at the highest yield in a case where THF/EtOH (1:1) was used as a reaction solvent, and a good yield of 95% was obtained even in a case where only $NaBH_4$ was used without Lewis acid.

TABLE 5

| Test no. | Reaction solvent | $NaBH_4$ (eq) | Lewis acid | Reaction result (weight ratio) (stating material:product:by-product 1) |
|---|---|---|---|---|
| 1 | Methanol | 3.0 | — | 68:31:— |
| 2 | Ethanol | 3.0 | — | —:77:21 |
| 3 | THF/methanol (1:1) | 3.0 | — | 52:43:— |
| 4 | THF/ethanol (1:1) | 3.0 | — | —:95:— |
| 5 | THF/water (1:1) | 3.0 | — | 50:48:— |
| 6 | Dioxane/water (1:1) | 3.0 | — | 42:57:— |
| 7 | THF/methanol (1:1) | 3.0 | LiCl (1.5 eq) | 52:43:— |
| 8 | THF/ethanol (1:1) | 3.0 | LiCl (1.5 eq) | —:93:6 |

(2) Without addition of Lewis acid, a reaction solvent and an amount added of $NaBH_4$ were adjusted as shown in Table 6 below, and a reaction was performed. As a result, in a case where $NaBH_4$ was added in an amount of 3 eq under a condition of THF/EtOH (1:1) or THF/EtOH (2:1) as a reaction solvent, a good yield of 95% was obtained without a by-product.

TABLE 6

| Test no. | Reactant | $NaBH_4$ (eq) | Reaction result (weight ratio) (stating material:product:by-product 1:by-product 2) |
|---|---|---|---|
| 1 | Methanol | 3.0 | 68:31:—:— |
| 2 | Ethanol | 3.0 | —:77:21:— |
| 3 | THF/methanol (1:1) | 3.0 | 52:43:—:— |
| 4 | THF/ethanol (1:1) | 3.0 | —:95:—:— |
| 5 | THF/water (1:1) | 3.0 | 50:48:—:— |
| 6 | Dioxane/water (1:1) | 3.0 | 42:57:—:— |
| 7 | THF/ethanol (2:1) | 3.0 | —:95:—:— |
| 8 | THF/ethanol (5:1) | 3.0 | 30:60:—:10 |
| 9 | THF/ethanol (10:1) | 3.0 | —:70:—:30 |
| 10 | THF/ethanol (1:1) | 1.2 | 50:50:—:— |
| 11 | THF/ethanol (1:1) | 1.5 | 25:75:—:— |
| 12 | THF/ethanol (2:1) | 2.0 | 10:90:—:— |
| 13 | THF/ethanol (2:1) | 1.2 | 21:53:25:— |
| 14 | THF/ethanol (2:1) | 1.5 | 18:58:24:— |
| 15 | THF/ethanol (2:1) | 2.0 | 17:63:19:— |

* By-product 2: Unidentified substance (3) A reaction solvent, an amount added of $NaBH_4$, and an amount added of Lewis acid were adjusted as shown in Table 7 below, and a reaction was performed. As a result, the reaction did not proceed in a case where only THF was used or THF/i-PrOH was used, as a reaction solvent. On the other hand, in a case where THF/ethanol was used as a reaction solvent, a good yield of 95% or higher was obtained even by using only $NaBH_4$ without Lewis acid.

TABLE 7

| Test no. | Reactant | NaBH$_4$ (eq) | Lewis acid | Reaction result (weight ratio) (stating material:product:by-product1) |
|---|---|---|---|---|
| 1 | THF | 2.0 | — | 100:—:— |
| 2 | Ethanol/water (4:1) | 2.0 | CaCl$_2$ (1.0 eq) | —:60:40 |
| 3 | THF/methanol (1:1) | 3.0 | CaCl$_2$ (1.5 eq) | 70:30:— |
| 4 | THF/ethanol (1:1) | 2.4 | CaCl$_2$ (1.2 eq) | —:100:— |
| 5 | THF/ethanol (1:1) | 3.0 | CaCl$_2$ (1.5 eq) | —:100:— |
| 6 | THF/ethanol (2:1) | 3.0 | — | —:100:— |
| 7 | THF/isopropanol (1:1) | 3.0 | CaCl$_2$ (1.5 eq) | 100:—:— |

Experimental Example 4: Production and Analysis of Crystalline Form

From a compound produced according to the method of the present invention, specifically, crude (2S,3R,4R,5S,6R)-2-(7-chloro-6-(4-cyclopropylbenzyl)-2,3-dihydrobenzofuran-4-yl)-6-(hydroxymethyl)tetrahydro-2H-pyran-3,4,5-triol (Compound c28) which had been obtained according to the steps 1 to 14 in Example 1, crystals were produced through a crystallization process in various solvents and analyzed.

For an XRD spectrum, powder X-ray diffraction was measured using an X-ray diffractometer by irradiation with a Cu—K$_\alpha$ radiation (wavelength, λ=1.54056 Å) according to an ordinary method.

For differential scanning calorimetry (DSC), measurement was performed at a rate of +1° C./min using a differential scanning calorimeter.

(1) Production of Crystal Using Toluene Solvent

Crystallization using toluene is similar to that described in a later portion of a procedure of the step 14 in Example 1. Specifically, a toluene (8-fold with respect to a weight of c28) solution of the crude compound c28 was dissolved by being heated at 40° C. for 30 minutes, and then cooled to room temperature. After the suspension was formed at room temperature, stirring was further performed for 30 minutes. The resulting precipitate was filtered, washed with toluene (2-fold of a volume of the filtrate), and then dried in a vacuum oven (50° C., 12 hours) to obtain a white crystal (yield: 91.8%).

An XRD spectrum of the produced crystal showed a crystalline form (crystalline form A) as shown in FIG. 1, and diffraction angles (2θ), interplanar spacings (d), and relative intensities (I/I$_o$×100) of characteristic peaks are summarized in Table 8.

TABLE 8

| 2θ (±0.2°) | d (Å) | I/I$_o$ (%) |
|---|---|---|
| 6.2 | 14.1 | 10.1 |
| 7.2 | 12.1 | 20.7 |
| 8.8 | 10.0 | 11.5 |
| 15.4 | 5.8 | 9.6 |
| 17.6 | 5.0 | 20.1 |
| 18.6 | 4.7 | 9.9 |
| 19.0 | 4.6 | 21.7 |
| 21.6 | 4.1 | 5.4 |
| 22.5 | 3.9 | 15.3 |
| 23.8 | 3.7 | 7.3 |
| 25.1 | 3.5 | 13.3 |

As shown in FIG. 2, a DSC spectrum made it possible to confirm a melting endothermic peak of the crystal.

(2) Production of Crystal Using Ethyl Acetate Solvent

Crystallization using ethyl acetate is similar to that described in a later portion of the step 4 in Example 6. Specifically, an ethyl acetate (15-fold with respect to a weight of c28) solution of the crude compound c28 was dissolved by performing stirring at reflux, and then cooled to room temperature. After the suspension was formed at room temperature, stirring was further performed for 30 minutes. To the resulting mixture was added dropwise isopropyl ether (15-fold with respect to a weight of c28) over 30 minutes, and stirring was further performed at room temperature for 30 minutes. The resulting precipitate was filtered, washed with 0° C. ethyl acetate (2-fold with respect to a weight of c28), and then dried in a vacuum oven (50° C., 12 hours) to obtain a white crystal (yield: 88.3%). An XRD spectrum analysis of the produced crystal showed the same crystalline form (crystalline form A) as in (1) of Experimental Example 4.

(3) Production of Crystal Using Dichloromethane Solvent

A dichloromethane (170-fold with respect to a weight of c28) solution of the crude compound c28 was dissolved by being heated at 40° C., and then cooled to room temperature. The mixture was stirred at room temperature for 30 minutes. To the reaction mixture was added Compound c28 (10 mg, seed) obtained in the step 4 of Example 6, and then stirring was performed for 12 hours. The resulting precipitate was filtered, washed with dichloromethane (twice with respect to a weight of c28), and then dried in a vacuum oven (50° C., 12 hours) to obtain a white crystal (yield: 50.1%). An XRD spectrum analysis of the produced crystal showed the same crystalline form (crystalline form A) as in (1) of Experimental Example 4.

(4) Production of Crystal Using Acetone Solvent

An acetone (35-fold with respect to a weight of c28) solution of the crude compound c28 was dissolved by performing heating at reflux, and then cooled to room temperature. After the suspension was formed at room temperature, stirring was further performed for 3 hours. The resulting precipitate was filtered, washed with acetone (2-fold of a volume of the filtrate), and then dried in a vacuum oven (50° C., 12 hours) to obtain a white crystal (yield: 38.2%). An XRD spectrum analysis of the produced crystal showed the same crystalline form (crystalline form A) as in (1) of Experimental Example 4.

(5) Production of Crystal Using Acetonitrile Solvent

An acetonitrile (10-fold with respect to a weight of c28) solution of the crude compound c28 was dissolved by being heated at 60° C., and then cooled to room temperature. After the suspension was formed at room temperature, stirring was further performed for 1 hour. The resulting precipitate was filtered, washed with acetonitrile (2-fold of a volume of the filtrate), and then dried in a vacuum oven (50° C., 12 hours) to obtain a white crystal (yield: 39.4%). An XRD spectrum analysis of the produced crystal showed the same crystalline form (crystalline form A) as in (1) of Experimental Example 4.

(6) Production of Crystal Using 2-Propanol Solvent

A 2-propanol (10-fold with respect to a weight of c28) solution of the crude compound c28 was dissolved by being heated at 60° C., and then cooled to room temperature. After the suspension was formed at room temperature, stirring was further performed for 30 minutes. To the reaction mixture was further added dropwise 2-propanol (5-fold with respect to a weight of c28), and then stirring was performed for 30 minutes. The resulting precipitate was filtered, washed with 2-propanol (2-fold of a volume of the filtrate), and then dried in a vacuum oven (50° C., 12 hours) to obtain a white crystal (yield: 9.5%). An XRD spectrum analysis of the produced crystal showed the same crystalline form (crystalline form A) as in (1) of Experimental Example 4.

(7) Production of Crystal Using Tetrahydrofuran/Dichloromethane Solvent

A tetrahydrofuran (5-fold with respect to a weight of c28) solution of the crude compound c28 was dissolved by performing stirring at room temperature for 30 minutes. The reaction mixture was concentrated under reduced pressure to remove the organic solvent. The concentrated residue was diluted with dichloromethane (30-fold with respect to a weight of c28) and stirred at room temperature. After the suspension was formed, stirring was further performed for 30 minutes. The resulting precipitate was filtered, washed with dichloromethane (2-fold of a volume of the filtrate), and then dried in a vacuum oven (50° C., 12 hours) to obtain a white crystal (yield: 65.3%). An XRD spectrum analysis of the produced crystal showed the same crystalline form (crystalline form A) as in (1) of Experimental Example 4.

(8) Production of Crystal Using Tetrahydrofuran/n-Hexane Solvent

A tetrahydrofuran (5-fold with respect to a weight of c28) solution of the crude compound c28 was dissolved by performing stirring at room temperature for 30 minutes. To the reaction mixture was added dropwise n-hexane (10-fold with respect to a weight of c28), and stirring was performed for 1 hour. To the resulting suspension was further added dropwise n-hexane (10-fold with respect to a weight of c28), and then stirring was performed for 30 minutes. To the reaction suspension was repeatedly added dropwise n-hexane (5-fold with respect to a weight of c28), and stirring was performed for 30 minutes. The resulting precipitate was filtered, washed with n-hexane (5-fold of a volume of the filtrate), and then dried in a vacuum oven (50° C., 12 hours) to obtain a white crystal (yield: 99.6%). An XRD spectrum analysis of the produced crystal showed the same crystalline form (crystalline form A) as in (1) of Experimental Example 4.

(9) Production of Crystal Using Methanol/Distilled Water Solvent

A methanol (5-fold with respect to a weight of c28) solution of the crude compound c28 was dissolved by performing stirring at room temperature for 30 minutes. To the reaction mixture was added dropwise distilled water (10-fold with respect to a weight of c28), and then stirring was performed for 30 minutes. To the resulting suspension was further added dropwise distilled water (10-fold with respect to a weight of c28), and then stirring was performed for 1 hour. The resulting precipitate was filtered, washed with distilled water (2-fold of a volume of the filtrate), and then dried in a vacuum oven (50° C., 12 hours) to obtain a white crystal (yield: 100%).

An XRD spectrum of the produced crystal showed the same crystalline form (crystalline form B) as shown in FIG. 3, and diffraction angles (2θ), interplanar spacings (d), and relative intensities (I/I$_o$×100) of characteristic peaks are summarized in Table 9.

TABLE 9

| 2θ (±0.2°) | d (Å) | I/I$_o$ (%) |
|---|---|---|
| 5.6 | 15.7 | 30.5 |
| 7.0 | 12.5 | 100 |
| 9.4 | 9.3 | 28.9 |

TABLE 9-continued

| 2θ (±0.2°) | d (Å) | I/I$_o$ (%) |
|---|---|---|
| 11.0 | 8.0 | 23.9 |
| 14.9 | 5.9 | 67.6 |
| 17.7 | 4.9 | 85.6 |
| 18.8 | 4.7 | 71.9 |
| 20.6 | 4.3 | 58.9 |
| 21.8 | 4.0 | 64.0 |
| 23.5 | 3.7 | 87.6 |

As shown in FIG. 4, a DSC spectrum made it possible to confirm a melting endothermic peak of the crystal.

(10) Production of Crystal Using Methanol/n-Hexane Solvent

A methanol (5-fold with respect to a weight of c28) solution of the crude compound c28 was dissolved by performing stirring at room temperature for 30 minutes. To the reaction mixture was added dropwise n-hexane (15-fold with respect to a weight of c28), and stirring was performed for 30 minutes. To the resulting suspension was further added dropwise n-hexane (10-fold with respect to a weight of c28), and stirring was performed for 1 hour. The resulting precipitate was filtered, washed with n-hexane (5-fold of a volume of the filtrate), and then dried in a vacuum oven (50° C., 12 hours) to obtain a white crystal (yield: 97.1%). An XRD spectrum analysis of the produced crystal showed the same crystalline form (crystalline form B) as in (9) of Experimental Example 4.

(11) Production of Crystal Using Methanol/Dichloromethane/n-Hexane Solvent

A dichloromethane/methanol (20:1-fold with respect to a weight of c28) solution of the crude compound c28 was dissolved by performing stirring at room temperature for 30 minutes. To the reaction mixture was added dropwise n-hexane (10-fold with respect to a weight of c28), and stirring was performed for 1 hour. To the resulting suspension was further added dropwise n-hexane (10-fold with respect to a weight of c28), and stirring was performed for 30 minutes. To the reaction suspension was repeatedly added dropwise n-hexane (5-fold with respect to a weight of c28), and stirring was performed for 30 minutes. The resulting precipitate was filtered, washed with n-hexane (5-fold of a volume of the filtrate), and then dried in a vacuum oven (50° C., 12 hours) to obtain a white crystal (yield: 99.2%). An XRD spectrum analysis of the produced crystal showed the same crystalline form (crystalline form B) as in (9) of Experimental Example 4.

(12) Production of Crystal Using Tetrahydrofuran/Toluene Solvent

A tetrahydrofuran (5-fold with respect to a weight of c28) solution of the crude compound c28 was dissolved by performing stirring at room temperature for 30 minutes. The reaction mixture was concentrated under reduced pressure to remove the organic solvent. The concentrated residue was diluted with toluene (30-fold with respect to a weight of c28) and then stirred at room temperature for 1 hour. The resulting precipitate was filtered, washed with toluene (2-fold of a volume of the filtrate), and then dried in a vacuum oven (50° C., 12 hours) to obtain a white crystal (yield: 76.1%).

An XRD spectrum of the produced crystal showed the same crystalline form (crystalline form C) as shown in FIG. 5, and diffraction angles (2θ), interplanar spacings (d), and relative intensities (I/I$_o$×100) of characteristic peaks are summarized in Table 10.

TABLE 10

| 2θ (±0.2°) | d (Å) | I/I$_o$ (%) |
|---|---|---|
| 5.6 | 15.9 | 26.9 |
| 7.3 | 12.0 | 39.9 |
| 15.7 | 5.6 | 29.1 |
| 17.2 | 5.1 | 26.2 |
| 18.9 | 4.6 | 100.0 |
| 19.9 | 4.4 | 21.2 |
| 21.2 | 4.1 | 25.4 |
| 21.9 | 4.0 | 29.2 |
| 23.1 | 3.8 | 24.7 |

As shown in FIG. 6, a DSC spectrum made it possible to confirm a melting endothermic peak of the crystal.

(13) Production of Crystal Using Ethanol/Distilled Water/n-Hexane Solvent

An ethanol (5-fold with respect to a weight of c28) solution of the crude compound c28 was dissolved by being heated at 50° C., and then cooled to room temperature. To the reaction mixture was added dropwise distilled water (10-fold with respect to a weight of c28) and stirring was performed 1 hour. To the resulting suspension was further added dropwise distilled water (10-fold with respect to a weight of c28), and stirring was performed for 30 minutes. To the reaction suspension was added dropwise n-hexane (1-fold with respect to a weight of c28), and stirring was performed for 1 hour. The resulting precipitate was filtered, washed with distilled water (2-fold of a volume of the filtrate), and then dried in a vacuum oven (50° C., 12 hours) to obtain a white crystal (yield: 95.8%). An XRD spectrum analysis of the produced crystal showed the same crystalline form (crystalline form C) as in (12) of Experimental Example 4.

(14) Production of Crystal Using Ethanol/n-Hexane Solvent

An ethanol (5-fold with respect to a weight of c28) solution of the crude compound c28 was dissolved by being heated at 50° C., and then cooled to room temperature. To the reaction mixture was added dropwise n-hexane (5-fold with respect to a weight of c28), and stirring was performed for 30 minutes. To the resulting suspension was further added dropwise n-hexane (10-fold with respect to a weight of c28), and stirring was performed for 30 minutes. To the reaction suspension was repeatedly added dropwise n-hexane (5-fold with respect to a weight of c28), and stirring was performed for 30 minutes. The resulting precipitate was filtered, washed with n-hexane (5-fold of a volume of the filtrate), and then dried in a vacuum oven (50° C., 12 hours) to obtain a white crystal (yield: 96.5%).

An XRD spectrum of the produced crystals showed the same crystalline form (crystalline form D) as shown in FIG. 7, and diffraction angles (2θ), interplanar spacings (d), and relative intensities (I/I$_o$×100) of characteristic peaks are summarized in Table 11.

TABLE 11

| 2θ (±0.2°) | d (Å) | I/I$_o$ (%) |
|---|---|---|
| 5.5 | 15.8 | 6.1 |
| 7.2 | 12.2 | 17.5 |
| 15.3 | 5.7 | 12.7 |
| 17.2 | 5.1 | 9.8 |
| 17.6 | 5.0 | 9.8 |
| 18.9 | 4.6 | 31.3 |
| 20.0 | 4.4 | 5.2 |
| 21.1 | 4.2 | 6.6 |
| 22.5 | 3.9 | 3.3 |
| 25.1 | 3.5 | 2.9 |

As shown in FIG. 8, a DSC spectrum made it possible to confirm a melting endothermic peak of the crystal.

Experimental Example 5: Confirmation of Stability of Crystalline Form

Using the crystalline form produced in (2) of Experimental Example 4, stability confirmation tests in connection with properties, identification test, moisture content, specific rotation, related substances, and content was performed for 3 months under accelerated (temperature: 40±2° C., relative humidity: 75±5%) and long-term (temperature: 25±2° C., relative humidity: 60±5%) test conditions thereof. The results of the stability confirmation tests are shown in Table 12.

TABLE 12

| Item | | Criterion | Initial period | Accelerated, on 1 month | Accelerated, on 3 months | Long term, on 3 months |
|---|---|---|---|---|---|---|
| Properties | | White or whitish powder | White powder | White powder | White powder | White powder |
| Identification test | LC | Matched | Matched | Matched | Matched | Matched |
| | IR | Matched | Matched | Matched | Matched | Matched |
| | XRD | Matched | Matched | Matched | Matched | Matched |
| Moisture (%) | | 0.5 or lower | 0.19 | 0.20 | 0.14 | 0.18 | 0.19 |
| Specific rotation (°) | | +37 to +41 | 38.0 | 37.9 | 38.9 | 38.8 |
| Related substances (%) | | Other individual related substances < 0.1 | 0.05 | 0.05 | 0.05 | 0.05 |
| Content (%) | | Total related substances < 1.0 98.0~102.0 | 0.15 99.50 | 0.16 99.60 | 0.16 100.97 | 0.16 100.20 |

(1) The properties test confirmed that there was no change in properties of the crystalline form under accelerated and long-term conditions.

(2) The identification test was conducted using the infrared spectrophotometry and the liquid chromatography among the general test methods prescribed in the Korean Pharmacopoeia, and confirmed that the crystalline form exhibited the same spectrum as a standard product in both test methods.

<Analytic Conditions>
Column: Capcdell-pak C18 MG (USPL1), 250×4.6 mm, 5 μm
Temperature: 35° C.
Detector: Light-diode array (PDA) detector (measurement wavelength: 225 nm)
Flow rate: 1.0 mL/min
Mobile phase: Buffer/methanol (25:75)
Buffer: Buffer obtained by dissolving 1.36 g of potassium dihydrogen phosphate in 1,000 mL of distilled water and then adjusting the pH to 3.0 with phosphoric acid.

(3) In a case of the XRD spectrum, it could be confirmed that there was no change in the crystalline form under accelerated and long-term conditions.

(4) In a case of being measured according to the moisture measurement method among the general test methods prescribed in the Korean Pharmacopoeia, the moisture content test could confirm the results that the crystalline form hardly exhibits a moisture-containing property under accelerated and long-term conditions.

(5) The specific rotation confirmation test could confirm structural stability of the crystalline form under accelerated and long-term conditions.

(6) The stability confirmation test in connection with related substances was conducted by the liquid chromatography method among the general test methods prescribed in the Korean Pharmacopoeia. An analytical time of the sample solution was such that measurement was performed up to three times a holding time of a main peak. Peak areas of the standard solution (0.05 mg/mL) and the sample solution (1 mg/mL), except for all peaks appearing in the blank test solution, were calculated according to an expression for calculation. As a result, stability of the crystalline form in connection with related substances under accelerated and long-term conditions could be confirmed.

Analytic conditions: Liquid chromatography analysitic conditions for the confirmation test in (2) of Experimental Example 5

Expression for calculation: Other individual related substances (%)=(Peak area of each related substance in test sample×amount used of standard product×purity of standard product)/(peak area of main peak of standard solution×amount used of specimen×dilution factor)

(7) For the content test, a methanol solution of the standard product was used as the standard solution (0.2 mg/mL), and a methanol solution of the crystalline form was used as the sample solution (1 mg/mL). The sample solution and the standard solution were tested by the liquid chromatography method in the general test methods prescribed in the Korean Pharmacopoeia, and the peak areas of the standard solution and the sample solution were used to perform calculation by the following expression for calculation. As a result, stability of the crystalline form which exhibits almost no change in content under accelerated and long-term conditions could be confirmed.

Analytic conditions: Liquid chromatography analysitic conditions for the confirmation test in (2) of Experimental Example 5

Expression for calculation: Other individual related substances (%)=(Peak area of main peak of test sample× amount used of standard product×purity of standard product)/[peak area of main peak of standard solution× amount used of specimen×(100−moisture content of specimen)]

The invention claimed is:

1. A crystalline form of a compound of the following Formula c28:

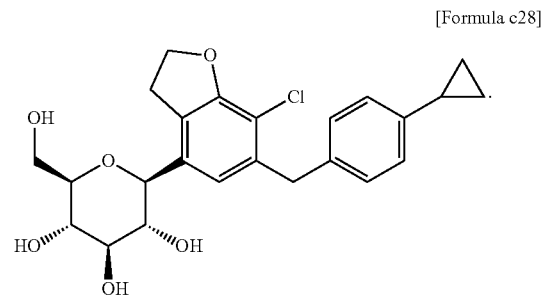

[Formula c28]

wherein the crystalline form has an X-ray diffraction (XRD) spectrum which includes peaks at diffraction angles (2θ) of 6.2°±0.2°, 7.2°±0.2°, 8.8°±0.2°, 17.6°±0.2°, 19.0°±0.2°, 22.5°±0.2°, and 25.1°±0.2° in a case of being irradiated using a Cu—K$_\alpha$ light source.

2. A crystalline form of a compound of the following Formula c28:

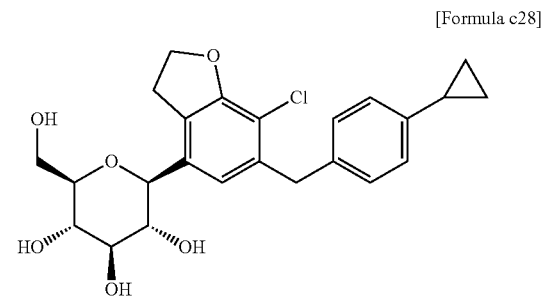 [SMILES: OC[C@H]1O[C@@H](c2cc(Cc3ccc(C4CC4)cc3)c(Cl)c3c2CCO3)[C@H](O)[C@@H](O)[C@@H]1O]

[Formula c28]

wherein the crystalline form has an X-ray diffraction (XRD) spectrum which includes peaks at diffraction angles (2θ) of 7.0°±0.2°, 14.9°±0.2°, 17.7°±0.2°, 18.8°±0.2°, 20.6°±0.2°, 21.8°±0.2°, and 23.5°±0.2° in a case of being irradiated using a Cu—K$_\alpha$ light source.

3. A crystalline form of a compound of the following Formula c28:

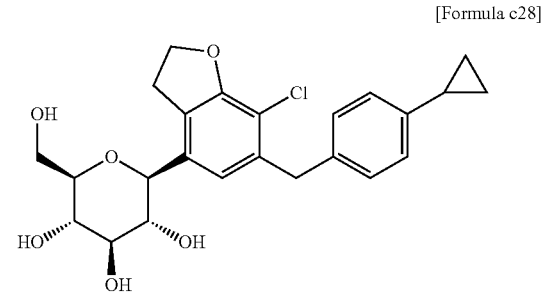 [SMILES: OC[C@H]1O[C@@H](c2cc(Cc3ccc(C4CC4)cc3)c(Cl)c3c2CCO3)[C@H](O)[C@@H](O)[C@@H]1O]

[Formula c28]

wherein the crystalline form has an X-ray diffraction (XRD) spectrum which includes peaks at diffraction angles (2θ) of 5.6°±0.2°, 7.3°±0.2°, 15.7°±0.2°, 17.2°±0.2°, 18.9°±0.2°, 21.2°±0.2°, and 21.9°±0.2° in a case of being irradiated using a Cu—K$_\alpha$ light source.

4. A crystalline form of a compound of the following Formula c28:
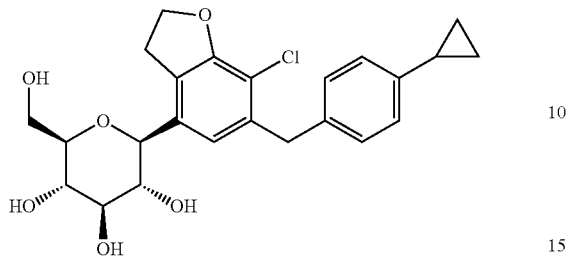
[Formula c28]
wherein the crystalline form has an X-ray diffraction (XRD) spectrum which includes peaks at diffraction angles (2θ) of 5.5°±0.2°, 7.2°±0.2°, 15.3°±0.2°, 17.2°±0.2°, 17.6°±0.2°, 18.9°±0.2°, and 21.1°±0.2° in a case of being irradiated using a Cu—K$_\alpha$ light source.
* * * * *